US008524684B2

(12) United States Patent
Iversen et al.

(10) Patent No.: US 8,524,684 B2
(45) Date of Patent: *Sep. 3, 2013

(54) ANTISENSE ANTIVIRAL COMPOUNDS AND METHODS FOR TREATING A FILOVIRUS INFECTION

(75) Inventors: Patrick L. Iversen, Corvallis, OR (US); Dwight D. Weller, Corvallis, OR (US)

(73) Assignee: AVI BioPharma, Inc., Corvallis, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/469,892

(22) Filed: May 11, 2012

(65) Prior Publication Data

US 2013/0011420 A1    Jan. 10, 2013

Related U.S. Application Data

(63) Continuation of application No. 13/853,180, filed on Aug. 9, 2010, now Pat. No. 8,198,429.

(51) Int. Cl.
*C12N 15/11* (2006.01)
*A61K 48/00* (2006.01)
*C07H 21/02* (2006.01)
*C07H 21/04* (2006.01)

(52) U.S. Cl.
USPC ........................................ 514/44 A; 536/24.5

(58) Field of Classification Search
USPC .......................................... 536/24.5; 514/44
See application file for complete search history.

(56) References Cited

U.S. PATENT DOCUMENTS

| | | | |
|---|---|---|---|
| 5,034,506 A | 7/1991 | Summerton et al. | 528/391 |
| 5,142,047 A | 8/1992 | Summerton et al. | 544/118 |
| 5,166,315 A | 11/1992 | Summerton et al. | 528/406 |
| 5,185,444 A | 2/1993 | Summerton et al. | 544/81 |
| 5,194,428 A | 3/1993 | Agrawal et al. | 514/44 |
| 5,217,866 A | 6/1993 | Summerton et al. | 435/6 |

(Continued)

FOREIGN PATENT DOCUMENTS

| | | |
|---|---|---|
| WO | 96/37616 | 11/1996 |
| WO | 98/12312 | 3/1998 |

(Continued)

OTHER PUBLICATIONS

Abe et al., "Inhibition of Influenza Virus Replication by Phosphorothioate and Liposomally Endocapsulated Oligonucleotides," *Nucleosides & Nucleotides* 17(1-3):471-478, 1998.

(Continued)

*Primary Examiner* — Terra Cotta Gibbs
(74) *Attorney, Agent, or Firm* — Seed IP Law Group PLLC

(57) ABSTRACT

The present invention provides antisense antiviral compounds, compositions, and methods of their use and production, mainly for inhibiting the replication of viruses of the Filoviridae family, including Ebola and Marburg viruses. The compounds, compositions, and methods also relate to the treatment of viral infections in mammals including primates by Ebola and Marburg viruses. The antisense antiviral compounds include phosphorodiamidate morpholino oligonucleotides (PMOplus) having a nuclease resistant backbone, about 15-40 nucleotide bases, at least two but typically no more than half piperazine-containing intersubunit linkages, and a targeting sequence that is targeted against the AUG start site region of Ebola virus VP35, Ebola virus VP24, Marburg virus VP24, or Marburg virus NP, including combinations and mixtures thereof.

16 Claims, 27 Drawing Sheets

(56) References Cited

U.S. PATENT DOCUMENTS

| | | | |
|---|---|---|---|
| 5,495,006 A | 2/1996 | Climie et al. | 536/24.1 |
| 5,506,337 A | 4/1996 | Summerton et al. | 528/391 |
| 5,521,063 A | 5/1996 | Summerton et al. | 435/6 |
| 5,576,302 A | 11/1996 | Cook et al. | 514/44 |
| 5,580,767 A | 12/1996 | Cowsert et al. | 435/172.3 |
| 5,698,685 A | 12/1997 | Summerton et al. | 536/24.3 |
| 5,698,695 A | 12/1997 | Appleton et al. | 544/330 |
| 5,702,891 A | 12/1997 | Kolberg et al. | 435/6 |
| 5,734,039 A | 3/1998 | Calabretta et al. | 536/24.5 |
| 5,738,985 A | 4/1998 | Miles et al. | 435/5 |
| 5,749,847 A | 5/1998 | Zewert et al. | 604/49 |
| 5,801,154 A | 9/1998 | Baracchini et al. | 514/44 |
| 5,892,023 A | 4/1999 | Pirotzky et al. | 536/24.5 |
| 5,955,318 A | 9/1999 | Simons et al. | 435/71.1 |
| 5,989,904 A | 11/1999 | Das et al. | 435/320.1 |
| 6,060,456 A | 5/2000 | Arnold, Jr. et al. | 514/44 |
| 6,133,246 A | 10/2000 | McKay et al. | 514/44 |
| 6,174,868 B1 | 1/2001 | Anderson et al. | 514/44 |
| 6,214,555 B1 | 4/2001 | Leushner et al. | 435/6 |
| 6,228,579 B1 | 5/2001 | Zyskind et al. | 435/6 |
| 6,239,265 B1 | 5/2001 | Cook | 536/24.3 |
| 6,258,570 B1 | 7/2001 | Glustein et al. | 435/91.2 |
| 6,306,993 B1 | 10/2001 | Rothbard et al. | 526/304 |
| 6,365,351 B1 | 4/2002 | Iversen | 435/6 |
| 6,365,577 B1 | 4/2002 | Iversen | 514/44 |
| 6,391,542 B1 | 5/2002 | Anderson et al. | 435/6 |
| 6,495,663 B1 | 12/2002 | Rothbard et al. | 530/329 |
| 6,667,152 B2 | 12/2003 | Miles et al. | 435/5 |
| 6,669,651 B1 | 12/2003 | Fukushima et al. | 600/558 |
| 6,669,951 B2 | 12/2003 | Rothbard et al. | 424/436 |
| 6,677,153 B2 | 1/2004 | Iversen | 435/375 |
| 6,784,291 B2 | 8/2004 | Iversen et al. | 536/24.5 |
| 6,828,105 B2 | 12/2004 | Stein et al. | 435/6 |
| 6,841,542 B2 | 1/2005 | Bartelmez et al. | 514/44 |
| 6,841,675 B1 | 1/2005 | Schmidt et al. | 544/336 |
| 6,875,747 B1 | 4/2005 | Iversen et al. | 514/44 |
| 6,881,825 B1 | 4/2005 | Robbins et al. | 530/327 |
| 6,899,864 B2 | 5/2005 | Hnatowich et al. | 424/1.65 |
| 7,049,431 B2 | 5/2006 | Iversen | 536/24.5 |
| 7,094,765 B1 | 8/2006 | Iversen et al. | 514/44 |
| 7,115,374 B2 | 10/2006 | Linnen | 435/6 |
| 7,468,418 B2 | 12/2008 | Iversen et al. | 530/300 |
| 7,507,196 B2 | 3/2009 | Stein et al. | 514/44 |
| 7,524,829 B2 | 4/2009 | Stein et al. | 514/44 |
| 7,582,615 B2 | 9/2009 | Neuman et al. | 514/44 |
| 7,807,801 B2 | 10/2010 | Iversen et al. | 536/22.1 |
| 7,855,283 B2 | 12/2010 | Iversen | 536/24.5 |
| 7,943,762 B2 | 5/2011 | Weller et al. | 536/31 |
| 8,198,429 B2 * | 6/2012 | Iversen et al. | 536/24.5 |
| 2003/0095953 A1 | 5/2003 | Cabot et al. | 424/93.21 |
| 2003/0166588 A1 | 9/2003 | Iversen et al. | 514/44 |
| 2003/0171311 A1 | 9/2003 | Blatt et al. | 514/44 |
| 2003/0171335 A1 | 9/2003 | Stein et al. | 514/81 |
| 2003/0175767 A1 | 9/2003 | Davis et al. | 435/6 |
| 2003/0224353 A1 | 12/2003 | Stein et al. | 435/5 |
| 2004/0072239 A1 | 4/2004 | Renaud et al. | 435/7.1 |
| 2004/0259108 A1 | 12/2004 | Linnen et al. | 435/6 |
| 2005/0171044 A1 | 8/2005 | Stein et al. | 514/44 |
| 2005/0176661 A1 | 8/2005 | Vaillant et al. | 514/44 |
| 2006/0063150 A1 | 3/2006 | Iversen et al. | 435/6 |
| 2006/0149046 A1 | 7/2006 | Arar | 536/23.2 |
| 2006/0269911 A1 | 11/2006 | Iversen et al. | 435/5 |
| 2007/0066556 A1 | 3/2007 | Stein et al. | 514/44 |
| 2007/0129323 A1 | 6/2007 | Stein et al. | 514/44 |
| 2007/0265214 A1 | 11/2007 | Stein et al. | 514/44 |
| 2008/0311556 A1 | 12/2008 | Iversen | 435/5 |
| 2009/0012280 A1 | 1/2009 | Stein et al. | 536/23.1 |
| 2009/0082547 A1 | 3/2009 | Iversen et al. | 530/322 |
| 2009/0088562 A1 | 4/2009 | Weller et al. | 536/24.5 |
| 2009/0099066 A1 | 4/2009 | Moulton et al. | 514/7 |
| 2009/0186847 A1 | 7/2009 | Stein et al. | 514/44 |
| 2009/0186848 A1 | 7/2009 | Stein et al. | 514/44 |
| 2009/0186849 A1 | 7/2009 | Stein et al. | 514/44 |
| 2010/0016215 A1 | 1/2010 | Moulton et al. | 514/7 |
| 2010/0292189 A1 | 11/2010 | Iversen et al. | 514/81 |
| 2011/0118334 A1 | 5/2011 | Iversen | 514/44 |

FOREIGN PATENT DOCUMENTS

| | | |
|---|---|---|
| WO | 99/32147 | 7/1999 |
| WO | 00/00617 | 1/2000 |
| WO | 01/49775 | 7/2001 |
| WO | 02/26968 | 4/2002 |
| WO | 02/068637 | 9/2002 |
| WO | 03/033657 | 4/2003 |
| WO | 2005/007805 | 1/2005 |
| WO | 2005/013905 | 2/2005 |
| WO | 2005/030800 | 4/2005 |
| WO | 2005/065268 | 7/2005 |
| WO | 2006/033933 | 3/2006 |
| WO | 2006/047683 | 5/2006 |
| WO | 2006/050414 | 5/2006 |
| WO | 2007/030576 | 3/2007 |
| WO | 2007/030691 | 3/2007 |
| WO | 2007/103529 | 9/2007 |
| WO | 2011/060320 | 5/2011 |

OTHER PUBLICATIONS

Agrawal et al., "Antisense therapeutics: is it as simple as complementary base recognition?," *Molecular Medicine Today* 6:72-81, 2000.

Agrawal et al., "Oligodeoxynucleoside phosphoramidates and phosphorothioates as inhibitors of human immunodeficiency virus," *Proc. Natl. Acad. Sci. USA* 85:7079-7083, 1988.

Agrawal et al., "Site-specific excision from RNA by RNase H and mixed-phosphate-backbone oligodeoxynucleotides," *Proc. Natl. Acad. Sci. USA* 87:1401-1405, 1990.

Amantana et al., "Pharmacokinetics, Biodistribution, Stability and Toxicity of a Cell-Penetrating Peptide—Morpholino Oligomer Conjugate," *Bioconjugate Chem.* 18:1325-1331, 2007.

Arora et al., "Redirection of drug metabolism using antisense technology," *Curr. Opin. Mol. Ther.*, 3(3):249-257, 2001.

Bailey et al., "Cationic oligonucleotides can mediate specific inhibition of gene expression in *Xenopus* oocytes," *Nucleic Acids Research* 26(21):4860-4867, 1998.

Banerjee et al., "Interaction of picornavirus 2C polypeptide with the viral negative-strand RNA," *Journal of General Virology* 82:2621-2627, 2001.

Banerjee et al., "Interaction of Poliovirus-Encoded 2C/2BC Polypeptides with the 3' Terminus Negative-Strand Cloverleaf Requires an Intact Stem-Loop b," *Virology* 280:41-51, 2001.

Banerjee et al., "Poliovirus-Encoded 2C Polypeptide Specifically Binds to the 3'-Terminal Sequences of Viral Negative-Strand RNA," *Journal of Virology* 71(12):9570-9578, 1997.

Banerjee et al., "Specific Interaction of Hepatitis C Virus Protease/Helicase NS3 with the 3'-Terminal Sequences of Viral Positive- and Negative-Strand RNA," *Journal of Virology* 75(4):1708-1721, 2001.

Barawkar et al., "Synthesis, biophysical properties, and nuclease resistance properties of mixed backbone oligodeoxynucleotides containing cationic internucleoside guanidinium linkages: Deoxynucleic guanidine/DNA chimeras," *Proc. Natl. Acad. Sci. USA* 95:11047-11052, 1998.

Basler et al., "The Ebola virus VP35 protein functions as a type I IFN antagonist," *PNAS* 97(22):12289-12294, 2000.

Blommers et al., "An approach to the structure determination of nucleic acid analogues hybridized to RNA. NMR studies of a duplex between 2'-OMe RNA and an oligonucleotide containing a single amide backbone modification," *Nucleic Acids Res.*, 22(20):4187-94, 1994.

Bonham et al., "An assessment of the antisense properties of RNase H-competent and steric-blocking oligomers," *Nucleic Acids Res.*, 23(7): 1197-203, 1995.

Borio et al., "Hemorrhagic Fever Viruses as Biological Weapons: Medical and Public Health Management," *JAMA* 287(18):2391-2405, 2002.

Boudvillain et al., "Transplatin-modified oligo(2'-O-methyl ribonucleotide)s: a new tool for selective modulation of gene expression," *Biochemisty*, 36(10): 2925-31, 1997.

Branch, "A good antisense molecule is hard to find," *TIBS* 23:45-50, 1998.
Brasey et al., "The Leader of Human Immunodeficiency Virus Type 1 Genomic RNA Harbors an Internal Ribosome Entry Segment That Is Active During the $G_2$/M Phase of the Cell Cycle," *Journal of Virology* 77(7):3939-3949, 2003.
Bray et al., "A Mouse Model for Evaluation of Prophylaxis and Therapy of Ebola hemorrhagic Fever," *The Journal of Infectious Diseases* 178:651-661, 1998.
Burnett et al., "The Evolving Field of Biodefence: Therapeutic Developments and Diagnostics," *Natural Reviews|Drug Discovery* 4:281-297, 2005.
Callahan et al., "Molecular cloning and complete sequence determination of RNA genome of human rhinovirus type 14," *Proc. Natl. Acad. Sci. USA* 82:732-736, 1985.
Chirila et al., "The use of synthetic polymers for delivery of therapeutic antisense oligodeoxynucleotides," *Biomaterials*, 23:321-342, 2002.
Clarke et al., "Organization and Expression of *Calicivirus* Genes," *Journal of Infectious Diseases* 181(Suppl. 2):S309-S316, 2000.
Connolly et al., "Pathogenesis of Experimental Ebola Virus Infection in Guinea Pigs," *The Journal of Infectious Diseases* 179(Suppl. 1):S203-S217, 1999.
Corey et al., "Morpholino antisense oligonucleotides: tools for investigating vertebrate development," *Genome Biology* 2(5):reviews 1015.1-1015.3, 2001.
Cox et al., "Global Epidemiology of Influenza: Past and Present," *Annu. Rev. Med.* 51:407-421, 2000.
Cox et al., "Influenza," *The Lancet* 354:1277-1282, 1999.
Crooke et al., "In Vitro Toxicological Evaluation of ISIS 1082, a Phosphorothioate Oligonucleotide Inhibitor of Herpes Simplex Virus," *Antimicrobial Agents and Chemotherapy* 36(3):527-532, 1992.
Crooke, *Antisense Research and Application*, CRC Press, New York, 1999, Chap. 1, "Basic Principles of Antisense Therapeutics," pp. 1-50.
Cross et al., "Solution structure of an RNA x DNA hybrid duplex containing a 3'-thioformacetal linker and an RNA A-tract," *Biochemistry*, 36: 4096-107, 1997.
Dagle et al., "Targeted elimination of zygotic messages in *Xenopus laevis* embryos by modified oligonucleotides possessing terminal cationic linkages," *Nucleic Acids Research* 28(10):2153-2157, 2000.
Deas et al., "Inhibition of Flavivirus Infections by Antisense Oligomers Specifically Suppressing Viral Translation and RNA Replication," *Journal of Virology* 79(8):4599-4609, 2005.
Ding, D. et al., "An oligodeoxyribonucleotide N3'→P5' phosphoramidate duplex forms an A-type helix in solution," *Nucleic Acids, Res.*, 24(2): 354-60, 1996.
Dwight D. Weller et al., U.S. Appl. No. 13/049,770, filed Mar. 16, 2011, 167 pages.
Egholm, et al., "PNA hybridizes to complementary oligonucleotides obeying the Watson-Crick hydrogen-bonding rules," *Nature*, 365:566-8, 1993.
European Search Report for EPAN 05796604.6, dated Jan. 5, 2009, 7 pages.
Faria et al., "Phosphoramidate olionucleotides as potent antisense molecules in cells and in vivo," *Nature Biotechnology* 19:40-44, 2001.
Feldmann et al., "Classification, Structure, and Replication of Filoviruses," *Curr. Top. Microbiol. Immunol.* 235:1-21, 1999.
Feldmann et al., "EBOLA virus: from discovery to vaccine," *Nature Reviews* 3(8):677-685, 2003.
Feldmann et al., "Molecular biology and evolution of filoviruses," *Arch. Virol.* 7(Suppl.):81-100, 1993.
Feigner, et al., "Lipofection: a highly efficient, lipid-mediated DNA-transfection procedure" *Proc Natl Acad Sci USA*, 84S: 7413-7, 1987.
Fischer, "Cellular Uptake Mechanisms and Potential Therapeutic Utility of Peptidic Cell Delivery Vectors: Progress 2001-2006," *Medicinal Research Reviews* 27(6):755-795, 2007.
Fowler et al, "Inhibition of Marburg virus protein expression and viral release by RNA interference," *Journal of General Virology* 86:1181-1188, 2005.

Freier, Crooke (ed.), *Antisense Drug Technology: Principles, Strategies, and Applications*, CRC Press, New York, 1999, Chap. 5, "Methods of Selecting Sites in RNA for Antisense Targeting," pp. 107-118.
Gait, et al., "Synthetic-analogues of polynucleotides Part XII. Synthesis of thymidine derivatives containing an oxyacetamido- or an oxyformamido-linkage instead of a phosphodiester group," *J. Chem Soc* [Perkin 1]: 1684-6, 1974.
Gee et al., "Assessment of high-affinity hybridization, RNase H cleavage, and covalent linkage in translation arrest by antisense oligonucleotides," *Antisense Nucleic Acid Drug Dev.*, 8: 103-11, 1998.
Geisbert et al., "Ebola virus: new insights into disease aetiopathology and possible therapeutic interventions," *Expert Reviews in Molecular Medicine* 6(20):1-24, 2004.
Geisbert et al., "Treatment of Ebola virus infection with a recombinant inhibitor of factor VIIa/tissue factor: a study in rhesus monkeys," *The Lancet*, 362:1953-58, 2003.
Geisbert et al., "Postexposure protection of non-human primates against a lethal Ebola virus challenge with RNA interference: a proof-of-concept study," *Lancet* 375:1896-1905, 2010.
Genbank Accession No. AF029248, 2000.
GenBank Accession No. AF086833, 2005.
Genbank Accession No. AF091736, 2000.
Genbank Accession No. AF169005, 2007.
Genbank Accession No. AF304460, 2001.
GenBank Accession No. AF522874, 2002.
Genbank Accession No. AY274119, 2004.
Genbank Accession No. NC_002645, 2006.
GenBank Accession No. Z29337, 2006.
Gilbert et al., "Sieve analysis: methods for assessing from vaccine trial data how vaccine efficacy varies with genotypic and phenotypic pathogen variation," *Journal of Clinical Epidemiology* 54(1):68-85, 2001.
Green et al., "Antisense Oligonucleotides: An Evolving Technology for the Modulation of Gene Expression in Human Disease," *J. Am. Coll. Surg.* 191:93-105, 2000.
Hanecak et al., "Antisense Oligonucleotide Inhibition of Hepatitis C Virus Gene Expression in Transformed Hepatocytes," *Journal of Virology* 70(8):5203-5212, 1996.
Holland, Morse (ed.), *Emerging Viruses*, Oxford University Press US, New York, 1993, Chap. 19, "Replication Error, Quasispecies Populations, and Extreme Evolution Rates of RNA Viruses," pp. 203-218.
Hudziak et al., "Resistance of Morpholino Phosphorodiamidate Oligomers to Enzymatic Degradation," *Antisense & Nucleic Acid Drug Development* 6:267-272, 1996.
International Search Report and Written Opinion for PCT/US2007/011435, dated Sep. 29, 2008, 5 pages.
International Search Report, mailed Aug. 29, 2007, for PCT/US05/39607, 4 pages.
International Search Report, mailed Oct. 31, 2011, for PCT/US2010/046234.
Written Opinion for International Application No. PCT/US2010/046234, mailed Oct. 31, 2011.
Iversen et al., "Antisense Antiviral Compound and Method for Treating ssRNA Viral Infection," Office Action mailed Oct. 19, 2010, for U.S. Appl. No. 11/432,031, 25 pages.
Jaeger et al., "Improved predictions of secondary structures for RNA," *Proc. Natl. Sci. USA* 86:7706-7710, 1989.
Jahrling et al., "Evaluation of immune globulin and recombinant interferon-alpha2b for treatment of experimental Ebola virus infections," *J. Infect. Dis.*, 179(Suppl. 1):S224-S234, 1999.
Jen et al., "Suppression of Gene Expression by Targeted Disruption of Messenger RNA: Available Options and Current Strategies," *Stem Cells* 18:307-319, 2000.
Johannes et al., "Identification of eukaryotic mRNAs that are translated at reduced cap binding complex eIF4F concentrations using a cDNA microarray." *PNAS* 96(23):13118-13123, 1999.
Jubin et al., "Hepatitis C Virus Internal Ribosome Entry Site (IRES) Stem Loop IIId Contains a Phylogenetically Conserved GGG Triplet Essential for Translation and IRES Folding," *Journal of Virology* 74(22):10430-10437, 2000.

Kinney et al, "Inhibition of dengue virus serotypes 1 to 4 in vero cell cultures with morpholino oligomers," *Journal of Virology* 79(8):5116-5128, 2005.

Lee et al., "Complete sequence of the RNA genome of human rhinovirus 16, a clinically useful common cold virus belonging to the ICAM-1 receptor group," *Virus Genes* 9(2):177-184, 1994.

Lesnikowski, et al., "Octa(thymidine methanephosphonates) of partially defined stereochemistry: synthesis and effect of chirality at phosphorus on binding to pentadecadeoxyriboadenylic acid," *Nucleic Acids Res.*, 18(8): 2109-15, 1990.

Linkletter et al., "Solid-phase synthesis of positively charged deoxynucleic guanidine (DNG) modified oligonucleotides containing neutral urea linkages: Effect of charge deletions on binding and fidelity," *Bioorg. Med. Chem.* 8(11):1893-1901, 2000.

Liu et al., "Structural and functional analysis of the 5' untranslated region of coxsackievirus B3 RNA: In vivo translational and infectivity studies of full-length mutants," *Virology* 265:206-217, 1999.

Lopez De Quinto et al., "Involvement of the aphthovirus RNA region located between the two functional AUGs in start codon selection," *Virology* 255(2):324-336, 1999.

Markoff, "5'- and 3'-noncoding regions in flavivirus RNA," *Adv. Virus Res.* 59:177-228, 2003.

McCaffrey et al., "A Potent and Specific Morpholino Antisense Inhibitor of Hepatitis C Translation in Mice," *Hepatology* 38:503-508, 2003.

Mertes, et al., "Synthesis of carbonate analogs of dinucleosides. 3'-Thymidinyl 5'-thymidinyl carbonate, 3'-thymidinyl 5'-(5-fluoro-2'-deoxyuridinyl) carbonate, and 3'-(5-fluoro-2'-deoxyuridinyl) 5'-thymidinyl carbonate," *J Med Chem.*, 12: 154-7, 1969.

Micklefield, "Backbone Modification of Nucleic Acids: Synthesis, Structure, and Therapeutic Applications," *Current Medicinal Chemistry* 8:1157-1179, 2001.

Miranda et al., "Differential activation of apoptosis regulatory pathways during monocytic vs granulocytic differentiation: a requirement for Bcl-$X_L$ and XIAP in the prolonged survival of monocytic cells," *Leukemia* 17(2):390-400, 2003.

Mizuta et al., "Antisense oligonucleotides directed against the viral RNA polymerase gene enhance survival of mice infected with influenza A," *Nature Biotechnology* 17:583-587, 1999.

Moulton et al., "Cellular Uptake of Antisense Morpholino Oligomers Conjugated to Arginine-Rich Peptides," *Bioconjugate Chemistry* 15:290-299, 2004.

Moulton et al., "Abstracts of Papers: Part 1, Delivery of Antisense Phosphorodiamidate Morpholino Oligomers by Arginine-Rich Peptides", in *Proceedings of the 226th ACS National Meeting*, Biol., American Chemical Society, New York, NY, Sep. 7-11, 2003.

National Center for Biotechnology Information Report No. AF029248 from NCBI Genome Database (2000).

National Center for Biotechnology Information Report No. NC_002645 from NCBI Genome Database (2006).

National Center for Biotechnology Information Report No. AY274119 from NCBI Genome Database (2004).

NCBI Genbank Nucleotide Accession No. AF091736, VESV-like calicivirus strain Pan-1, complete genome, 5 pages, 2000.

NCBI Genbank Nucleotide Accession No. AF169005, Hepatitis C virus subtype 2a isolate NDM59, complete genome, 5 pages, 2007.

Nelson et al., "Arginine-Rich Peptide Conjugation to Morpholino Oligomers: Effects on Antisense Activity and Specificity," *Bioconjugate Chemistry* 16:959-966, 2005.

Neuman et al., "Antisense Morpholino-Oligomers Directed Against the 5' end of the Genome Inhibit Coronavirus Proliferation and Growth," *Journal of Virology* 78(11):5891-5899, 2004.

Orr et al., "Patent review: Therapeutic applications for antisense oligonucleotides 1999-2000" *Current Opinion in Molecular Therapeutics* 2(3):325-331, 2000.

O'Ryan et al., Specter et al. (eds.), *Clinical Virology Manual*, Elsevier, New York, 1992, Chapter 22, "Rotavirus, Enteric, Adenoviruses, Norwalk Virus, and Other Gastroenteritis Tract Viruses," pp. 361-396.

Palù et al. "In pursuit of new developments for gene therapy of human diseases," *Journal of Biotechnology* 68:1-13, 1999.

Pardigon et al., "Cellular Proteins Bind to the 3' End of Sindbis Virus Minus-Strand RNA," *Journal of Virology* 66(2):1007-1015, 1992.

Pardigon et al., "Multiple Binding Sites for Cellular Proteins in the 3' End of Sindbis Alphavirus Minus-Sense RNA," *Journal of Virology* 67(8):5003-5011, 1993.

Partridge et al., "A Simple Method for Delivering Morpholino Antisense Oligos into the Cytoplasm of Cells," *Antisense & Nucleic Acid Drug Dev.* 6:169-175, 1996.

Paul, Semler et al. (eds.), *Molecular Biology of Picornaviruses*, ASM Press, Wastington, DC, 2002, Chap. 19, "Possible Unifying Mechanism of Picornavirus Genome Replication," pp. 227-246.

Peters et al., "An introduction to Ebola: the virus and the disease," *Journal of Infectious Diseases*, 179(Suppl. 1):ix-xvi, 1999.

Raviprakash et al, "Inhibition of Dengue Virus by Novel, Modified Antisense Oligonucleotides," *Journal of Virology* 69(1):69-74, 1995.

Robaczewska, et al, "Inhibition of hepadnaviral replication by polyethylenimine-based intravenous delivery of antisense phosphodiester oligodeoxynucleotides to the liver," *Gene Therapy*, 8: 874-881, 2001.

Roehl et al., "Poliovirus Infection Enhances the Formation of Two Ribonucleoprotein Complexes at the 3' End of Viral Negative-Strand RNA," *Journal of Virology* 69(5):2954-2961, 1995.

Roehl et al., "Processing of a Cellular Polypeptide by 3CD Proteinase is Required for Poliovirus Ribonucleoprotein Complex Formation," *Journal of Virology* 71(1):578-585, 1997.

Rothbard et al., "Arginine-Rich molecular Transporters for Drug Delivery: Role of Backbone Spacing in Cellular Uptake," *J. Med. Chem.* 45:3612-3618, 2002.

Sanchez et al., "Sequence analysis of the Ebola virus genome: organization, genetic elements, and comparison with the genome of Marburg virus," *Virus Research* 29:215-240, 1993.

Sanchez et al., "Variation in the Glycoprotein and VP35 Genes of Marburg Virus Strains," *Virology* 240:138-146, 1998.

Sankar et al., "Antisense oligonucleotide inhibiton of encephalomyocarditis virus RNA translation," *Eur. J. Biochem.* 184:39-45, 1989.

Scanlon, "Anti-Genes: siRNA, Ribozymes and Antisense," *Current Pharmaceutical Biotechnology* 5:415-420, 2004.

Shabbits et al., "Tumor Chemosensitization Strategies Based on Apoptosis Manipulations," *Molecular Cancer Therapeutics* 2:805-813, 2003.

Shengqi et al., "Synthesis of Antisense Phosphothioate Oligodeoxynucleotides of Dengue Fever Virus and Their Anti-Viral Activity," *Progress in Biochemistry and Biophysics* 24:64-68, 1997 (English Translation).

Siprashvili et al., "Gene transfer via reversible plasmid condensation with cysteine-flanked, internally spaced arginine-rich peptides," *Human Gene Therapy* 14:1225-1233, 2003.

Smith et al., "Antisense treatment of *caliciviridae*: an emerging disease agent of animals and humans," *Current Opinion Molecular Therapeutics* 4(2):177-184, 2002.

Smith et al., "Calicivirus Emergence from Ocean Reservoirs: Zoonotic and Interspecies Movements," *Emerging Infectious Diseases* 4(1):13-20, 1998.

Smith et al., "Secondary structure and hybridization accessibility of the hepatitis C virus negative strand RNA 5'-terminus," *Journal of Viral Hepatitis* 11:115-123, 2004.

Sosnovtsev et al., "RNA Transcripts Derived from a Cloned Full-Legnth Copy of the Feline Calicivirus Genome Do Not Require VpG for Infectivity," *Virology* 210:383-390, 1995.

Spurgers et al., "Oligonucleotide antiviral therapeutics: Antisense and RNA interference for highly pathogenic RNA viruses," *Antiviral Research* 78:26-36, 2008.

Stein et al., "A Specificity Comparison of Four Antisense Types: Morpholino, 2'-O-Methyl RNA, DNA, and Phosphorothioate DNA," *Antisense & Nucleic Acid Drug Development* 7:151-157, 1997.

Stein et al., "Antisense Antiviral Agent and Method for Treating ssRNA Viral Infection," Office Action mailed Feb. 17, 2010, for U.S. Appl. No. 11/431,968, 19 pages.

Stein et al, "Inhibition of Vesivirus Infections in Mammalian Tissue Culture with Antisense Morpholino Oligomers," *Antisense & Nucleic Acid Drug Development* 11:317-325, 2001.

Summerton et al., "Morpholino and Phosphorothioate Antisense Oligomers Compared in Cell-Free and In-Cell Systems," *Antisense & Nucleic Acid Drug Development* 7:63-70, 1997.

Summerton, "Morpholino antisense oligomers: the case for an RNase H-independent structural type," *Biochimica et Biophysica Acta* 1489:141-158, 1999.

Summerton et al., "Morpholino Antisense Oligomers: Design, Preparation, and Properties," *Antisense & Nucleic Acid Drug Development* 7(3):187-195, 1997.

Swenson et al., "Chemical Modifications of Antisense Morpholino Oligomers Enhance Their Efficacy against Ebola Virus Infection," Antimicrobial Agents and Chemotherapy 53(5):2089-2099, 2009.

Taylor et al., "Antisense oligonucleotides: a systematic high-throughput approach to target validation and gene function determination," *DDT* 4(12):562-567, 1999.

Thiel et al., "Infectious RNA transcribed in vitro from a cDNA copy of the human coronavirus genome cloned in vaccinia virus," *Journal of General Virology* 82:1273-1281, 2001.

Toulme et al., "Targeting RNA structures by antisense oligonucleotides," *Biochimie* 78:663-673, 1996.

Vanderzanden et al., "DNA Vaccines Expressing either the GP or NP Genes of Ebola Virus Protect Mice from Lethal Challenge," *Virology* 246:134-144, 1998.

Vlassov et al., "Inhibition of the Influenza Virus M Protein mRNA Translation in vitro with Complementary Oligonucleotides," *Nucleosides & Nucleotides* 10(1-3):649-650, 1991.

Wages et al., "Affinity Purification of RNA: Sequence-Specific Capture by Nonionic Morpholino Probes," *BioTechniques* 23:1116-1121, 1997.

Wang et al., "Specific Inhibition of Coxsackievirus B3 Translation and Replication by Phosphorothioate Antisense Oligodeoxynucleotides," *Antimicrobial Agents Chemotherapy* 45(4):1043-1052, 2001.

Warfield et al., "Development of a Phosphorodiamidate Morpholino Oligomer Antisense to Ebola Zaire," in *Proceedings of the 18th International Conference on Antiviral Research*, vol. 65, No. 3, Barcelona, Spain, Apr. 11-14, 2005, pp. A45 (abstract #35).

Warfield et al., "Role of Natural Killer Cells in Innate Protection Against Lethal Ebola Virus Infection," *The Journal of Experimental Medicine* 200(2:)169-179, 2004.

Warfield et al., "Gene-Specific Countermeasures against Ebola Virus Based on Antisense Phosphorodiamidate Morpholino Oligomers," *PLoS Pathogens* 2(1): 5-13, 2006.

Warren et al., "Advanced antisense therapies for postexposure protection against lethal filovirus infections," *Nature Medicine* 16(9), pp. 991-994, 2010.

Wei et al., "Human immunodeficiency virus type-1 reverse transcription can be inhibited in vitro by oligonucleotides that target both natural and synthetic tRNA primers," *Nucleic Acids Research* 28(16):3065-3074, 2000.

Williams et al., "A Single Intra-articular Injection of Liposomally Conjugated Methotrexate Suppresses Joint Inflammation in Rat Antigen-Induced Arthritis," *British Journal of Rheumatology* 35:719-724, 1996.

Wilson et al., "Naturally occurring dicistronic cricket paralysis virus RNA is regulated by two internal ribosome entry sites," *Mol. Cell. Biol.*, 20(14): 4990-4999, 2000.

Written Opinion for International Application No. PCT/US05/39607, mailed Aug. 29, 2007, 6 pages.

Winter et al., "Nucleotide Sequence of Human Influenza A/PR/8/34 Segment 2," *Nucleic Acids Research*, 10(6): 2135-2143, 1982.

Wu et al., "Specific Inhibition of Hepatitis B Viral Gene Expression in vitro by Targeted Antisense Oligonucleotides," *The Journal of Biological Chemistry* 267(18):12436-12439, 1992.

Wu et al., "Receptor-mediated in vitro gene transformation by a soluble DNA carrier system," *J. Biol. Chem.*, 262(10): 4429-4432, 1987.

Xu et al., "Immunization for Ebola virus infection," *Nature Medicine* 4(1):37-42, 1998.

Xu et al., "Viral haemorrhagic disease of rabbits in the People's Republic of China: epidemiology and virus characterization," *Rev. sci. tech. Off. int. Epiz.* 10(2):393-408, 1991.

Yuan et al., "A phosphorothioate antisense oligodeoxynucleotide specifically inhibits coxsackievirus B3 replication in cardiomyocytes and mouse hearts," *Laboratory Investigation* 84:703-714, 2004.

Zhang et al., "Antisense Oligonucleotide Inhibition of Hepatitis C Virus (HCV) Gene Expression in Livers of Mice Infected with an HCV-Vaccinia Virus Recombinant," *Antimicrobial Agents and Chemotherapy* 43(2):347-353, 1999.

Zollinger et al., "Meningococcal vaccines—present and future," *Transactions of Royal Society of Tropical Medicine and Hygiene* 85(Supp. 1):37-43, 1991.

Zuker, "Mfold web server for nucleic acid folding and hybridization prediction," *Nucleic Acids Research* 31(13):3406-3415, 2003.

\* cited by examiner

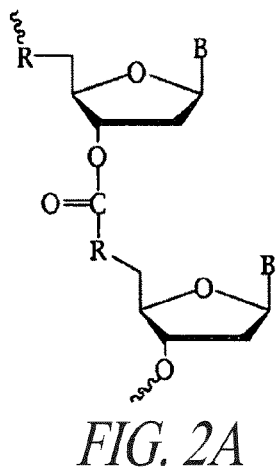
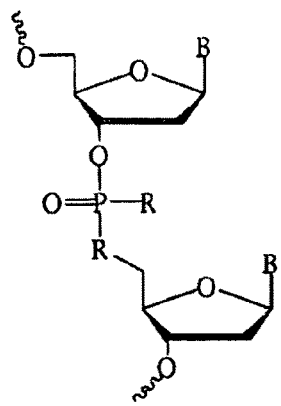
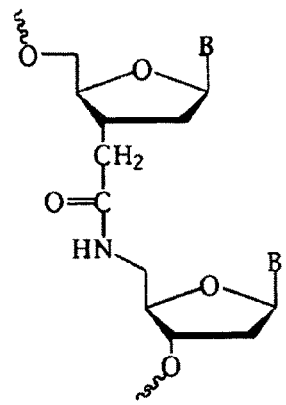
FIG. 2A　　　　　FIG. 2B　　　　　FIG. 2C
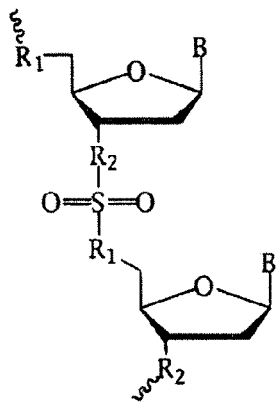
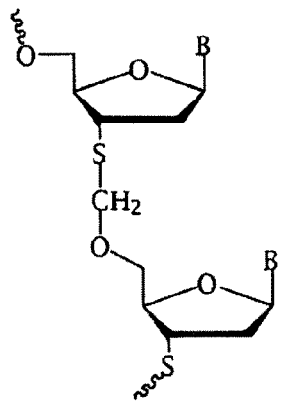
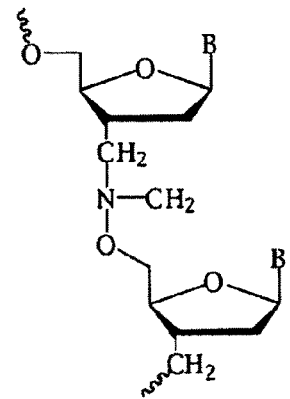
FIG. 2D　　　　　FIG. 2E　　　　　FIG. 2F
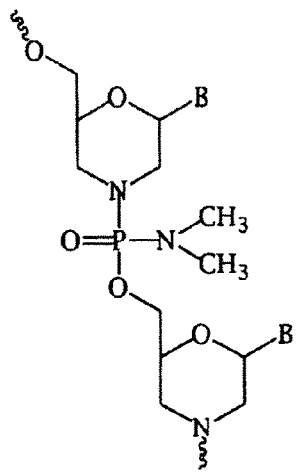
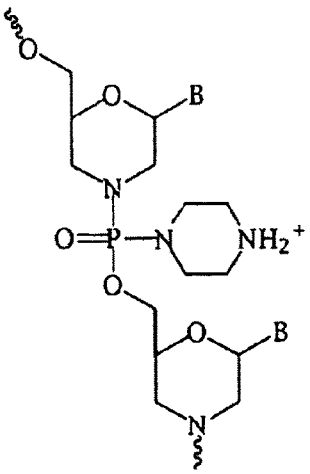
FIG. 2G　　　　　FIG. 2H

FIG. 4A pCN → gatgaagatttaaaaccttcatc (SEQ ID NO:81) ......... aggaaaagctggtctaacaagATGacaactagaacaaagggcagg (SEQ ID NO:82) ..... → luciferase Regions marked: ⑤, ③, ④, ②, ①, ⑥

FIG. 4B

| PMO | Sequence |
|---|---|
| 1) PMO 0-1-63-542 (EBOLA-VP35-16) (SEQ ID NO:25) | 5' – GTC ATC TTG TTA GAC C – 3' |
| 2) PMO 0-1-63-540 (EBOLA-VP35-19) (SEQ ID NO:24) | 5' – GTC ATC TTG TTA GAC CAG C – 3' |
| 3) PMO 0-1-63-413 (3136-3115(+)) (SEQ ID NO:21) | 5' – GTT GTC ATC TTG TTA GAC CAG C – 3' |
| 4) PMO 0-1-63-310 (3136-3115(+)-P003) (SEQ ID NO:21) | 5' – GTT GTC GAA GGT TTT TGT TCT AGT TG – 3' |
| 5) PMO 0-1-63-565 (EBV VP35 5' Term.) (SEQ ID NO:23) | 5' – GAT GAA GGT TTT TGT TCT AGT TG – 3' |
| 6) PMO 0-1-63-539 (EBOLA-VP35') (SEQ ID NO:22) | 5' – CCT GCC CTT TGT TCT AGT TG – 3' |

SEQUENCE LISTING

<160> NUMBER OF SEQ ID NOS: 82

<210> SEQ ID NO 1
<211> LENGTH: 125
<212> TYPE: RNA
<213> ORGANISM: Zaire ebolavirus

<400> SEQUENCE: 1
aaugaugaag auuaaaaccu ucaucauccu uacgucaauu gaauucucua gcacucgaag    60

-continued

```
cuuauugucu ucaauguaaa agaaaagcug gucuaacaag augacaacua gaacaaaggg      120
caggg                                                                  125

<210> SEQ ID NO 2
<211> LENGTH: 125
<212> TYPE: RNA
<213> ORGANISM: Zaire ebolavirus

<400> SEQUENCE: 2
cguuccaaca aucgagcgca agguuucaag guugaacuga gagugucuag acaacaaaau       60
auugauacuc cagacaccaa gcaagaccug agaaaaaacc auggcuaaag cuacgggacg      120
auaca                                                                  125

<210> SEQ ID NO 3
<211> LENGTH: 125
<212> TYPE: RNA
<213> ORGANISM: Zaire ebolavirus

<400> SEQUENCE: 3
agaucugcga accgguagag uuuaguugca accuaacaca cauaaagcau uggucaaaaa       60
gucaauagaa auuuaaacag ugaguggaga caacuuuuaa auggaagcuu cauaugagag      120
aggac                                                                  125

<210> SEQ ID NO 4
<211> LENGTH: 125
<212> TYPE: RNA
<213> ORGANISM: Zaire ebolavirus

<400> SEQUENCE: 4
aaaccaaaag ugaugaagau uaagaaaaac cuaccucggc ugagagagug uuuuuucauu       60
aaccuucauc uuguaaacgu ugagcaaaau uguuaaaaau augaggcggg uuauauugcc      120
uacug                                                                  125

<210> SEQ ID NO 5
<211> LENGTH: 124
<212> TYPE: RNA
<213> ORGANISM: Zaire ebolavirus

<400> SEQUENCE: 5
guagauuaag aaaaaagccu gaggaagauu aagaaaaacu gcuuauuggg ucuuuccgug       60
uuuuagauga agcaguugaa auucuuccuc uugauauuaa auggcuacac aacauaccca      120
auac                                                                   124

<210> SEQ ID NO 6
<211> LENGTH: 125
<212> TYPE: RNA
<213> ORGANISM: Zaire ebolavirus

<400> SEQUENCE: 6
ugaacacuua ggggauugaa gauucaacaa cccuaaagcu uggguaaaa cauuggaaau        60 aguuaaaaga caaauugcuc ggaaucacaa aauuccgagu auggauucuc guccucagaa      120
aaucu                                                                  125

<210> SEQ ID NO 7
<211> LENGTH: 30
<212> TYPE: RNA
<213> ORGANISM: Zaire ebolavirus
```

```
<400> SEQUENCE: 7
uaaaaauucu ucuuucuuuu uguguguccg                              30

<210> SEQ ID NO 8
<211> LENGTH: 125
<212> TYPE: RNA
<213> ORGANISM: Lake victoria marburgvirus

<400> SEQUENCE: 8
cuaaaaaucg aagaauauua aagguuuucu uuaauauuca gaaaagguuu uuuauucucu   60
ucuuucuuuu ugcaaacaua uugaaauaau aauuuucaca auggggacu caucauauau   120 gcaac                                                             125

<210> SEQ ID NO 9
<211> LENGTH: 125
<212> TYPE: RNA
<213> ORGANISM: Lake victoria marburgvirus

<400> SEQUENCE: 9
uucauucaaa caccccaaau uuucaaucau acacauaaua accauuuuag uagcguuacc   60
uuucaauaca aucaggura uuguguaaaag acuuccaaac auggcagaau uaucaacgcg  120
uuaca                                                             125

<210> SEQ ID NO 10
<211> LENGTH: 124
<212> TYPE: RNA
<213> ORGANISM: Lake victoria marburgvirus

<400> SEQUENCE: 10
gaagaacauu aaguguucuu uguuagaauu auucauccaa guuguuuga guauacucgc   60 uucaauacaa cuucccuuca uauuugauuc aagauuuaaa augcaacaac cccgruggaag  120 gagu                                                              124

<210> SEQ ID NO 11
<211> LENGTH: 125
<212> TYPE: RNA
<213> ORGANISM: Lake victoria marburgvirus

<400> SEQUENCE: 11
ucccaaucuc agcuuguuga auuaauuguu acuuaaguca uucuuuuuaa aauuaauuca   60
cacaagguag uuugggruuua uaucuagaac aaauuuuaau auggccagru ccagcaauua  120
caaca                                                             125

<210> SEQ ID NO 12
<211> LENGTH: 125
<212> TYPE: RNA
<213> ORGANISM: Lake victoria marburgvirus

<400> SEQUENCE: 12
ucauucucuu cgauacacgu uauaucuuua gcaaaguaau gaaaauagcc uugucauguu   60
agacgccagu uaccaucuu aagugaaucc uuucuucaau augcagcauc caacucaaua  120
uccug                                                             125

<210> SEQ ID NO 13
<211> LENGTH: 125
<212> TYPE: RNA
<213> ORGANISM: Lake victoria marburgvirus
```

```
-continued

<400> SEQUENCE: 13
cacacaaaaa caagagauga ugauuuugug uaucauauaa auaaagaaga auauuaacau    60
ugacauugag acuugucagu cuguuaauau ucuugaaaag auggauuuac auagcuuguu   120
agagu                                                              125

<210> SEQ ID NO 14
<211> LENGTH: 30
<212> TYPE: RNA
<213> ORGANISM: Lake victoria marburgvirus

<400> SEQUENCE: 14
caaaaucauc aucucuuguu uuugugugguc                                   30

<210> SEQ ID NO 15
<211> LENGTH: 22
<212> TYPE: DNA
<213> ORGANISM: Artificial sequence
<220> FEATURE:
<223> OTHER INFORMATION: Synthetic oligomer

<400> SEQUENCE: 15
cggacacaca aaagaaaga ag                                             22

<210> SEQ ID NO 16
<211> LENGTH: 22
<212> TYPE: DNA
<213> ORGANISM: Artificial sequence
<220> FEATURE:
<223> OTHER INFORMATION: Synthetic oligomer

<400> SEQUENCE: 16
gtagccattt aatatcaaga gg                                            22

<210> SEQ ID NO 17
<211> LENGTH: 20
<212> TYPE: DNA
<213> ORGANISM: Artificial sequence
<220> FEATURE:
<223> OTHER INFORMATION: Synthetic oligomer

<400> SEQUENCE: 17
tgggtatgtt gtgtagccat                                               20

<210> SEQ ID NO 18
<211> LENGTH: 22
<212> TYPE: DNA
<213> ORGANISM: Artificial sequence
<220> FEATURE:
<223> OTHER INFORMATION: Synthetic oligomer

<400> SEQUENCE: 18
caagaggaag aatttcaact gc                                            22

<210> SEQ ID NO 19
<211> LENGTH: 21
<212> TYPE: DNA
<213> ORGANISM: Artificial sequence
<220> FEATURE:
<223> OTHER INFORMATION: Synthetic oligomer

<400> SEQUENCE: 19
gtattgggta tgttgtgtag c                                             21

<210> SEQ ID NO 20
```

-continued

```
<211> LENGTH: 21
<212> TYPE: DNA
<213> ORGANISM: Artificial sequence
<220> FEATURE:
<223> OTHER INFORMATION: Synthetic oligomer

<400> SEQUENCE: 20
cgtctgggta ttgggtatgt t                                            21

<210> SEQ ID NO 21
<211> LENGTH: 22
<212> TYPE: DNA
<213> ORGANISM: Artificial sequence
<220> FEATURE:
<223> OTHER INFORMATION: Synthetic oligomer

<400> SEQUENCE: 21
gttgtcatct tgttagacca gc                                           22

<210> SEQ ID NO 22
<211> LENGTH: 20
<212> TYPE: DNA
<213> ORGANISM: Artificial sequence
<220> FEATURE:
<223> OTHER INFORMATION: Synthetic oligomer

<400> SEQUENCE: 22
cctgcccttt gttctagttg                                              20

<210> SEQ ID NO 23
<211> LENGTH: 22
<212> TYPE: DNA
<213> ORGANISM: Artificial sequence
<220> FEATURE:
<223> OTHER INFORMATION: Synthetic oligomer

<400> SEQUENCE: 23
gatgaaggtt ttaatcttca tc                                           22

<210> SEQ ID NO 24
<211> LENGTH: 18
<212> TYPE: DNA
<213> ORGANISM: Artificial sequence
<220> FEATURE:
<223> OTHER INFORMATION: Synthetic oligomer

<400> SEQUENCE: 24
gtcatcttgt agaccagc                                                18

<210> SEQ ID NO 25
<211> LENGTH: 16
<212> TYPE: DNA
<213> ORGANISM: Artificial sequence
<220> FEATURE:
<223> OTHER INFORMATION: Synthetic oligomer

<400> SEQUENCE: 25
gtcatcttgt tagacc                                                  16

<210> SEQ ID NO 26
<211> LENGTH: 22
<212> TYPE: DNA
<213> ORGANISM: Artificial sequence
<220> FEATURE:
<223> OTHER INFORMATION: Synthetic oligomer

<400> SEQUENCE: 26
```

```
cctgcccttt gttctagttg tc                                          22

<210> SEQ ID NO 27
<211> LENGTH: 20
<212> TYPE: DNA
<213> ORGANISM: Artificial sequence
<220> FEATURE:
<223> OTHER INFORMATION: Synthetic oligomer

<400> SEQUENCE: 27
ggacgagaat ccatactcgg                                             20

<210> SEQ ID NO 28
<211> LENGTH: 23
<212> TYPE: DNA
<213> ORGANISM: Artificial sequence
<220> FEATURE:
<223> OTHER INFORMATION: Synthetic oligomer

<400> SEQUENCE: 28
cagattttct gaggacgaga atc                                         23

<210> SEQ ID NO 29
<211> LENGTH: 20
<212> TYPE: DNA
<213> ORGANISM: Artificial sequence
<220> FEATURE:
<223> OTHER INFORMATION: Synthetic oligomer

<400> SEQUENCE: 29
catccagatt ttctgaggac                                             20

<210> SEQ ID NO 30
<211> LENGTH: 21
<212> TYPE: DNA
<213> ORGANISM: Artificial sequence
<220> FEATURE:
<223> OTHER INFORMATION: Synthetic oligomer

<400> SEQUENCE: 30
ctcggcgcca tccagatttt c                                           21

<210> SEQ ID NO 31
<211> LENGTH: 22
<212> TYPE: DNA
<213> ORGANISM: Artificial sequence
<220> FEATURE:
<223> OTHER INFORMATION: Synthetic oligomer

<400> SEQUENCE: 31
catactcgga attttgtgat tc                                          22

<210> SEQ ID NO 32
<211> LENGTH: 18
<212> TYPE: DNA
<213> ORGANISM: Artificial sequence
<220> FEATURE:
<223> OTHER INFORMATION: Synthetic oligomer

<400> SEQUENCE: 32
ggcaatataa cccgcctc                                               18

<210> SEQ ID NO 33
<211> LENGTH: 19
<212> TYPE: DNA
<213> ORGANISM: Artificial sequence
<220> FEATURE:
```

-continued

<223> OTHER INFORMATION: Synthetic oligomer

<400> SEQUENCE: 33
ccatttaaaa gttgtctcc                                    19

<210> SEQ ID NO 34
<211> LENGTH: 19
<212> TYPE: DNA
<213> ORGANISM: Artificial sequence
<220> FEATURE:
<223> OTHER INFORMATION: Synthetic oligomer

<400> SEQUENCE: 34
gccatggttt tttctcagg                                    19

<210> SEQ ID NO 35
<211> LENGTH: 20
<212> TYPE: DNA
<213> ORGANISM: Artificial sequence
<220> FEATURE:
<223> OTHER INFORMATION: Synthetic oligomer

<400> SEQUENCE: 35
ctcaggtctt gcttggtgtc                                   20

<210> SEQ ID NO 36
<211> LENGTH: 22
<212> TYPE: DNA
<213> ORGANISM: Artificial sequence
<220> FEATURE:
<223> OTHER INFORMATION: Synthetic oligomer

<400> SEQUENCE: 36
tgtatcgtcc cgtagcttta gc                                22

<210> SEQ ID NO 37
<211> LENGTH: 19
<212> TYPE: DNA
<213> ORGANISM: Artificial sequence
<220> FEATURE:
<223> OTHER INFORMATION: Synthetic oligomer

<400> SEQUENCE: 37
gattgtatcg tcccgtagc                                    19

<210> SEQ ID NO 38
<211> LENGTH: 22
<212> TYPE: DNA
<213> ORGANISM: Artificial sequence
<220> FEATURE:
<223> OTHER INFORMATION: Synthetic oligomer

<400> SEQUENCE: 38
ggcgatatta gattgtatcg tc                                22

<210> SEQ ID NO 39
<211> LENGTH: 20
<212> TYPE: DNA
<213> ORGANISM: Artificial sequence
<220> FEATURE:
<223> OTHER INFORMATION: Synthetic oligomer

<400> SEQUENCE: 39
ttcaaccttg aaaccttgcg                                   20

<210> SEQ ID NO 40

```
<211> LENGTH: 19
<212> TYPE: DNA
<213> ORGANISM: Artificial Sequence
<220> FEATURE:
<223> OTHER INFORMATION: Synthetic oligomer

<400> SEQUENCE: 40
gccatggttt tttctcagg                                              19

<210> SEQ ID NO 41
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 41
ttcaaccttg aaaccttgcg                                             20

<210> SEQ ID NO 42
<211> LENGTH: 22
<212> TYPE: DNA
<213> ORGANISM: Artificial sequence
<220> FEATURE:
<223> OTHER INFORMATION: Synthetic oligomer

<400> SEQUENCE: 42
gatgaaggtt ttaatcttca tc                                          22

<210> SEQ ID NO 43
<211> LENGTH: 18
<212> TYPE: DNA
<213> ORGANISM: Artificial sequence
<220> FEATURE:
<223> OTHER INFORMATION: Synthetic oligomer

<400> SEQUENCE: 43
tttttcttaa tcttcatc                                               18

<210> SEQ ID NO 44
<211> LENGTH: 21
<212> TYPE: DNA
<213> ORGANISM: Artificial sequence
<220> FEATURE:
<223> OTHER INFORMATION: Synthetic oligomer

<400> SEQUENCE: 44
gacacacaaa aacaagagat g                                           21

<210> SEQ ID NO 45
<211> LENGTH: 19
<212> TYPE: DNA
<213> ORGANISM: Artificial sequence
<220> FEATURE:
<223> OTHER INFORMATION: Synthetic oligomer

<400> SEQUENCE: 45
gctgcatatt gaagaaagg                                              19

<210> SEQ ID NO 46
<211> LENGTH: 22
<212> TYPE: DNA
<213> ORGANISM: Artificial sequence
<220> FEATURE:
<223> OTHER INFORMATION: Synthetic oligomer

<400> SEQUENCE: 46
```

-continued catcaggata ttgagttgga tg                                              22

<210> SEQ ID NO 47
<211> LENGTH: 21
<212> TYPE: DNA
<213> ORGANISM: Artificial sequence
<220> FEATURE:
<223> OTHER INFORMATION: Synthetic oligomer

<400> SEQUENCE: 47
gtcccacatt gtgaaaatta t                                               21

<210> SEQ ID NO 48
<211> LENGTH: 22
<212> TYPE: DNA
<213> ORGANISM: Artificial sequence
<220> FEATURE:
<223> OTHER INFORMATION: Synthetic oligomer

<400> SEQUENCE: 48
cttgttgcat atatgatgag tc                                              22

<210> SEQ ID NO 49
<211> LENGTH: 19
<212> TYPE: DNA
<213> ORGANISM: Artificial sequence
<220> FEATURE:
<223> OTHER INFORMATION: Synthetic oligomer

<400> SEQUENCE: 49
gtaaatccat cttttcaag                                                  19

<210> SEQ ID NO 50
<211> LENGTH: 24
<212> TYPE: DNA
<213> ORGANISM: Artificial sequence
<220> FEATURE:
<223> OTHER INFORMATION: Synthetic oligomer

<400> SEQUENCE: 50
caagctatgt aaatccatct tttc                                            24

<210> SEQ ID NO 51
<211> LENGTH: 20
<212> TYPE: DNA
<213> ORGANISM: Artificial sequence
<220> FEATURE:
<223> OTHER INFORMATION: Synthetic oligomer

<400> SEQUENCE: 51
cctaacaagc tatgtaaatc                                                 20

<210> SEQ ID NO 52
<211> LENGTH: 21
<212> TYPE: DNA
<213> ORGANISM: Artificial sequence
<220> FEATURE:
<223> OTHER INFORMATION: Synthetic oligomer

<400> SEQUENCE: 52
taacagactg acaagtctca a                                               21

<210> SEQ ID NO 53
<211> LENGTH: 21
<212> TYPE: DNA
<213> ORGANISM: Artificial sequence
<220> FEATURE:

<223> OTHER INFORMATION: Synthetic oligomer

<400> SEQUENCE: 53
caatgttaat attcttcttt a                                             21

<210> SEQ ID NO 54
<211> LENGTH: 22
<212> TYPE: DNA
<213> ORGANISM: Artificial sequence
<220> FEATURE:
<223> OTHER INFORMATION: Synthetic oligomer

<400> SEQUENCE: 54
atattcttct ttatttatat gt                                            22

<210> SEQ ID NO 55
<211> LENGTH: 22
<212> TYPE: DNA
<213> ORGANISM: Artificial sequence
<220> FEATURE:
<223> OTHER INFORMATION: Synthetic oligomer

<400> SEQUENCE: 55
gttgcatttt aaatcttgaa tc                                            22

<210> SEQ ID NO 56
<211> LENGTH: 20
<212> TYPE: DNA
<213> ORGANISM: Artificial sequence
<220> FEATURE:
<223> OTHER INFORMATION: Synthetic oligomer

<400> SEQUENCE: 56
cctttaatat tcttcgattt                                               20

<210> SEQ ID NO 57
<211> LENGTH: 23
<212> TYPE: DNA
<213> ORGANISM: Artificial sequence
<220> FEATURE:
<223> OTHER INFORMATION: Synthetic oligomer

<400> SEQUENCE: 57
gttgtaacgc gttgataatt ctg                                           23

<210> SEQ ID NO 58
<211> LENGTH: 20
<212> TYPE: DNA
<213> ORGANISM: Artificial sequence
<220> FEATURE:
<223> OTHER INFORMATION: Synthetic oligomer

<400> SEQUENCE: 58
caagtctcaa tgtcaatgtt                                               20

<210> SEQ ID NO 59
<211> LENGTH: 20
<212> TYPE: DNA
<213> ORGANISM: Artificial sequence
<220> FEATURE:
<223> OTHER INFORMATION: Synthetic oligomer

<400> SEQUENCE: 59
agtctcgact tgctacctca                                               20

<210> SEQ ID NO 60

```
<211> LENGTH: 22
<212> TYPE: DNA
<213> ORGANISM: Artificial sequence
<220> FEATURE:
<223> OTHER INFORMATION: Synthetic oligomer

<400> SEQUENCE: 60
tgtgcttact gttatactac tc                                              22

<210> SEQ ID NO 61
<211> LENGTH: 12
<212> TYPE: PRT
<213> ORGANISM: Artificial sequence
<220> FEATURE:
<223> OTHER INFORMATION: Synthetic arginine-rich peptide

<400> SEQUENCE: 61

Arg Arg Arg Arg Arg Arg Arg Arg Arg Phe Phe Cys
1               5                   10

<210> SEQ ID NO 62
<211> LENGTH: 14
<212> TYPE: PRT
<213> ORGANISM: Artificial sequence
<220> FEATURE:
<223> OTHER INFORMATION: Synthetic arginine-rich peptide
<220> FEATURE:
<221> NAME/KEY: VARIANT
<222> LOCATION: (2)..(13)
<223> OTHER INFORMATION: Xaa=6-aminohexanoic acid
<220> FEATURE:
<221> NAME/KEY: VARIANT
<222> LOCATION: (14)..(14)
<223> OTHER INFORMATION: Xaa=beta-alanine

<400> SEQUENCE: 62

Arg Xaa Arg Arg Xaa Arg Arg Xaa Arg Arg Xaa Arg Xaa Xaa
1               5                   10

<210> SEQ ID NO 63
<211> LENGTH: 17
<212> TYPE: PRT
<213> ORGANISM: Artificial sequence
<220> FEATURE:
<223> OTHER INFORMATION: Synthetic arginine-rich peptide
<220> FEATURE:
<221> NAME/KEY: VARIANT
<222> LOCATION: (2)..(16)
<223> OTHER INFORMATION: Xaa=6-aminohexanoic acid
<220> FEATURE:
<221> NAME/KEY: VARIANT
<222> LOCATION: (17)..(17)
<223> OTHER INFORMATION: Xaa=beta-alanine

<400> SEQUENCE: 63

Arg Xaa Arg Xaa Arg Xaa Arg Xaa Arg Xaa Arg Xaa Arg Xaa Arg Xaa
1               5                   10                  15

Xaa

<210> SEQ ID NO 64
<211> LENGTH: 9
<212> TYPE: PRT
<213> ORGANISM: Artificial sequence
<220> FEATURE:
<223> OTHER INFORMATION: Synthetic arginine-rich peptide
<220> FEATURE:
<221> NAME/KEY: VARIANT
<222> LOCATION: (2)..(8)
<223> OTHER INFORMATION: Xaa=6-aminohexanoic acid
<220> FEATURE:
<221> NAME/KEY: VARIANT
```

```
<222> LOCATION: (9)..(9)
<223> OTHER INFORMATION: Xaa=beta-alanine

<400> SEQUENCE: 64

Arg Xaa Arg Xaa Arg Xaa Arg Xaa Xaa
1               5

<210> SEQ ID NO 65
<211> LENGTH: 8
<212> TYPE: PRT
<213> ORGANISM: Artificial sequence
<220> FEATURE:
<223> OTHER INFORMATION: Synthetic arginine-rich peptide
<220> FEATURE:
<221> NAME/KEY: VARIANT
<222> LOCATION: (2)..(7)
<223> OTHER INFORMATION: Xaa=6-aminohexanoic acid
<220> FEATURE:
<221> NAME/KEY: VARIANT
<222> LOCATION: (8)..(8)
<223> OTHER INFORMATION: Xaa=beta-alanine

<400> SEQUENCE: 65

Arg Xaa Arg Arg Xaa Arg Xaa Xaa
1               5

<210> SEQ ID NO 66
<211> LENGTH: 11
<212> TYPE: PRT
<213> ORGANISM: Artificial sequence
<220> FEATURE:
<223> OTHER INFORMATION: Synthetic arginine-rich peptide
<220> FEATURE:
<221> NAME/KEY: VARIANT
<222> LOCATION: (2)..(10)
<223> OTHER INFORMATION: Xaa=6-aminohexanoic acid
<220> FEATURE:
<221> NAME/KEY: VARIANT
<222> LOCATION: (11)..(11)
<223> OTHER INFORMATION: Xaa=beta-alanine

<400> SEQUENCE: 66

Arg Xaa Arg Arg Xaa Arg Arg Xaa Arg Xaa Xaa
1               5                   10

<210> SEQ ID NO 67
<211> LENGTH: 123
<212> TYPE: DNA
<213> ORGANISM: Zaire ebolavirus

<400> SEQUENCE: 67
gatgaagatt aaaaccttca tcatccttac gtcaattgaa ttctctagca ctcgaagctt      60
attgtcttca atgtaaaaga aaagctggtc taacaagatg acaactagaa caaagggcag    120
ggg                                                                  123

<210> SEQ ID NO 68
<211> LENGTH: 123
<212> TYPE: DNA
<213> ORGANISM: Zaire ebolavirus

<400> SEQUENCE: 68
gatgaagatt aaaaccttca tcatccttac gtcaattgaa ttctctagca ctcgaagctt      60
attgtcctca atgtaaaaga aaagctggtc taacaagatg acaaccagaa caaagggcag    120
ggg                                                                  123

<210> SEQ ID NO 69
```

```
<211> LENGTH: 153
<212> TYPE: DNA
<213> ORGANISM: Sudan ebolavirus

<400> SEQUENCE: 69
atgatgaaga ttaaaacctt catcatcctt taaaaagaga gctattcttt atctgaatgt    60
ccttattaat gtctaagagc tattattttg taccctctta gcctagacac tgcccagcat   120
ataagccatg cagcaggata ggacttatag aca                                153

<210> SEQ ID NO 70
<211> LENGTH: 162
<212> TYPE: DNA
<213> ORGANISM: Reston ebolavirus

<400> SEQUENCE: 70
gatgaagatt aaaaccttca tcgccagtaa atgattatat tgtctgtagg caggtgttta    60
ctccacctta aatttggaaa tatcctacct taggaccatt gtcaagaggt gcataggcat   120
taccacccct gagaacatgt acaataataa attgaaggta tg                      162

<210> SEQ ID NO 71
<211> LENGTH: 92
<212> TYPE: DNA
<213> ORGANISM: Lake Victoria marburgvirus

<400> SEQUENCE: 71
gaagaatatt aaaggttttc tttaatattc agaaaaggtt ttttattctc ttctttcttt    60
ttgcaaacat attgaaataa taattttcac aa                                 92

<210> SEQ ID NO 72
<211> LENGTH: 486
<212> TYPE: DNA
<213> ORGANISM: Zaire ebolavirus

<400> SEQUENCE: 72
gatgaagatt aatgcggagg tctgataaga ataaacctta ttattcagat taggccccaa    60
gaggcattct tcatctcctt ttagcaaagt actatttcag ggtagtccaa ttagtggcac   120 gtctttagc tgtatatcag tcgcccctga gatacgccac aaaagtgtct ctaagctaaa   180
ttggtctgta cacatcccat acattgtatt aggggcaata atatctaatt gaacttagcc   240
gtttaaaatt tagtgcataa atctgggcta acaccaccag gtcaactcca ttggctgaaa   300
agaagcttac ctacaacgaa catcactttg agcgccctca caattaaaaa ataggaacgt   360
cgttccaaca atcgagcgca aggttttcaag gttgaactga gagtgtctag acaacaaaat   420
attgatactc cagacaccaa gcaagacctg agaaaaaacc atggctaaag ctacgggacg   480
atacaa                                                              486

<210> SEQ ID NO 73
<211> LENGTH: 486
<212> TYPE: DNA
<213> ORGANISM: Zaire ebolavirus

<400> SEQUENCE: 73
gatgaagatt aatgcggagg tctgataaga ataaacctta ttattcagat taggccccaa    60
gaggcattct tcatctcctt ttagcaaagt actatttcag ggtagtccaa ttagtgacac   120
gtctcttagc tgtatatcag tcgcccctga gatacgccac aaaagtgtct ctaagctaaa   180
ttggtctgta cacatctcat acattgtatt agggacaata atatctaatt gaacttagcc   240
```

```
gtttaaaatt tagtgcataa atctgggcta actccaccag gtcaactcca ttggctgaaa    300
agaagcctac ctacaacgaa catcactttg agcgccctca catttaaaaa ataggaacgt    360
cgttccaaca atcgagcgca aggtttcaag gttgaactga gagtgtctag acaacaaagt    420
atcgatcctc cagacaccaa gcaagacctg agaaaaaacc atggctaaag ctacgggacg    480
atacaa                                                               486
```

```
<210> SEQ ID NO 74
<211> LENGTH: 501
<212> TYPE: DNA
<213> ORGANISM: Sudan ebolavirus

<400> SEQUENCE: 74
atgatgaaaa ttaatgagaa ggttccaaga ttgacttcaa tccaaacacc ttgctctgcc     60
aattttcatc tccttaagat atatgatttt gttcctgcga gataaggtta tcaaataggg    120
tgtgtatctc ttttacatat ttgggctccc actaggctag ggtttatagt taaggaagac    180
tcatcacatt ttttattgaa ctagtctact cgcagaatcc taccgggaat agaaattaga    240
acatttgtga actttgact ataggaaata attttcaaca ctacctgaga tcaggttatt    300
cttccaactt attctgcaag taattgttta gcatcataac aacaacgtta taatttaaga    360
atcaagtctt gtaacagaaa taaagataac agaaagaacc tttattatac gggtccatta    420
attttatagg agaagctcct tttacaagcc taagattcca ttagagataa ccagaatggc    480
taaagccaca ggccggtaca a                                              501
```

```
<210> SEQ ID NO 75
<211> LENGTH: 497
<212> TYPE: DNA
<213> ORGANISM: Reston ebolavirus

<400> SEQUENCE: 75
gatgaagatt aattgcggag gaatcaggaa ttcaacttta gttccttaag gcctcgtccg     60
aatcttcatc agttcgtaag ttctttata gaagtcatta gcttctaagg tgattatatt    120
ttagtattaa attttgctaa ttgcttgcta taaagttgaa atgtctaatg cttaaatgaa    180
cacttttttg aagctgacat acgaatacat catatcatat gaaaacatcg caattagagc    240
gtccttgaag tctggcattg acagtcacca ggctgttctc agtagtctgt ccttggaagc    300
tcttggggag acaaaaagag gtcccagaga gtcccaacag gttggcataa ggtcattaac    360
accagcatag tcggctcgac caagactgta agcgagtcga tttcaactaa aaagattatt    420
tcttgttgtt taaacaaatt cctttttgtgt gagacatcct caaggcacaa gatggctaaa    480
gccacaggcc gatacaa                                                   497
```

```
<210> SEQ ID NO 76
<211> LENGTH: 234
<212> TYPE: DNA
<213> ORGANISM: Lake Victoria marburgvirus

<400> SEQUENCE: 76
gaagaacatt aagaaaaagg atgttcttat ttttcaacta aacttgcata tcctttgttg     60
atacccttga gagacaactt ttgacactag atcacggatc aagcatattt cattcaaaca    120
ccccaaattt tcaatcatac acataataac catttttagta gcgttacctt tcaatacaat    180
ctaggtgatt gtgaaaagac ttccaaacat ggcagaatta tcaacgcgtt acaa          234
```

```
<210> SEQ ID NO 77
```

```
<211> LENGTH: 19
<212> TYPE: DNA
<213> ORGANISM: Artificial Sequence
<220> FEATURE:
<223> OTHER INFORMATION: Oligomer specific to AUG start site region of
      Ebola VP24
<220> FEATURE:
<221> NAME/KEY: misc_feature
<222> LOCATION: (3)..(8)
<223> OTHER INFORMATION: Positively charged piperazine moieties are
      incorporated at the indicated positions into phosphorodiamidate
      linkages forming the backbone

<400> SEQUENCE: 77
gccatggttt tttctcagg                                                  19

<210> SEQ ID NO 78
<211> LENGTH: 20
<212> TYPE: DNA
<213> ORGANISM: Artificial Sequence
<220> FEATURE:
<223> OTHER INFORMATION: Oligomer specific to AUG start site region of
      Ebola VP35
<220> FEATURE:
<221> NAME/KEY: misc_feature
<222> LOCATION: (2)..(7)
<223> OTHER INFORMATION: Positively charged piperazine moieties are
      incorporated at the indicated positions into phosphorodiamidate
      linkages forming the backbone

<400> SEQUENCE: 78
cctgcccttt gttctagttg                                                 20

<210> SEQ ID NO 79
<211> LENGTH: 23
<212> TYPE: DNA
<213> ORGANISM: Artificial Sequence
<220> FEATURE:
<223> OTHER INFORMATION: Oligomer specific to AUG start site region of
      Marburg NP
<220> FEATURE:
<221> NAME/KEY: misc_feature
<222> LOCATION: (10)..(12)
<223> OTHER INFORMATION: Positively charged piperazine moieties are
      incorporated at the indicated positions into phosphorodiamidate
      linkages forming the backbone
<220> FEATURE:
<221> NAME/KEY: modified_base
<222> LOCATION: (12)..(12)
<223> OTHER INFORMATION: I

<400> SEQUENCE: 79
gaatattaac anactgacaa gtc                                             23

<210> SEQ ID NO 80
<211> LENGTH: 21
<212> TYPE: DNA
<213> ORGANISM: Artificial Sequence
<220> FEATURE:
<223> OTHER INFORMATION: Oligomer specific to AUG start site region of
      Marburg VP24
<220> FEATURE:
<221> NAME/KEY: misc_feature
<222> LOCATION: (6)..(7)
<223> OTHER INFORMATION: Positively charged piperazine moieties are
      incorporated at the indicated positions into phosphorodiamidate
      linkages forming the backbone
<220> FEATURE:
<221> NAME/KEY: modified_base
<222> LOCATION: (9)..(19)
<223> OTHER INFORMATION: I
<220> FEATURE:
<221> NAME/KEY: misc_feature
<222> LOCATION: (9)..(9)
```

```
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t

<400> SEQUENCE: 80
cgttgatant tctgccatnc t                                          21

<210> SEQ ID NO 81
<211> LENGTH: 22
<212> TYPE: DNA
<213> ORGANISM: Zaire ebolavirus

<400> SEQUENCE: 81
gatgaagatt aaaaccttca tc                                         22

<210> SEQ ID NO 82
<211> LENGTH: 45
<212> TYPE: DNA
<213> ORGANISM: Zaire ebolavirus

<400> SEQUENCE: 82
aagaaaagct ggtctaacaa gatgacaact agaacaaagg gcagg                45
```

ANTISENSE ANTIVIRAL COMPOUNDS AND METHODS FOR TREATING A FILOVIRUS INFECTION

CROSS REFERENCE TO RELATED APPLICATION

This application is a continuation of U.S. patent application Ser. No. 13/853,180, filed Aug. 09, 2010, now issued as U.S. Pat. No. 8,198,429, which application is incorporated herein by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 120178_436C7_SEQUENCE LISTING.txt. The text file is 22 KB, was created on May 11, 2012 and is being submitted electronically via EFS-Web.

FIELD OF THE INVENTION

This invention relates to antisense oligonucleotide compounds for use in treating an infection by a virus of the Filoviridae family and antiviral treatment methods employing the compounds. More specifically, it relates to treatment methods and compounds for treating viral infections in mammals including primates by Ebola and Marburg viruses.

Agrawal, S., S. H. Mayrand, et al. (1990). "Site-specific excision from RNA by RNase H and mixed-phosphate-backbone oligodeoxynucleotides." *Proc Natl Acad Sci USA* 87(4): 1401-5.

Arora, V. and P. L. Iversen (2001). "Redirection of drug metabolism using antisense technology." *Curr Opin Mol Ther* 3(3): 249-57.

Blommers, M. J., U. Pieles, et al. (1994). "An approach to the structure determination of nucleic acid analogues hybridized to RNA. NMR studies of a duplex between 2'-OMe RNA and an oligonucleotide containing a single amide backbone modification." *Nucleic Acids Res* 22(20): 4187-94.

Bonham, M. A., S. Brown, et al. (1995). "An assessment of the antisense properties of RNase H-competent and steric-blocking oligomers." *Nucleic Acids Res* 23(7): 1197-203.

Borio, L., T. Inglesby, et al. (2002). "Hemorrhagic fever viruses as biological weapons: medical and public health management." *Jama* 287(18): 2391-405.

Boudvillain, M., M. Guerin, et al. (1997). "Transplatin-modified oligo(2'-O-methyl ribonucleotide)s: a new tool for selective modulation of gene expression." *Biochemistry* 36(10): 2925-31.

Bray, M., K. Davis, et al. (1998). "A mouse model for evaluation of prophylaxis and therapy of Ebola hemorrhagic fever." *J Infect Dis* 178(3): 651-61.

Burnett, J., E. A. Henchal, et al. (2005). "The evolving field of biodefence: Therapeutic developments and diagnostics." *Nat Rev Drug Disc* 4: 281-297.

Connolly, B. M., K. E. Steele, et al. (1999). "Pathogenesis of experimental Ebola virus infection in guinea pigs." *J Infect Dis* 179 Suppl 1: S203-17.

Cross, C. W., J. S. Rice, et al. (1997). "Solution structure of an RNA×DNA hybrid duplex containing a 3'-thioformacetal linker and an RNA A-tract." *Biochemistry* 36(14): 4096-107.

Dagle, J. M., J. L. Littig, et al. (2000). "Targeted elimination of zygotic messages in *Xenopus laevis* embryos by modified oligonucleotides possessing terminal cationic linkages." *Nucleic Acids Res* 28(10): 2153-7.

Ding, D., S. M. Grayaznov, et al. (1996). "An oligodeoxyribonucleotide N3'-->P5'phosphoramidate duplex forms an A-type helix in solution." *Nucleic Acids Res* 24(2): 354-60.

Egholm, M., O. Buchardt, et al. (1993). "PNA hybridizes to complementary oligonucleotides obeying the Watson-Crick hydrogen-bonding rules." *Nature* 365(6446): 566-8.

Feldmann, H., S. Jones, et al. (2003). "Ebola virus: from discovery to vaccine." *Nat Rev Immunol* 3(8): 677-85.

Feldmann, H. and M. P. Kiley (1999). "Classification, structure, and replication of filoviruses." *Curr Top Microbiol Immunol* 235: 1-21.

Feldmann, H., H. D. Klenk, et al. (1993). "Molecular biology and evolution of filoviruses." *Arch Virol Suppl* 7: 81-100.

Felgner, P. L., T. R. Gadek, et al. (1987). "Lipofection: a highly efficient, lipid-mediated DNA-transfection procedure." *Proc Natl Acad Sci USA* 84(21): 7413-7.

Gait, M. J., A. S. Jones, et al. (1974). "Synthetic-analogues of polynucleotides XII. Synthesis of thymidine derivatives containing an oxyacetamido- or an oxyformamido-linkage instead of a phosphodiester group." *J Chem Soc [Perkin 1]* 0(14): 1684-6.

Gee, J. E., I. Robbins, et al. (1998). "Assessment of high-affinity hybridization, RNase H cleavage, and covalent linkage in translation arrest by antisense oligonucleotides." *Antisense Nucleic Acid Drug Dev* 8(2): 103-11.

Geisbert, T. W. and L. E. Hensley (2004). "Ebola virus: new insights into disease aetiopathology and possible therapeutic interventions." *Expert Rev Mol Med* 6(20): 1-24.

Geisbert, T. W., L. E. Hensley, et al. (2003). "Treatment of Ebola virus infection with a recombinant inhibitor of factor VIIa/tissue factor: a study in rhesus monkeys." *Lancet* 362 (9400): 1953-8.

Jahrling, P. B., T. W. Geisbert, et al. (1999). "Evaluation of immune globulin and recombinant interferon-alpha2b for treatment of experimental Ebola virus infections." *J Infect Dis* 179 Suppl 1: S224-34.

Lesnikowski, Z. J., M. Jaworska, et al. (1990). "Octa(thymidine methanephosphonates) of partially defined stereochemistry: synthesis and effect of chirality at phosphorus on binding to pentadecadeoxyriboadenylic acid." *Nucleic Acids Res* 18(8): 2109-15.

Mertes, M. P. and E. A. Coats (1969). "Synthesis of carbonate analogs of dinucleosides. 3'-Thymidinyl 5'-thymidinyl carbonate, 3'-thymidinyl 5'-(5-fluoro-2'-deoxyuridinyl) carbonate, and 3'-(5-fluoro-2'-deoxyuridinyl) 5'-thymidinyl carbonate." *J Med Chem* 12(1): 154-7.

Moulton, H. M., M. H. Nelson, et al. (2004). "Cellular uptake of antisense morpholino oligomers conjugated to arginine-rich peptides." *Bioconjug Chem* 15(2): 290-9.

Nelson, M. H., D. A. Stein, et al. (2005). "Arginine-rich peptide conjugation to morpholino oligomers: effects on antisense activity and specificity." *Bioconjug Chem* 16(4): 959-66.

Peters, C. J. and J. W. LeDuc (1999). "An introduction to Ebola: the virus and the disease." *J Infect Dis* 179 Suppl 1: ix-xvi.

Sanchez, A., M. P. Kiley, et al. (1993). "Sequence analysis of the Ebola virus genome: organization, genetic elements, and comparison with the genome of Marburg virus." *Virus Res* 29(3): 215-40.

Strauss, J. H. and E. G. Strauss (2002). *Viruses and Human Disease*. San Diego, Academic Press.

Summerton, J. and D. Weller (1997). "Morpholino antisense oligomers: design, preparation, and properties." *Antisense Nucleic Acid Drug Dev* 7(3): 187-95.

Toulme, J. J., R. L. Tinevez, et al. (1996). "Targeting RNA structures by antisense oligonucleotides." *Biochimie* 78(7): 663-73.

Warfield, K. L., J. G. Perkins, et al. (2004). "Role of natural killer cells in innate protection against lethal ebola virus infection." *J Exp Med* 200(2): 169-79.

BACKGROUND OF THE INVENTION

Minus-strand (−) RNA viruses are major causes of human suffering that cause epidemics of serious human illness. In humans the diseases caused by these viruses include influenza (Orthomyxoviridae), mumps, measles, upper and lower respiratory tract disease (Paramyxoviridae), rabies (Rhabdoviridae), hemorrhagic fever (Filoviridae, Bunyaviridae and Arenaviridae), encephalitis (Bunyaviridae) and neurological illness (Bornaviridae). Virtually the entire human population is thought to be infected by many of these viruses (e.g. respiratory syncytial virus) (Strauss and Strauss 2002).

The order Mononegavirales is composed of four minus strand RNA virus families, the Rhabdoviridae, the Paramyxoviridae, the Filoviridae and the Bornaviridae. The viruses in these families contain a single strand of non-segmented negative-sense RNA and are responsible for a wide range of significant diseases in fish, plants, and animals. Viruses with segmented (−) RNA genomes belong to the Arenaviridae, Bunyaviridae and Orthomyxoviridae families and possess genomes with two, three and seven or eight segments, respectively.

The expression of the five to ten genes encoded by the members of the Mononegavirales is controlled at the level of transcription by the order of the genes on the genome relative to the single 3' promoter. Gene order throughout the Mononegavirales is highly conserved. Genes encoding products required in stoichiometric amounts for replication are always at or near the 3' end of the genome while those whose products are needed in catalytic amounts are more promoter distal (Strauss and Strauss 2002). The segmented (−) RNA viruses encode genes with similar functions to those encoded by the Mononegavirales. Other features of virion structure and replication pathways are also shared among the (−) RNA viruses.

For some (−) RNA viruses, effective vaccines are available (e.g. influenza, mumps and measles virus) whereas for others there are no effective vaccines (e.g. Ebola virus and Marburg virus). In general, no effective antiviral therapies are available to treat an infection by any of these viruses. As with many other human viral pathogens, available treatment involves supportive measures such as anti-pyretics to control fever, fluids, antibiotics for secondary bacterial infections and respiratory support as necessary.

The development of a successful therapeutic for filoviruses Ebola and Marburg virus is a long-sought and seemingly difficult endeavor (Geisbert and Hensley 2004). Although they cause only a few hundred deaths worldwide each year, filoviruses are considered a significant world health threat and have many of the characteristics commonly associated with biological weapons since they can be grown in large quantities, can be fairly stable, are highly infectious as an aerosol, and are exceptionally deadly (Borio, Inglesby et al. 2002). Filoviruses are relatively simple viruses of 19 Kb genomes and consist of seven genes which encode nucleoprotein (NP), glycoprotein (GP), four smaller viral proteins (VP24, VP30, VP35 and VP40), and the RNA-dependent RNA polymerase (L protein) all in a single strand of negative-sensed RNA (Feldmann and Kiley 1999). The development of an effective therapeutic for Ebola virus has been hindered by a lack of reagents and a clear understanding of filovirus pathogenesis, disparity between animal models, and both the difficulty and danger of working with Ebola virus in biosafety level (BSL)-4 conditions (Geisbert and Hensley 2004; Burnett, Henchal et al. 2005). Administration of type I interferons, therapeutic vaccines, immune globulins, ribavirin, and other nucleoside analogues have been somewhat successful in rodent Ebola virus models, but not in infected nonhuman primates (Jahrling, Geisbert et al. 1999; Geisbert and Hensley 2004; Warfield, Perkins et al. 2004). Ebola virus frequently causes severe disseminated intravascular coagulation and administration of a recombinant clotting inhibitor has recently shown to protect 33% of rhesus monkeys (Geisbert, Hensley et al. 2003; Geisbert and Hensley 2004). Host-directed therapeutics alone have not proven to be a sufficiently efficacious therapeutic approach. A well-orchestrated sequence-specific attack on viral gene expression is required for a highly successful anti-filovirus therapeutic and treatment regimen.

In view of the severity of the diseases caused by (−) RNA viruses, in particular members of the Filoviridae family of viruses, and the lack of effective prevention or therapies, it is therefore an object of the present invention to provide therapeutic compounds and methods for treating a host infected with a (−) RNA virus.

SUMMARY OF THE INVENTION

The invention includes, in one aspect, an anti-viral antisense composition effective in inhibiting replication within a host cell of an Ebola virus or Marburg virus. The composition contains one or more antisense compounds that target viral RNA sequences within a region of the positive-strand mRNA that includes the region 5' and/or the region 25-basepair region just downstream of the AUG start site of the VP35 polymerase, the VP24 membrane associated protein, or the VP30 nucleoprotein (NP), including combinations and mixtures thereof Specific embodiments include compositions or mixtures for treating Marburg virus infections, comprising a first and a second antisense oligonucleotide, wherein each oligonucleotide is composed of morpholino subunits linked by phosphorous-containing intersubunit linkages which join a morpholino nitrogen of one subunit to a 5' exocyclic carbon of an adjacent subunit in accordance with the structure:

$$Z=P-X$$

wherein $Y_1$=O, Z=O, Pj is a purine or pyrimidine base-pairing moiety effective to bind, by base-specific hydrogen bonding, to a base in a polynucleotide, and X is selected from alkyl alkoxy; thioalkoxy; —NR$_2$, wherein each R is independently H or lower alkyl; and 1-piperazino, wherein the first oligonucleotide targets Marburg NP and consists of the sequence set forth in SEQ ID NO:79, and the second oligonucleotide targets Marburg VP24 and consists of the sequence set forth in SEQ ID NO:80. Certain embodiments comprise an approximately 1:1 mixture of equivalent concentrations (w/v) of the first and second antisense oligonucleotides.

Certain embodiments include an antisense oligonucleotide for treating Marburg virus infections, which is composed of morpholino subunits linked by phosphorous-containing intersubunit linkages which join a morpholino nitrogen of one subunit to a 5' exocyclic carbon of an adjacent subunit in accordance with the structure:

$$Z=\overset{|}{\underset{Y_1}{P}}-X$$

wherein $Y_1=O$, $Z=O$, Pj is a purine or pyrimidine base-pairing moiety effective to bind, by base-specific hydrogen bonding, to a base in a polynucleotide, and X is selected from alkyl alkoxy; thioalkoxy; —$NR_2$, wherein each R is independently H or lower alkyl; and 1-piperazino, wherein the oligonucleotide targets Marburg NP and consists of the sequence set forth in SEQ ID NO:79.

Certain embodiments include an antisense oligonucleotide for treating Marburg virus infections, which is composed of morpholino subunits linked by phosphorous-containing intersubunit linkages which join a morpholino nitrogen of one subunit to a 5' exocyclic carbon of an adjacent subunit in accordance with the structure:

$$Z=\overset{|}{\underset{Y_1}{P}}-X$$

wherein $Y_1=O$, $Z=O$, Pj is a purine or pyrimidine base-pairing moiety effective to bind, by base-specific hydrogen bonding, to a base in a polynucleotide, and X is selected from alkyl alkoxy; thioalkoxy; —$NR_2$, wherein each R is independently H or lower alkyl; and 1-piperazino, wherein the oligonucleotide targets Marburg VP24 and consists of the sequence set forth in SEQ ID NO:80.

Also included are compositions or mixtures for treating Ebola virus infections, comprising a first and a second antisense oligonucleotide, wherein each oligonucleotide is composed of morpholino subunits linked by phosphorous-containing intersubunit linkages which join a morpholino nitrogen of one subunit to a 5' exocyclic carbon of an adjacent subunit in accordance with the structure:

$$Z=\overset{|}{\underset{Y_1}{P}}-X$$

wherein $Y_1=O$, $Z=O$, Pj is a purine or pyrimidine base-pairing moiety effective to bind, by base-specific hydrogen bonding, to a base in a polynucleotide, and X is selected from alkyl alkoxy; thioalkoxy; —$NR_2$, wherein each R is independently H or lower alkyl; and 1-piperazino, wherein the first oligonucleotide targets Ebola VP24 and consists of the sequence set forth in SEQ ID NO:77, and the second oligonucleotide targets Ebola VP35 and consists of the sequence set forth in SEQ ID NO:78. Certain embodiments comprise an approximately 1:1 mixture of equivalent concentrations (w/v) of the first and second antisense oligonucleotides. In specific embodiments, the compositions or mixtures of antisense oligonucleotides are formulated in phosphate buffered saline (PBS).

In another aspect, the invention includes a method of treating an Ebola or Marburg virus infection in a mammalian host, by administering to the host, a therapeutically effective amount of a composition of the type described above. The method includes, in exemplary embodiments, administering a composition having a combination of antisense compounds targeted against different viral proteins, such as the VP35, VP24, and NP proteins, including combinations thereof.

In a related, more general aspect, the invention includes a method of vaccinating a mammalian subject against Ebola or Marburg virus by pre-treating the subject with the composition of the invention, and exposing the subject to the Ebola virus, preferably in an attenuated form.

These and other objects and features of the invention will become more fully apparent when the following detailed description of the invention is read in conjunction with the accompanying drawings.

BRIEF DESCRIPTION OF THE FIGURES

FIGS. 2A-2G show the backbone structures of various oligonucleotide analogs with uncharged backbones and FIG. 2H shows a cationic linkage structure.

FIGS. 4A-4B show the target regions of 6 antisense compounds targeted against the VP35 gene in Ebola virus.

FIG. 7 is a plot of treatment efficacy, expressed as a fraction of mouse survivors 10 days post infection, as a function of VP35 antisense length.

FIG. 8 is a plot of treatment efficacy, expressed as percent survival, as a function of dose of various combinations of antisense compounds.

FIG. 9A shows the schedule of the experimental protocol. FIG. 9B plots the fraction of mouse survivors with various dose schedules of antisense compounds.

FIG. 18A shows the combined Kaplan-Meier survival analysis from two proof-of-concept experiments in which monkeys (n=8) were treated daily with 40 mg/kg AVI-6002. Doses were divided into equal volumes and administered at intraperitoneal and subcutaneous sites. Four monkeys received treatments for 14 days and four received treatment for 10 days. A single untreated animal served as an infection control. FIGS. 18B-F show multiple-dose post-exposure efficacy assessment of AVI-6002 for treatment of ZEBOV infection in rhesus monkeys. Animals were randomly assigned to treatment groups and the in-life portion of the experiment was conducted under single-blind experimental conditions. AVI-6002 was delivered at one of four dose levels: 40 (6002-40; n=5), 28 (6002-28; n=5), 16 (6002-16; n=5), or 4 mg/kg (6002-4; n=5). Four monkeys were treated with 40 mg/kg negative-control PMOplus formulation (AVI-6003; 6003-40) and one animal was treated with PBS. All treatments were administered by bolus intravenous injection daily through day 14 post-infection. Statistically significant differences (*; P<0.05) between means of AVI-6002 treatments and the AVI-6003 treatment are indicated. FIG. 18B shows the Kaplan-Meier survival curves. Mean platelet counts (FIG. 18C), peripheral blood lymphocytes (FIG. 18D), and aspartate aminotransferase (AST) (FIG. 18E) are also displayed. Plasma viremia (FIG. 18F) was assessed using quantitative real-time PCR and results from samples collected from individual animals on day 8 are shown.

FIG. 19A shows combined survival and viremia from two independent proof-of-concept evaluations.

AVI-6003 was administered at dose of 40 (n=4) or 30 mg/kg (n=3) via intraperitoneal and subcutaneous injections or was delivered at 40 mg/kg using either subcutaneous (n=3) or intravenous (n=3) injections. Treatments delivered at intraperitoneal and subcutaneous sites were administered by injecting equal volumes at each site. Viremia results obtained using standard plaque assay (Vero cells) from day 8 are presented and are displayed as the range and geometric mean. FIGS. 19B-F show multiple-dose post-exposure efficacy assessment of AVI-6003 for treatment of MARV infection in cynomolgus monkeys. In-life study components were conducted under single-blind experimental conditions and animals were randomized to treatments. AVI-6003 was delivered intravenously at one of three doses: 30 (6003-30; n=5), 15 (6003-15; n=5), or 7.5 mg/kg (6003-15; n=5). Four monkeys were treated with 30 mg/kg negative-control PMOplus formulation (AVI-6002; 6002-30) and one animal was treated with PBS. Statistically significant differences (*; P<0.05) between means of AVI-6003 treatments and the AVI-6002 treatment are indicated. FIG. 19B shows Kaplan-Meier survival curves. Mean platelet counts (FIG. 19C), peripheral blood lymphocytes (FIG. 19D), and aspartate aminotransferase (AST) (FIG. 19E) and are displayed. Plasma viremia (FIG. 19F) was assessed using standard plaque assay and the maximum viremia value (occurring at either at day 8 or day 10 post infection in all animals) obtained during the course of infection is displayed for each animal.

DETAILED DESCRIPTION OF THE INVENTION

I. Definitions

The terms below, as used herein, have the following meanings, unless otherwise indicated:

The terms "oligonucleotide analog" refers to an oligonucleotide having (i) a modified backbone structure, e.g., a backbone other than the standard phosphodiester linkage found in natural oligo- and polynucleotides, and (ii) optionally, modified sugar moieties, e.g., morpholino moieties rather than ribose or deoxyribose moieties. The analog supports bases capable of hydrogen bonding by Watson-Crick base pairing to standard polynucleotide bases, where the analog backbone presents the bases in a manner to permit such hydrogen bonding in a sequence-specific fashion between the oligonucleotide analog molecule and bases in a standard polynucleotide (e.g., single-stranded RNA or single-stranded DNA). Preferred analogs are those having a substantially uncharged, phosphorus containing backbone.

A substantially uncharged, phosphorus containing backbone in an oligonucleotide analog is one in which a majority of the subunit linkages, e.g., between 60-100%, are uncharged at physiological pH, and contain a single phosphorous atom. The analog contains between 8 and 40 subunits, typically about 8-25 subunits, and preferably about 12 to 25 subunits. The analog may have exact sequence complementarity to the target sequence or near complementarity, as defined below.

A "subunit" of an oligonucleotide analog refers to one nucleotide (or nucleotide analog) unit of the analog. The term may refer to the nucleotide unit with or without the attached intersubunit linkage, although, when referring to a "charged subunit", the charge typically resides within the intersubunit linkage (e.g. a phosphate or phosphorothioate linkage).

A "morpholino oligonucleotide analog" is an oligonucleotide analog composed of morpholino subunit structures of the form shown in FIGS. 1A-1D, where (i) the structures are linked together by phosphorus-containing linkages, one to three atoms long, joining the morpholino nitrogen of one subunit to the 5' exocyclic carbon of an adjacent subunit, and (ii) $P_i$ and $P_j$ are purine or pyrimidine base-pairing moieties effective to bind, by base-specific hydrogen bonding, to a base in a polynucleotide. The purine or pyrimidine base-pairing moiety is typically adenine, cytosine, guanine, uracil, thymine or inosine. The synthesis, structures, and binding characteristics of morpholino oligomers are detailed in U.S. Pat. Nos. 5,698,685, 5,217,866, 5,142,047, 5,034,506, 5,166, 315, 5,521,063, and 5,506,337, all of which are incorporated herein by reference.

Figure 1A:
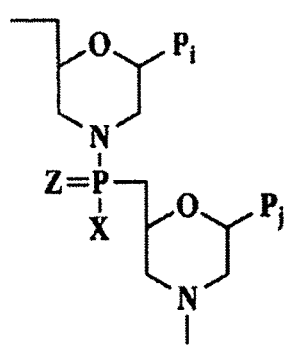
FIGS. 1A-1D show the repeating subunit segment of several preferred morpholino oligonucleotides, designated A through D, constructed using subunits having 5-atom (A), six-atom (B) and seven-atom (C-D) linking groups suitable for forming polymers.
Figure 1B:
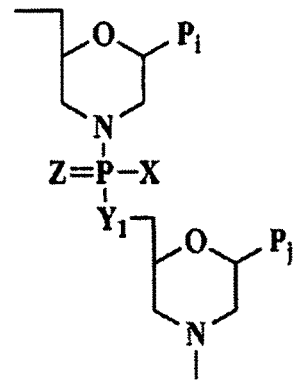

The subunit and linkage shown in FIG. 1B are used for six-atom repeating-unit backbones, as shown in FIG. 1B (where the six atoms include: a morpholino nitrogen, the connected phosphorus atom, the atom (usually oxygen) linking the phosphorus atom to the 5' exocyclic carbon, the 5' exocyclic carbon, and two carbon atoms of the next morpholino ring). In these structures, the atom $Y_1$ linking the 5' exocyclic morpholino carbon to the phosphorus group may be sulfur, nitrogen, carbon or, preferably, oxygen. The X moiety pendant from the phosphorus is any stable group which does not interfere with base-specific hydrogen bonding. Preferred X groups include fluoro, alkyl, alkoxy, thioalkoxy, and alkyl amino, including cyclic amines, all of which can be variously substituted, as long as base-specific bonding is not disrupted. Alkyl, alkoxy and thioalkoxy preferably include 1-6 carbon atoms. Alkyl amino preferably refers to lower alkyl ($C_1$ to $C_6$) substitution, and cyclic amines are preferably 5- to 7-membered nitrogen heterocycles optionally containing 1-2 additional heteroatoms selected from oxygen, nitrogen, and sulfur. Z is sulfur or oxygen, and is preferably oxygen.

A preferred morpholino oligomer is a phosphorodiamidate-linked morpholino oligomer, referred to herein as a PMO. Such oligomers are composed of morpholino subunit structures such as shown in FIG. 1B, where X=$NH_2$, NHR, or $NR_2$ (where R is lower alkyl, preferably methyl), Y=O, and Z=O, and $P_i$ and $P_j$ are purine or pyrimidine base-pairing moieties effective to bind, by base-specific hydrogen bonding, to a base in a polynucleotide. Also preferred are structures having an alternate phosphorodiamidate linkage, where, in FIG. 1B, X=lower alkoxy, such as methoxy or ethoxy, Y=NH or NR, where R is lower alkyl, and Z=O. A cationic linkage can be introduced into the backbone by utilizing X=(1-piperazino) as shown in FIG. 1B.

The term "substituted", particularly with respect to an alkyl, alkoxy, thioalkoxy, or alkylamino group, refers to replacement of a hydrogen atom on carbon with a heteroatom-containing substituent, such as, for example, halogen, hydroxy, alkoxy, thiol, alkylthio, amino, alkylamino, imino, oxo (keto), nitro, cyano, or various acids or esters such as carboxylic, sulfonic, or phosphonic. It may also refer to replacement of a hydrogen atom on a heteroatom (such as an amine hydrogen) with an alkyl, carbonyl or other carbon containing group.

As used herein, the term "target", relative to the viral genomic RNA, refers to at least one of the following: 1) a 125 nucleotide region that surrounds the AUG start codon of a viral messenger RNA and/or; 2) the terminal 30 bases of the 3' terminal end of the minus-strand viral RNA (e.g. virion RNA or vRNA) and/or; 3) the terminal 25 bases of viral mRNA transcripts The term "target sequence" refers to a portion of the target RNA against which the oligonucleotide analog is directed, that is, the sequence to which the oligonucleotide analog will hybridize by Watson-Crick base pairing of a complementary sequence. As will be seen, the target sequence may be a contiguous region of the viral positive-strand mRNA or the minus-strand vRNA.

The term "targeting sequence" is the sequence in the oligonucleotide analog that is complementary (meaning, in addition, substantially complementary) to the target sequence in the RNA genome. The entire sequence, or only a portion, of the analog compound may be complementary to the target sequence. For example, in an analog having 20 bases, only 12-14 may be targeting sequences. Typically, the targeting sequence is formed of contiguous bases in the analog, but may alternatively be formed of non-contiguous sequences that when placed together, e.g., from opposite ends of the analog, constitute sequence that spans the target sequence. For example, as will be seen, the target and targeting sequences are selected such that binding of the analog to a portion of a 125 nucleotide region associated with the AUG start codon of the positive-sense RNA strand (i.e., mRNA) of the virus acts to disrupt translation of the viral gene and reduce viral replication.

The term "AUG start site region" includes a 125 nucleotide region in both the 5' and 3' direction relative to the AUG start codon of viral mRNAs. The region includes about 25 nucleotides downstream (i.e., in a 3' direction) and 100 nucleotides upstream (i.e., in a 5' direction) as exemplified by the targets sequences shown as SEQ ID NOs: 1-6 for Ebola virus and SEQ ID NOs: 8-13 for Marburg virus.

Target and targeting sequences are described as "complementary" to one another when hybridization occurs in an antiparallel configuration. A targeting sequence may have "near" or "substantial" complementarity to the target sequence and still function for the purpose of the present invention, that is, still be "complementary." Preferably, the oligonucleotide analog compounds employed in the present invention have at most one mismatch with the target sequence out of 10 nucleotides, and preferably at most one mismatch out of 20. Alternatively, the antisense oligomers employed have at least 90% sequence homology, and preferably at least 95% sequence homology, with the exemplary targeting sequences as designated herein.

An oligonucleotide analog "specifically hybridizes" to a target polynucleotide if the oligomer hybridizes to the target under physiological conditions, with a $T_m$ substantially greater than 45° C., preferably at least 50° C., and typically 60° C.-80° C. or higher. Such hybridization preferably corresponds to stringent hybridization conditions. At a given ionic strength and pH, the $T_m$ is the temperature at which 50% of a target sequence hybridizes to a complementary polynucleotide. Again, such hybridization may occur with "near" or "substantial" complementary of the antisense oligomer to the target sequence, as well as with exact complementarity.

A "nuclease-resistant" oligomeric molecule (oligomer) refers to one whose backbone is substantially resistant to nuclease cleavage, in non-hybridized or hybridized form; by common extracellular and intracellular nucleases in the body; that is, the oligomer shows little or no nuclease cleavage under normal nuclease conditions in the body to which the oligomer is exposed.

A "heteroduplex" refers to a duplex between an oligonculeotide analog and the complementary portion of a target RNA. A "nuclease-resistant heteroduplex" refers to a heteroduplex formed by the binding of an antisense oligomer to its complementary target, such that the heteroduplex is substantially resistant to in vivo degradation by intracellular and extracellular nucleases, such as RNAseH, which are capable of cutting double-stranded RNA/RNA or RNA/DNA complexes.

A "base-specific intracellular binding event involving a target RNA" refers to the specific binding of an oligonucleotide analog to a target RNA sequence inside a cell. The base specificity of such binding is sequence specific. For example, a single-stranded polynucleotide can specifically bind to a single-stranded polynucleotide that is complementary in sequence.

An "effective amount" of an antisense oligomer, targeted against an infecting filovirus, is an amount effective to reduce the rate of replication of the infecting virus, and/or viral load, and/or symptoms associated with the viral infection.

As used herein, the term "body fluid" encompasses a variety of sample types obtained from a subject including, urine, saliva, plasma, blood, spinal fluid, or other sample of biological origin, such as skin cells or dermal debris, and may refer to cells or cell fragments suspended therein, or the liquid medium and its solutes.

The term "relative amount" is used where a comparison is made between a test measurement and a control measurement. The relative amount of a reagent forming a complex in a reaction is the amount reacting with a test specimen, compared with the amount reacting with a control specimen. The control specimen may be run separately in the same assay, or it may be part of the same sample (for example, normal tissue surrounding a malignant area in a tissue section).

"Treatment" of an individual or a cell is any type of intervention provided as a means to alter the natural course of the individual or cell. Treatment includes, but is not limited to, administration of e.g., a pharmaceutical composition, and may be performed either prophylactically, or subsequent to the initiation of a pathologic event or contact with an etiologic agent. The related term "improved therapeutic outcome" relative to a patient diagnosed as infected with a particular virus, refers to a slowing or diminution in the growth of virus, or viral load, or detectable symptoms associated with infection by that particular virus.

An agent is "actively taken up by mammalian cells" when the agent can enter the cell by a mechanism other than passive diffusion across the cell membrane. The agent may be transported, for example, by "active transport", referring to transport of agents across a mammalian cell membrane by e.g. an ATP-dependent transport mechanism, or by "facilitated transport", referring to transport of antisense agents across the cell membrane by a transport mechanism that requires binding of the agent to a transport protein, which then facilitates passage of the bound agent across the membrane. For both active and facilitated transport, the oligonucleotide analog preferably has a substantially uncharged backbone, as defined below. Alternatively, the antisense compound may be formulated in a complexed form, such as an agent having an anionic backbone complexed with cationic lipids or liposomes, which can be taken into cells by an endocytotic mechanism. The analog also may be conjugated, e.g., at its 5' or 3' end, to an arginine-rich peptide, e.g., a portion of the HIV TAT protein, or polyarginine, to facilitate transport into the target host cell as described (Moulton, Nelson et al. 2004). The compound may also have one or more cationic linkages to enhance antisense activity and/or cellular uptake. A preferred cationic linkage is shown in FIG. 1B where X=(1-piperazino).

The term "filovirus" refers collectively to members of the Filoviridae family of single stranded (−) RNA viruses including Ebola and Marburg viruses listed in Table 1 below.

II. Targeted Viruses

The present invention is based on the discovery that effective inhibition of single-stranded, negative-sense RNA ((−) RNA)viruses can be achieved by exposing cells infected with the virus to antisense oligonucleotide analog compounds (i) targeted against the AUG start codon of the positive sense viral mRNAs or the 3' termini of the negative strand viral RNA, and (ii) having physical and pharmacokinetic features which allow effective interaction between the antisense compound and the virus within host cells. In one aspect, the oligomers can be used in treating a mammalian subject infected with the virus.

The invention targets RNA viruses having genomes that are: (i) single stranded, (ii) negative polarity, and (iii) less than 20 kb. The targeted viruses also synthesize a RNA species with positive polarity, the positive-strand or sense RNA, as the requisite step in viral gene expression. In particular, targeted viruses include those of the Filoviridae family referred to herein as filoviruses. Targeted viruses organized by family, genus and species are listed in Table 1. Various physical, morphological, and biological characteristics of each of the Filoviridae family, and members therein, can be found, for example, in Textbook of Human Virology, R. Belshe, ed., 2$^{nd}$ Edition, Mosby, 1991, in "Viruses and Human Disease" (Strauss and Strauss 2002) and at the Universal Virus Database of the International Committee on Taxonomy of Viruses (www.ncbi.nlm.nih.gov/ICTVdb/index.htm). Some of the key biological characteristics of each family are summarized below following Table 1.

TABLE 1

Targeted viruses of the invention organized by family and genus

| Family | Genus | Virus |
| --- | --- | --- |
| Filoviridae | Marburg-like | Marburg virus (MARV) |
| | Ebola-like | Zaire Ebola virus (ZEBOV) |
| | | Sudan Ebola virus (SEBOV) |
| | | Reston Ebola virus (REBOV) |
| | | Cote d'Ivoire Ebola (ICEBOV) |

A. Filoviridae

The Filoviridae family is composed of two members, Ebola virus (EBOV) and Marburg virus (MARV). Four species of Ebola have been identified to date and are named by the location of where they were identified including Ebola Ivory Coast (ICEBOV), Ebola Zaire (ZEBOV), Ebola Sudan (SEBOV) and Ebola Reston (REBOV). Ebola Reston is the only known filovirus that does not cause severe human disease. The filovirus structure is pleomorphic with shapes varying from long filaments to shorter contorted structures. The viral filaments measure up to 14,000 nm in length and have uniform diameter of 80 nm. The virus filament is envelope in a lipid membrane. The virion contains one, single-stranded, negative sense RNA.

The first filovirus was recognized in 1967 after laboratory workers in Marburg Germany developed hemorrhagic fever following studies involving handling tissues from green monkeys. The Marburg outbreak led to 31 cases and seven deaths. The first Ebola virus was identified in 1976 following outbreaks of Ebola hemorrhagic fever in northern Zaire (now the Democratic Republic of Congo) and southern Sudan. Eventually, two distinct viral isolates were recognized. Ebola Zaire was lethal in 90% of the infected cases and Ebola Sudan was lethal in 50% of the cases. A list of Ebola hemorrhagic fever case is compiled for Ebola Zaire in TABLE 2.

TABLE 2

Chronological order of Ebola Zaire Outbreaks

| Date | Location | Human Cases | Deaths |
| --- | --- | --- | --- |
| 1976 | Zaire | 318 | 280 (88%) |
| 1977 | Zaire | 1 | 1 (100%) |
| 1994 | Gabon | 49 | 29 (59%) |
| 1995 | Dem. Rep. Congo | 315 | 255 (81%) |
| 1996 | Gabon | 31 | 21 (68%) |
| 1996 | Gabon | 60 | 45 (75%) |
| 1996 | South Africa | 2 | 1 (50%) |
| 2001 | Gabon and Congo | 122 | 96 (79%) |

The summary of these outbreak data include 899 cases resulting in 728 deaths or an overall 81% rate of lethality observed over a period of 25 years. A single case of Ebola Ivory Coast was reported in 1994 and that infection was not lethal. Finally, 4 outbreaks of Ebola Sudan from 1976 to 2001 produced 744 cases resulting in 398 deaths or an overall rate of lethality of 53%. These observations indicate Ebola Zaire is the virus of greatest concern both in apparent prevalence and lethality. It appears Ebola is transmitted to humans from ongoing life cycles in animals other than humans which make it a zoonotic virus. Ebola can replicate in various rodents such as mice, guinea pigs and some species of bats. Some types of bats are native to areas where the virus is found which suggests the bat may be the natural host and viral reservoir. Once a human is infected, person-to-person transmission is the means for further infections. During recorded outbreaks, individuals that cared for or worked closely with infected people were at high risk of becoming infected. Nosocomial transmission has also been an important factor in the spread of viral infection during outbreaks. In the laboratory setting, viral spread through small-particle aerosols has been clearly demonstrated.

The incubation period for Ebola hemorrhagic fever ranges from 2 to 21 days. The clinical symptoms include abrupt onset of fever, headache, joint and muscle aches, sore throat and weakness. These symptoms are then followed by diarrhea, vomiting and stomach pain which do not help in diagnosis of infection. Diagnosis is suspected when this group of symptoms is observed in an area where Ebola is known to be active. Patients who die usually have not developed a significant immune response to the virus at the time of death. There are no known treatments for filovirus infections.

Figure 3A:
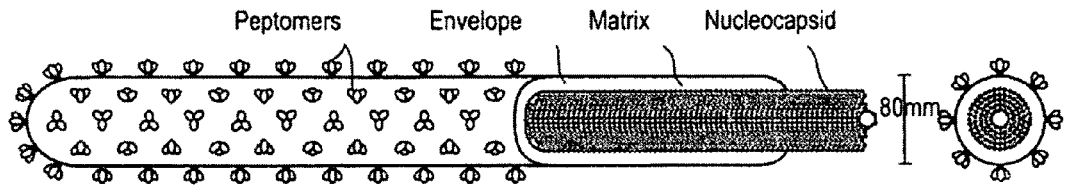
FIGS. 3A-3C illustrate the components and morphology of a filovirus (3A), and show the arrangement of viral genes in the Ebola virus (Zaire) (3B), and the Marburg virus (3C).
Figure 3B:
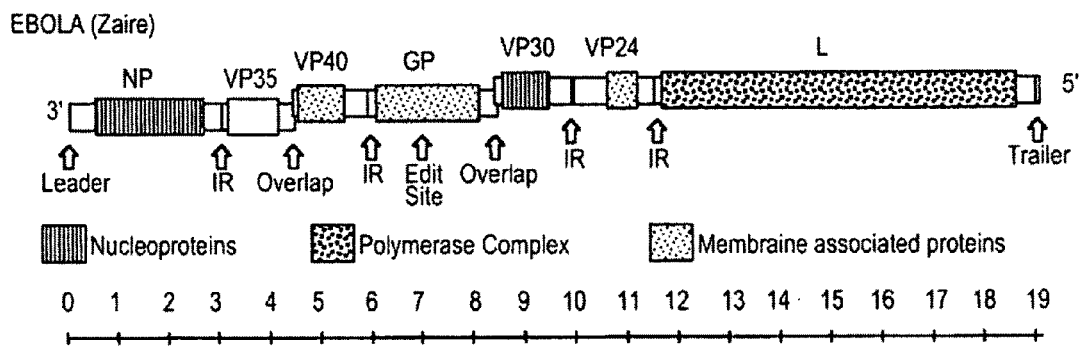
Figure 3C:
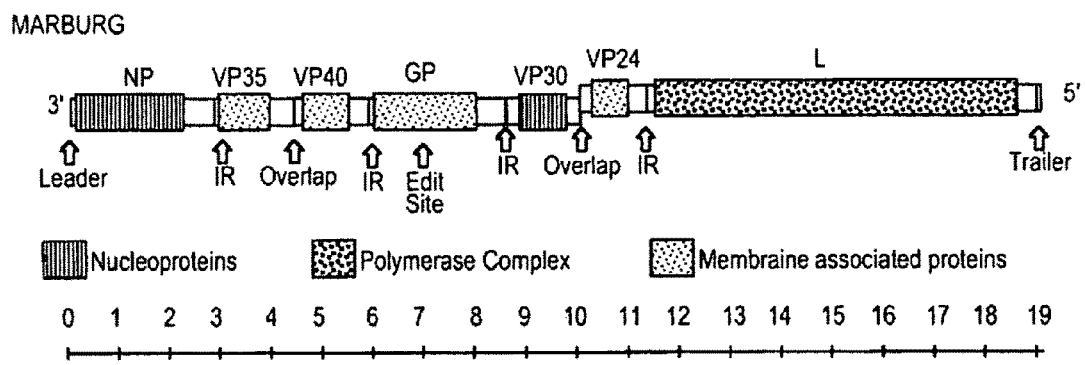

The filovirus virus genome is approximately 19,000 bases of single-stranded RNA that is unsegmented and in the antisense (i.e. negative sense) orientation. The genome encodes 7 proteins from monocistronic mRNAs complementary to the vRNA as shown in FIG. 3. A review of filoviruses can be found in Fields Virology and (Strauss and Strauss 2002).

Ebola Virus

Ebola virus (EBOV), a member of the family *Filoviridae* and the order Mononegavirales, is an enveloped, nonsegmented negative-strand RNA virus and is one of the most lethal human and nonhuman primate pathogens recognized to date. Four subtypes of Ebola virus have been identified, including Zaire (ZEBOV), Sudan (SEBOV), Ivory Coast (ICEBOV), and Reston (REBOV) (Sanchez, Kiley et al. 1993). Human infection with subtype Zaire causes a fulminating, febrile, hemorrhagic disease resulting in extensive mortality (Feldmann, Klenk et al. 1993; Peters and LeDuc 1999; Feldmann, Jones et al. 2003).

Ebola virus particles have a filamentous appearance, but their shape may be branched, circular, U- or 6-shaped, or long and straight. Virions show a uniform diameter of approximately 80 nm, but vary greatly in length. Ebola virus particles consist of seven structural proteins. The glycoprotein (GP) of Ebola virus forms spikes of approximately 7 nm, which are spaced at 5- to 10-nm intervals on the virion surface.

Marburg Virus

Marburg virus (MARV) was first recognized in 1967, when an outbreak of hemorrhagic fever in humans occurred in Germany and Yugoslavia, after the importation of infected monkeys from Uganda. Thirty-one cases of MARV hemorrhagic fever were identified that resulted in seven deaths. The filamentous morphology of the virus was later recognized to be characteristic, not only of additional MARV isolates, but also of EBOV. MARV and EBOV are now known to be distinctly different lineages in the family Filoviridae, within the viral order Mononegavirales (Strauss and Strauss 2002).

Few natural outbreaks of MARV disease have been recognized, and all proved self-limiting, with no more than two cycles of human-to-human transmission.

However, the actual risks posed by MARV to global health cannot be assessed because factors which restrict the virus to its unidentified ecological niche in eastern Africa, and those that limit its transmissibility, remain unknown. Concern about MARV is further heightened by its known stability and infectivity in aerosol form. A recent (2005) epidemic in eastern Africa caused at least 200 deaths and further increases the concern about MARV.

B. Target Sequences

The filovirus structure is pleomorphic with shapes varying from long filaments to shorter contorted structures. The viral filaments measure up to 14,000 nm in length and have uniform diameter of 80 nm. The virus filament is envelope in a lipid membrane. The virion contains one, single-stranded, negative sense RNA. The filovirus virus genome is approximately 19,000 bases of single- stranded RNA that is unsegmented and in the antisense orientation. The genome encodes 7 proteins from monocistronic mRNAs complementary to the vRNA. A diagram of a representative filovirus and its genome is provided in FIGS. 3A-3C (taken from Fields Virology).

The targets selected were positive-strand (sense) RNA sequences that span or are just downstream (within 25 bases) or upstream (within 100 bases) of the AUG start codon of selected Ebola virus proteins or the 3' terminal 30 bases of the minus-strand viral RNA. Preferred protein targets are the viral polymerase subunits VP35 and L, nucleoproteins NP and VP30, and membrane-associated proteins VP24 and VP40. Among these early proteins are favored, e.g., VP35 is favored over the later expressed L polymerase. As will be seen, a preferred single-compound target is VP35 that spans the AUG start site, and/or targets a region within 100 bases upstream or 25 bases downstream of the translational start site. Preferred combinations of targets include the VP35-AUG target plus the VP24-AUG start site (or the 100-base region upstream or 25-base-region downstream of the start site) and or the L polymerase AUG start site (or the 100-base region upstream or 25-base-region downstream of the start site).

Additional targets include the terminal 25 base pair region of the viral mRNA transcripts as represented by the sequences complementary to the SEQ ID NOs:42 and 43. These targets are preferred because of their high degree of sequence conservation across individual filovirus isolates.

The Ebola virus RNA sequences (Zaire Ebola virus, Mayinga strain) can be obtained from GenBank Accession No. AF086833. The particular targeting sequences shown below were selected for specificity against the Ebola Zaire virus strain. Corresponding sequences for Ebola Ivory Coast, Ebola Sudan and Ebola Reston (GenBank Acc. No. AF522874) are readily determined from the known GenBank entries for these viruses. Preferably targeting sequences are selected that give a maximum consensus among the viral strains, particularly the Zaire, Ivory Coast, and Sudan strains, or base mismatches that can be accommodated by ambiguous bases in the antisense sequence, according to well-known base pairing rules.

GenBank references for exemplary viral nucleic acid sequences representing filovirus genomic segments are listed in Table 3 below. The nucleotide sequence numbers in Table 3 are derived from the GenBank reference for the positive-strand RNA of Ebola Zaire (AF086833) and Marburg virus (Z29337). It will be appreciated that these sequences are only illustrative of other sequences in the Filoviridae family, as may be available from available gene-sequence databases of literature or patent resources (See e.g. www.ncbi.nlm.nih.gov). The sequences in Table 3 below, identified as SEQ ID NOs: 1-14, are also listed in the Sequence Listing table at the end of the specification.

The target sequences in Table 3 represent the 3' terminal 30 bases of the negative sense viral RNA or the 125 bases surrounding the AUG start codons of the indicated filovirus genes. The sequences shown are the positive-strand (i.e., antigenomic or mRNA) sequence in the 5' to 3' orientation. It will be obvious that when the target is the minus-strand vRNA, as in the case of the Str Inh 1 target (SEQ ID NOs: 15 and 44) the targeted sequence is the complement of the sequence listed in Table 3.

Table 3 lists the targets for exemplary Ebola viral genes VP35, VP24, VP30, VP40, L and NP. The proteins represent six of the seven proteins encoded by Ebola. The target sequences for the AUG start codons of the six genes are represented as SEQ ID NOs:1-6. The corresponding set of target sequences for Marburg virus are shown as SEQ ID NOs:8-13. The 3' terminal sequence of the minus-strand viral RNA (SEQ ID NOs:7 and 14) can also be targeted. The sequences shown in Table 3 for the 3' terminal minus-strand targets (SEQ ID NOs:7 and 14) are the minus-strand sequences in a 5'-3' orientation for Ebola and Marburg viruses, respectively.

TABLE 3

Exemplary Filovirus Nucleic Acid Target Sequences

| Name | GenBank No. | Nucleotide Region | Sequence (5' to 3') | SEQ ID NO |
|---|---|---|---|---|
| VP35-AUG | AF086833 | 3029-3153 | AAUGAUGAAGAUUAAAACCUUCAUCAUCCUUACGUCAAUUGAAUUCUCUAGCACUCGAAGCUUAUUGUCUUCAAUGUAAAAGAAAAGCUGGUCUAACAAGAUGACAACUAGAACAAAGGGCAGGG | 1 |
| VP24-AUG | AF086833 | 10245-10369 | CGUUCCAACAAUCGAGCGCAAGGUUUCAAGGUUGAACUGAGAGUGUCUAGACAACAAAAUAUUGAUACUCCAGACACCAAGCAAGACCUGAGAAAAACCAUGGCUAAAGCUACGGGACGAUACA | 2 |
| VP30-AUG | AF086833 | 8409-8533 | AGAUCUGCGAACCGGUAGAGUUUAGUUGCAACCUAACACACAUAAAGCAUUGGUCAAAAAGUCAAUAGAAAUUUAAACAGUGAGUGGAGACAACUUUUAAAUGGAAGCUUCAUAUGAGAGAGGAC | 3 |
| VP40-AUG | AF086833 | 4379-4503 | AAACCAAAAGUGAUGAAGAUUAAGAAAAACCUACCUCGGCUGAGAGAGUGUUUUUUCAUUAACCUUCAUCUUGUAAACGUUGAGCAAAAUUGUUAAAAAUAUGAGGCGGGUUAUAUUGCCUACUG | 4 |
| L-AUG | AF086833 | 11481-11605 | GUAGAUUAAGAAAAAAGCCUGAGGAAGAUUAAGAAAAACUGCUUAUUGGGUCUUUCCGUGUUUUAGAUGAAGCAGUUGAAAUUCUUCCUCUUGAUAUUAAAUGGCUACACAACAUACCCAAUAC | 5 |
| NP-AUG | AF086833 | 370-494 | UGAACACUUAGGGGAUUGAAGAUUCAACAACCCUAAAGCUUGGGGUAAAACAUUGGAAAUAGUUAAAAGACAAAUUGCUCGGAAUCACAAAAAUUCCGAGUAUGGAUUCUCGUCCUCAGAAAAUCU | 6 |
| Str Ihn 1(-) | AF086833 | 30-1 | UAAAAAUUCUUCUUUCUUUUUGUGUGUCCG | 7 |
| VP35-AUG | Z29337 | 2844-2968 | CUAAAAAUCGAAGAAUAUUAAAGGUUUUCUUUAAUAUUCAGAAAAGGUUUUUUAUUCUCUUCUUUCUUUUUGCAAACAUAUUGAAAUAAUAAUUUUCACAAUGUGGGACUCAUCAUAUAUGCAAC | 8 |
| VP24-AUG | Z29337 | 10105-10229 | UUCAUUCAAACACCCCAAAUUUUCAAUCAUACACAUAAUAACCAUUUUAGUAGCGUUACCUUUCAAUACAAUCUAGGUGAUUGUGAAAAGACUUCCAAACAUGGCAGAAUUAUCAACGCGUUACA | 9 |
| VP30-AUG | Z29337 | 8767-8891 | GAAGAACAUUAAGUGUUCUUUGUUAGAAUUAUUCAUCCAAGUUGUUUUGAGUAUACUCGCUUCAAUACAACUUCCCUUCAUAUUUGAUUCAAGAUUUAAAUGCAACAACCCCGUGGAAGGAGU | 10 |
| VP40-AUG | Z29337 | 4467-4591 | UCCCAAUCUCAGCUUGUUGAAUUAAUUGUUACUUAAGUCAUUCUUUUUAAAAUUAAUUCACACAAGGUAGUUUGGGUUUAUAUCUAGAACAAAUUUUAAUAUGGCCAGUUCCAGCAAUUACAACA | 11 |
| L-AUG | Z29337 | 11379-11503 | UCAUUCUCUUCGAUACACGUUAUAUCUUUUAGCAAAGUAAUGAAAAUAGCCUUGUCAUGUUUAGACGCCAGUUAUCCAUCUUAAGUGAAUCCUUUCUUCAAUAUGCAGCAUCCAACUCAAUAUCCUG | 12 |
| NP-AUG | Z29337 | 3-127 | CACACAAAAACAAGAGAUGAUGAUUUUGUGUAUCAUAUAAAUAAAGGAGAAUAUUAACAUUGACAUUGAGACUUGUCAGUCUGUUAAUAUUCUUGAAAAGAUGGAUUUACAUAGCUUGUUAGAGU | 13 |

TABLE 3-continued

Exemplary Filovirus Nucleic Acid Target Sequences

| Name | GenBank No. | Nucleotide Region | Sequence (5' to 3') | SEQ ID NO |
|---|---|---|---|---|
| Str Ihn 1(-) | Z29337 | 30-1 | CAAAAUCAUCAUCUCUUGUUUUUGUGUGUC | 14 |

Targeting sequences are designed to hybridize to a region of the target sequence as listed in Table 3. Selected targeting sequences can be made shorter, e.g., 12 bases, or longer, e.g., 40 bases, and include a small number of mismatches, as long as the sequence is sufficiently complementary to allow hybridization with the target, and forms with either the virus positive-strand or minus-strand, a heteroduplex having a $T_m$ of 45° C. or greater.

More generally, the degree of complementarity between the target and targeting sequence is sufficient to form a stable duplex. The region of complementarity of the antisense oligomers with the target RNA sequence may be as short as 8-11 bases, but is preferably 12-15 bases or more, e.g. 12-20 bases, or 12-25 bases. An antisense oligomer of about 14-15 bases is generally long enough to have a unique complementary sequence in the viral genome. In addition, a minimum length of complementary bases may be required to achieve the requisite binding $T_m$, as discussed below.

Oligomers as long as 40 bases may be suitable, where at least the minimum number of bases, e.g., 8-11, preferably 12-15 bases, are complementary to the target sequence. In general, however, facilitated or active uptake in cells is optimized at oligomer lengths less than about 30, preferably less than 25, and more preferably 20 or fewer bases. For PMO oligomers, described further below, an optimum balance of binding stability and uptake generally occurs at lengths of 18-25 bases.

The oligomer may be 100% complementary to the viral nucleic acid target sequence, or it may include mismatches, e.g., to accommodate variants, as long as a heteroduplex formed between the oligomer and viral nucleic acid target sequence is sufficiently stable to withstand the action of cellular nucleases and other modes of degradation which may occur in vivo. Oligomer backbones which are less susceptible to cleavage by nucleases are discussed below. Mismatches, if present, are less destabilizing toward the end regions of the hybrid duplex than in the middle. The number of mismatches allowed will depend on the length of the oligomer, the percentage of G:C base pairs in the duplex, and the position of the mismatch(es) in the duplex, according to well understood principles of duplex stability. Although such an antisense oligomer is not necessarily 100% complementary to the viral nucleic acid target sequence, it is effective to stably and specifically bind to the target sequence, such that a biological activity of the nucleic acid target, e.g., expression of viral protein(s), is modulated.

The stability of the duplex formed between the oligomer and the target sequence is a function of the binding $T_m$ and the susceptibility of the duplex to cellular enzymatic cleavage. The $T_m$ of an antisense compound with respect to complementary-sequence RNA may be measured by conventional methods, such as those described by Hames et al., Nucleic Acid Hybridization, IRL Press, 1985, pp. 107-108 or as described in Miyada C. G. and Wallace R. B., 1987, Oligonucleotide hybridization techniques, Methods Enzymol. Vol. 154 pp. 94-107. Each antisense oligomer should have a binding $T_m$, with respect to a complementary-sequence RNA, of greater than body temperature and preferably greater than 50° C. $T_m$'s in the range 60-80° C. or greater are preferred. According to well known principles, the $T_m$ of an oligomer compound, with respect to a complementary-based RNA hybrid, can be increased by increasing the ratio of C:G paired bases in the duplex, and/or by increasing the length (in base pairs) of the heteroduplex. At the same time, for purposes of optimizing cellular uptake, it may be advantageous to limit the size of the oligomer. For this reason, compounds that show high $T_m$ (50° C. or greater) at a length of 20 bases or less are generally preferred over those requiring greater than 20 bases for high $T_m$ values.

Table 4 below shows exemplary targeting sequences, in a 5'-to-3' orientation, that target the Ebola Zaire virus (GenBank Acc. No. AF086833) according to the guidelines described above. The sequences listed provide a collection of targeting sequences from which additional targeting sequences may be selected, according to the general class rules discussed above. SEQ ID NOs:16-43 are antisense to the positive strand (mRNA) of the virus whereas SEQ ID NO:15 is antisense to the minus strand viral RNA.

TABLE 4

Exemplary Antisense Oligomer Sequences Targeting Ebola Zaire

| Name | Target GenBank No. AF086833 | Sequence 5'-3' | SEQ ID NO |
|---|---|---|---|
| Str. Inh. 1 | 1-22 (-) strand | CGGACACACAAAAAGAAAGAAG | 15 |
| L-AUG | 11588-11567 | GTAGCCATTTAATATCAAGAGG | 16 |
| L'-AUG | 11581-11600 | TGGGTATGTTGTGTAGCCAT | 17 |
| L-29-AUG | 11552-11573 | CAAGAGGAAGAATTTCAACTGC | 18 |
| L + 4-AUG | 11584-11604 | GTATTGGGTATGTTGTGTAGC | 19 |
| L + 11-AUG | 11591-11611 | CGTCTGGGTATTGGGTATGTT | 20 |

TABLE 4-continued

Exemplary Antisense Oligomer Sequences Targeting Ebola Zaire

| Name | Target GenBank No. AF086833 | Sequence 5'-3' | SEQ ID NO |
|---|---|---|---|
| VP35-AUG | 3136-3115 | GTTGTCATCTTGTTAGACCAGC | 21 |
| VP35'-AUG | 3133-3152 | CCTGCCCTTTGTTCTAGTTG | 22 |
| VP35-22-AUG | 3032-3053 | GATGAAGGTTTTAATCTTCATC | 23 |
| VP35-19-AUG | 3115-3133 | GTCATCTTGTAGACCAGC | 24 |
| VP35-16-AUG | 3118-3133 | GTCATCTTGTTAGACC | 25 |
| VP35 + 2-AUG | 3131-3152 | CCTGCCCTTTGTTCTAGTTGTC | 26 |
| NP-AUG | 464-483 | GGACGAGAATCCATACTCGG | 27 |
| NP + 4-AUG | 473-495 | CAGATTTTCTGAGGACGAGAATC | 28 |
| NP + 11-AUG | 480-499 | CATCCAGATTTTCTGAGGAC | 29 |
| NP + 18-AUG | 487-507 | CTCGGCGCCATCCAGATTTTC | 30 |
| NP-19-AUG | 451-472 | CATACTCGGAATTTTGTGATTC | 31 |
| VP40-AUG | 4481-4498 | GGCAATATAACCCGCCTC | 32 |
| VP30-AUG | 8494-8512 | CCATTTAAAAGTTGTCTCC | 33 |
| VP24-AUG | 10331-10349 | GCCATGGTTTTTTCTCAGG | 34 |
| VP24-28-AUG | 10317-10336 | CTCAGGTCTTGCTTGGTGTC | 35 |
| VP24 + 4-AUG | 10348-10369 | TGTATCGTCCCGTAGCTTTAGC | 36 |
| VP24 + 10-AUG | 10354-10372 | GATTGTATCGTCCCGTAGC | 37 |
| VP24 + 19-AUG | 10361-10382 | GGCGATATTAGATTGTATCGTC | 38 |
| VP24-5'trm | 10261-10280 | TTCAACCTTGAAACCTTGCG | 39 |
| VP24(8+)-AUG | 10331-10349 | GCCA+TGG+T+T+T+T+T+TC+TCAGG | 40 |
| VP24-5'trm(6+) | 10261-10280 | +T+TCAACC+T+TGAAACC+T+T-TGCG | 41 |
| panVP35 | 3032-3053 | GATGAAGGTTTTAATCTTCATC | 42 |
| Ser/3 | 4390-4407 8288-8305 | TTTTTCTTAATCTTCATC | 43 |

In Table 4, above, SEQ ID NOs:40 and 41 are shown with cationic linkages (+) wherein X=(1-piperazino) as shown in FIG. 1B and FIG. 2H. Also in Table 4, above, SEQ ID NOs: 42 and 43 correspond to antisense oligomers that target the 5' terminal nucleotide region of the Ebola virus VP35 mRNA (SEQ ID NO:42) and the 5' terminal nucleotide region of both the Ebola virus VP40 and VP30 mRNAs (SEQ ID NO:43).

Table 5 below shows exemplary targeting sequences, in a 5'-to-3' orientation, that target the Marburg virus (GenBank Acc. No. Z29337) according to the guidelines described above. The sequences listed provide a collection of targeting sequences from which additional targeting sequences may be selected, according to the general class rules discussed above. SEQ ID NOs:45-58 are antisense to the positive strand (mRNA) of the virus whereas SEQ ID NO:44 is antisense to the minus strand viral RNA.

TABLE 5

Exemplary Antisense Oligomer Sequences Targeting Marburg Virus

| Name | Target GenBank No. Z29337 | Sequence 5'-3' | SEQ ID NO |
|---|---|---|---|
| (-)3'term | 1-21 (-) | GACACACAAAAACAAGAGATG | 44 |
| L-AUG | 11467-11485 | GCTGCATATTGAAGAAAGG | 45 |
| L + 7-AUG | 11485-11506 | CATCAGGATATTGAGTTGGATG | 46 |

TABLE 5-continued

Exemplary Antisense Oligomer Sequences Targeting Marburg Virus

| Name | Target GenBank No. Z29337 | Sequence 5'-3' | SEQ ID NO |
|---|---|---|---|
| VP35-AUG | 2932-2952 | GTCCCACATTGTGAAAATTAT | 47 |
| VP35 + 7-AUG | 2950-2971 | CTTGTTGCATATATGATGAGTC | 48 |
| NP-AUG | 94-112 | GTAAATCCATCTTTTCAAG | 49 |
| NP-6-AUG | 97-120 | CAAGCTATGTAAATCCATCTTTTC | 50 |
| NP + 4-AUG | 106-124 | CCTAACAAGCTATGTAAATC | 51 |
| NP-5'SL | 68-88 | TAACAGACTGACAAGTCTCAA | 52 |
| NP-5'UTR | 44-64 | CAATGTTAATATTCTTCTTTA | 53 |
| NP-5'UTRb | 36-56 | ATATTCTTCTTTATTTATATGT | 54 |
| VP30-AUG | 8852-8873 | GTTGCATTTTAAATCTTGAATC | 55 |
| VP35-5'UTR | 2848-2867 | CCTTTAATATTCTTCGATTT | 56 |
| VP24 + 5-AUG | 10209-10231 | GTTGTAACGCGTTGATAATTCTG | 57 |
| NP-stem loop | 58-77 | CAAGTCTCAATGTCAATGTT | 58 |

III. Antisense Oligonucleotide Analog Compounds

A. Properties

As detailed above, the antisense oligonucleotide analog compound (the term “antisense” indicates that the compound is targeted against either the virus’ positive-sense strand RNA or negative-sense or minus-strand) has a base sequence target region that includes one or more of the following: 1) 125 bases surrounding the AUG start codons of viral mRNA and/or; 2) 30 bases at the 3' terminus of the minus strand viral RNA and/or; 3) 25 bases at the 5' terminus of viral mRNA transcripts. In addition, the oligomer is able to effectively target infecting viruses, when administered to a host cell, e.g. in an infected mammalian subject. This requirement is met when the oligomer compound (a) has the ability to be actively taken up by mammalian cells, and (b) once taken up, form a duplex with the target RNA with a $T_m$ greater than about 45° C.

As will be described below, the ability to be taken up by cells requires that the oligomer backbone be substantially uncharged, and, preferably, that the oligomer structure is recognized as a substrate for active or facilitated transport across the cell membrane. The ability of the oligomer to form a stable duplex with the target RNA will also depend on the oligomer backbone, as well as factors noted above, the length and degree of complementarity of the antisense oligomer with respect to the target, the ratio of G:C to A:T base matches, and the positions of any mismatched bases. The ability of the antisense oligomer to resist cellular nucleases promotes survival and ultimate delivery of the agent to the cell cytoplasm.

Below are disclosed methods for testing any given, substantially uncharged backbone for its ability to meet these requirements.

B. Active or Facilitated Uptake by Cells

The antisense compound may be taken up by host cells by facilitated or active transport across the host cell membrane if administered in free (non-complexed) form, or by an endocytotic mechanism if administered in complexed form.

In the case where the agent is administered in free form, the antisense compound should be substantially uncharged, meaning that a majority of its intersubunit linkages are uncharged at physiological pH. Experiments carried out in support of the invention indicate that a small number of net charges, e.g., 1-2 for a 15- to 20-mer oligomer, can in fact enhance cellular uptake of certain oligomers with substantially uncharged backbones. The charges may be carried on the oligomer itself, e.g., in the backbone linkages, or may be terminal charged-group appendages. Preferably, the number of charged linkages is no more than one charged linkage per four uncharged linkages. More preferably, the number is no more than one charged linkage per ten, or no more than one per twenty, uncharged linkages. In one embodiment, the oligomer is fully uncharged.

An oligomer may also contain both negatively and positively charged backbone linkages, as long as opposing charges are present in approximately equal number. Preferably, the oligomer does not include runs of more than 3-5 consecutive subunits of either charge. For example, the oligomer may have a given number of anionic linkages, e.g. phosphorothioate or N3'→P5' phosphoramidate linkages, or cationic linkages, such as N,N-diethylenediamine phosphoramidates (Dagle, Littig et al. 2000) or 1-piperazino phosphoramidates (FIG. 2H). The net charge is preferably neutral or at most 1-8 net charges per oligomer.

In addition to being substantially or fully uncharged, the antisense agent is preferably a substrate for a membrane transporter system (i.e. a membrane protein or proteins) capable of facilitating transport or actively transporting the oligomer across the cell membrane. This feature may be determined by one of a number of tests for oligomer interaction or cell uptake, as follows.

A first test assesses binding at cell surface receptors, by examining the ability of an oligomer compound to displace or be displaced by a selected charged oligomer, e.g., a phosphorothioate oligomer, on a cell surface. The cells are incubated with a given quantity of test oligomer, which is typically fluorescently labeled, at a final oligomer concentration of between about 10-300 nM. Shortly thereafter, e.g., 10-30 minutes (before significant internalization of the test oligomer can occur), the displacing compound is added, in incrementally increasing concentrations. If the test compound is able to bind to a cell surface receptor, the displacing compound will be observed to displace the test compound. If the displacing compound is shown to produce 50% displacement at a concentration of 10X the test compound concentration or less, the test compound is considered to bind at the same recognition site for the cell transport system as the displacing compound.

A second test measures cell transport, by examining the ability of the test compound to transport a labeled reporter, e.g., a fluorescence reporter, into cells. The cells are incubated in the presence of labeled test compound, added at a final concentration between about 10-300 nM. After incubation for 30-120 minutes, the cells are examined, e.g., by microscopy, for intracellular label. The presence of significant intracellular label is evidence that the test compound is transported by facilitated or active transport.

The antisense compound may also be administered in complexed form, where the complexing agent is typically a polymer, e.g., a cationic lipid, polypeptide, or non-biological cationic polymer, having an opposite charge to any net charge on the antisense compound. Methods of forming complexes, including bilayer complexes, between anionic oligonucleotides and cationic lipid or other polymer components, are well known. For example, the liposomal composition Lipofectin® (Felgner, Gadek et al. 1987), containing the cationic lipid DOTMA (N-[1-(2,3-dioleyloxy)propyl]-N,N,N-trimethylammonium chloride) and the neutral phospholipid DOPE (dioleyl phosphatidyl ethanolamine), is widely used. After administration, the complex is taken up by cells through an endocytotic mechanism, typically involving particle encapsulation in endosomal bodies.

The antisense compound may also be administered in conjugated form with an arginine-rich peptide linked covalently to the 5' or 3' end of the antisense oligomer. The peptide is typically 8-16 amino acids and consists of a mixture of arginine, and other amino acids including phenylalanine and cysteine. The use of arginine-rich peptide-PMO conjugates can be used to enhance cellular uptake of the antisense oligomer (See, e.g. (Moulton, Nelson et al. 2004; Nelson, Stein et al. 2005). Exemplary arginine-rich peptides are listed as SEQ ID NOs:61-66 in the Sequence Listing.

In some instances, liposomes may be employed to facilitate uptake of the 30 antisense oligonucleotide into cells. (See, e.g., Williams, S. A., Leukemia 10(12): 1980-1989, 1996; Lappalainen et al., Antiviral Res. 23:119, 1994; Uhlmann et al., "Antisense oligonucleotides: A new therapeutic principle," Chemical Reviews, Volume 90, No. 4, pages 544-584, 1990; Gregoriadis, G., Chapter 14, Liposomes, Drug Carriers in Biology and Medicine, pp. 287-341, Academic Press, 1979). Hydrogels may also be used as vehicles for antisense oligomer administration, for example, as described in WO 93/01286. Alternatively, the oligonucleotides may be administered in microspheres or microparticles. (See, e.g., Wu, G. Y. and Wu, C. H., J. Biol. Chem. 262:4429-4432, 1987). Alternatively, the use of gas-filled microbubbles complexed with the antisense oligomers can enhance delivery to target tissues, as described in U.S. Pat. No. 6,245,747.

Alternatively, and according to another aspect of the invention, the requisite properties of oligomers with any given backbone can be confirmed by a simple in vivo test, in which a labeled compound is administered to an animal, and a body fluid sample, taken from the animal several hours after the oligomer is administered, assayed for the presence of heteroduplex with target RNA. This method is detailed in subsection D below.

C. Substantial Resistance to RNAseH

Two general mechanisms have been proposed to account for inhibition of expression by antisense oligonucleotides. (See e.g., (Agrawal, Mayrand et al. 1990; Bonham, Brown et al. 1995; Boudvillain, Guerin et al. 1997). In the first, a heteroduplex formed between the oligonucleotide and the viral RNA acts as a substrate for RNaseH, leading to cleavage of the viral RNA. Oligonucleotides belonging, or proposed to belong, to this class include phosphorothioates, phosphotriesters, and phosphodiesters (unmodified "natural" oligonucleotides). Such compounds expose the viral RNA in an oligomer:RNA duplex structure to hydrolysis by RNaseH, and therefore loss of function.

A second class of oligonucleotide analogs, termed "steric blockers" or, alternatively, "RNaseH inactive" or "RNaseH resistant", have not been observed to act as a substrate for RNaseH, and are believed to act by sterically blocking target RNA nucleocytoplasmic transport, splicing or translation. This class includes methylphosphonates (Toulme, Tinevez et al. 1996), morpholino oligonucleotides, peptide nucleic acids (PNA's), certain 2'-O-allyl or 2'-O-alkyl modified oligonucleotides (Bonham, Brown et al. 1995), and N3'→P5' phosphoramidates (Ding, Grayaznov et al. 1996; Gee, Robbins et al. 1998).

A test oligomer can be assayed for its RNaseH resistance by forming an RNA:oligomer duplex with the test compound, then incubating the duplex with RNaseH under a standard assay conditions, as described in Stein et al. After exposure to RNaseH, the presence or absence of intact duplex can be monitored by gel electrophoresis or mass spectrometry.

D. In vivo Uptake

In accordance with another aspect of the invention, there is provided a simple, rapid test for confirming that a given antisense oligomer type provides the required characteristics noted above, namely, high $T_m$, ability to be actively taken up by the host cells, and substantial resistance to RNaseH. This method is based on the discovery that a properly designed antisense compound will form a stable heteroduplex with the complementary portion of the viral RNA target when administered to a mammalian subject, and the heteroduplex subsequently appears in the urine (or other body fluid). Details of this method are also given in co-owned U.S. patent applications, Ser. No. 09/736,920, entitled "Non-Invasive Method for Detecting Target RNA" (Non-Invasive Method), the disclosure of which is incorporated herein by reference.

Briefly, a test oligomer containing a backbone to be evaluated, having a base sequence targeted against a known RNA, is injected into a mammalian subject. The antisense oligomer may be directed against any intracellular RNA, including a host RNA or the RNA of an infecting virus. Several hours (typically 8-72) after administration, the urine is assayed for the presence of the antisense-RNA heteroduplex. If heteroduplex is detected, the backbone is suitable for use in the antisense oligomers of the present invention.

The test oligomer may be labeled, e.g. by a fluorescent or a radioactive tag, to facilitate subsequent analyses, if it is appropriate for the mammalian subject. The assay can be in any suitable solid-phase or fluid format. Generally, a solid-phase assay involves first binding the heteroduplex analyte to a solid-phase support, e.g., particles or a polymer or test-strip substrate, and detecting the presence/amount of heteroduplex bound. In a fluid-phase assay, the analyte sample is typically pretreated to remove interfering sample components. If the oligomer is labeled, the presence of the heteroduplex is confirmed by detecting the label tags. For non-labeled compounds, the heteroduplex may be detected by immunoassay if in solid phase format or by mass spectroscopy or other known methods if in solution or suspension format.

When the antisense oligomer is complementary to a virus-specific region of the viral genome (such as those regions of filovirus viral RNA or mRNA, as described above) the method can be used to detect the presence of a given filovirus, or reduction in the amount of virus during a treatment method.

E. Exemplary Oligomer Backbones

Examples of nonionic linkages that may be used in oligonucleotide analogs are shown in FIGS. 2A-2G. In these figures, B represents a purine or pyrimidine base-pairing moiety effective to bind, by base-specific hydrogen bonding, to a base in a polynucleotide, preferably selected from adenine, cytosine, guanine and uracil. Suitable backbone structures include carbonate (2A, R=O) and carbamate (2A, R=NH$_2$) linkages (Mertes and Coats 1969; Gait, Jones et al. 1974); alkyl phosphonate and phosphotriester linkages (2B, R=alkyl or —O-alkyl) (Lesnikowski, Jaworska et al. 1990); amide linkages (2C) (Blommers, Pieles et al. 1994); sulfone and sulfonamide linkages (2D, R$_1$, R$_2$=CH$_2$); and a thioformacetyl linkage (2E) (Cross, Rice et al. 1997). The latter is reported to have enhanced duplex and triplex stability with respect to phosphorothioate antisense compounds (Cross, Rice et al. 1997). Also reported are the 3'-methylene-N-methylhydroxyamino compounds of structure 2F.

Peptide nucleic acids (PNAs) are analogs of DNA in which the backbone is structurally homomorphous with a deoxyribose backbone, consisting of N-(2-aminoethyl)glycine units to which pyrimidine or purine bases are attached. PNAs containing natural pyrimidine and purine bases hybridize to complementary oligonucleotides obeying Watson-Crick base-pairing rules, and mimic DNA in terms of base pair recognition (Egholm, Buchardt et al. 1993). The backbone of PNAs are formed by peptide bonds rather than phosphodiester bonds, making them well-suited for antisense applications. The backbone is uncharged, resulting in PNA/DNA or PNA/RNA duplexes which exhibit greater than normal thermal stability. PNAs are not recognized by nucleases or proteases.

A preferred oligomer structure employs morpholino-based subunits bearing base-pairing moieties, joined by uncharged linkages, as described above. Especially preferred is a substantially uncharged phosphorodiamidate-linked morpholino oligomer, such as illustrated in FIGS. 1A-1D. Morpholino oligonucleotides, including antisense oligomers, are detailed, for example, in co-owned U.S. Pat. Nos. 5,698,685, 5,217,866, 5,142,047, 5,034,506, 5,166,315, 5,185,444, 5,521,063, and 5,506,337, all of which are expressly incorporated by reference herein.

Important properties of the morpholino-based subunits include: the ability to be linked in a oligomeric form by stable, uncharged backbone linkages; the ability to support a nucleotide base (e.g. adenine, cytosine, guanine or uracil) such that the polymer formed can hybridize with a complementary-base target nucleic acid, including target RNA, with high T$_m$, even with oligomers as short as 10-14 bases; the ability of the oligomer to be actively transported into mammalian cells; and the ability of the oligomer:RNA heteroduplex to resist RNAse degradation.

Exemplary backbone structures for antisense oligonucleotides of the invention include the β-morpholino subunit types shown in FIGS. 1A-1D, each linked by an uncharged, phosphorus-containing subunit linkage. FIG. 1A shows a phosphorus-containing linkage which forms the five atom repeating-unit backbone, where the morpholino rings are linked by a 1-atom phosphoamide linkage. FIG. 1B shows a linkage which produces a 6-atom repeating-unit backbone. In this structure, the atom Y linking the 5' morpholino carbon to the phosphorus group may be sulfur, nitrogen, carbon or, preferably, oxygen. The X moiety pendant from the phosphorus may be fluorine, an alkyl or substituted alkyl, an alkoxy or substituted alkoxy, a thioalkoxy or substituted thioalkoxy, or unsubstituted, monosubstituted, or disubstituted nitrogen, including cyclic structures, such as morpholines or piperidines. Alkyl, alkoxy and thioalkoxy preferably include 1-6 carbon atoms. The Z moieties are sulfur or oxygen, and are preferably oxygen.

Figure 1C:
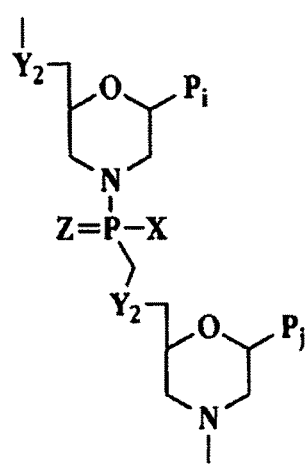
Figure 1D:
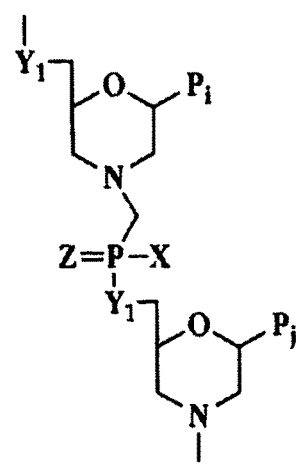

The linkages shown in FIGS. 1C and 1D are designed for 7-atom unit-length backbones. In Structure 1C, the X moiety is as in Structure 1B, and the moiety Y may be methylene, sulfur, or, preferably, oxygen. In Structure 1D, the X and Y moieties are as in Structure 1B. Particularly preferred morpholino oligonucleotides include those composed of morpholino subunit structures of the form shown in FIG. 1B, where X=NH$_2$ or N(CH$_3$)$_2$, Y=O, and Z=O.

As noted above, the substantially uncharged oligomer may advantageously include a limited number of charged linkages, e.g. up to about 1 per every 5 uncharged linkages, more preferably up to about 1 per every 10 uncharged linkages. Therefore a small number of charged linkages, e.g. charged phosphoramidate or phosphorothioate, may also be incorporated into the oligomers. A preferred cationic linkage is 1-piperazino phosphoramidate as shown in FIG. 2H.

The antisense compounds can be prepared by stepwise solid-phase synthesis, employing methods detailed in the references cited above. In some cases, it may be desirable to add additional chemical moieties to the antisense compound, e.g. to enhance pharmacokinetics or to facilitate capture or detection of the compound. Such a moiety may be covalently attached, typically to a terminus of the oligomer, according to standard synthetic methods. For example, addition of a polyethyleneglycol moiety or other hydrophilic polymer, e.g., one having 10-100 monomeric subunits, may be useful in enhancing solubility. One or more charged groups, e.g., anionic charged groups such as an organic acid, may enhance cell uptake. A reporter moiety, such as fluorescein or a radiolabeled group, may be attached for purposes of detection. Alternatively, the reporter label attached to the oligomer may be a ligand, such as an antigen or biotin, capable of binding a labeled antibody or streptavidin. In selecting a moiety for attachment or modification of an antisense oligomer, it is generally of course desirable to select chemical compounds of groups that are biocompatible and likely to be tolerated by a subject without undesirable side effects.

IV. Inhibition of Filovirus Replication

Figure 5:
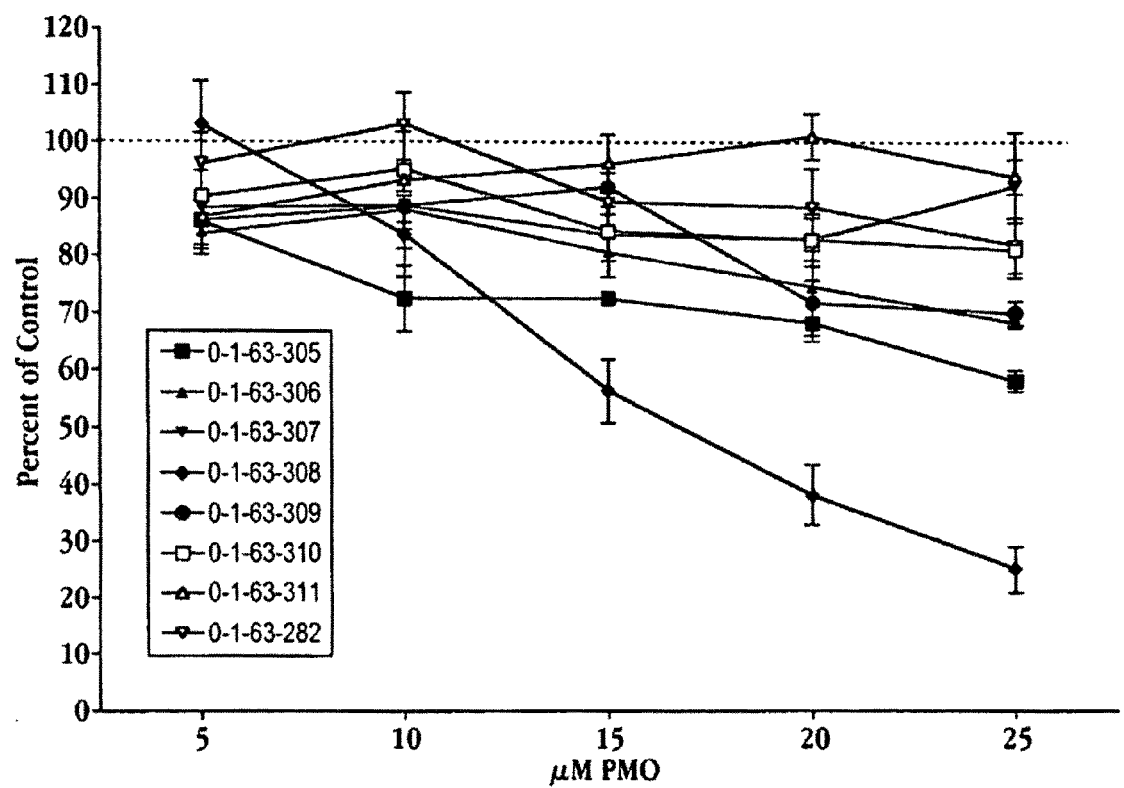
FIG. 5 is a plot showing cytotoxicity in Vero cell culture, expressed as a percent control, as a function of antisense type and concentration.

A. Inhibition in Vero Cells:

PMO antisense compounds and the control PMO (SEQ ID NO:35) were initially evaluated for cytotoxicity when incubated with Vero cells (FIG. 5) in the absence of virus. Only one PMO (0-1-63-308) was found to show dose dependent cytotoxicity in the concentration range of 5 to 25 μM.

Viral titer data were obtained 10 days post-infection of Vero cells. All inhibitors evaluated to date reduce the viral titer, as measured by TCID$_{50}$, to some degree (Table 6 below) but the VP35-AUG inhibitor (SEQ ID NO:21) was the most inhibitory against Ebola virus. The inoculum was taken from cells which received the treatment after infection (15 μM). No serum was added to media during pre-incubation with inhibitor or during infection. After the infection the inoculum was removed and replaced the medium containing 2% serum. The VP35-AUG PMO produced a 3 log reduction in viral titer relative to the no treatment control group. The L-AUG PMO (SEQ ID NO:16) did not produce reduction in viral titer. The L gene is active later in the viral life cycle and the RNA becomes highly bound by NP, VP30 and VP45 proteins so this target may be inaccessible to the L-AUG PMO used in this experiment.

TABLE 6

Viral Titer Reduction in Vero cells

| Treatment (PMO) | $TCID_{50}$ | $TCID_{50}/ml$ |
|---|---|---|
| Control (no treatment) | −5.5 | $3.16 \times 10^6$ |
| VP35-scr (SEQ ID NO: 60) | −3.2 | $1.47 \times 10^4$ |
| Dscr (SEQ ID NO: 59) | −3.8 | $6.81 \times 10^4$ |
| L-AUG (SEQ ID NO: 16) | −4.2 | $1.47 \times 10^5$ |
| VP35-AUG (SEQ ID NO: 21) | −2.5 | $3.16 \times 10^3$ |

Figure 6A:
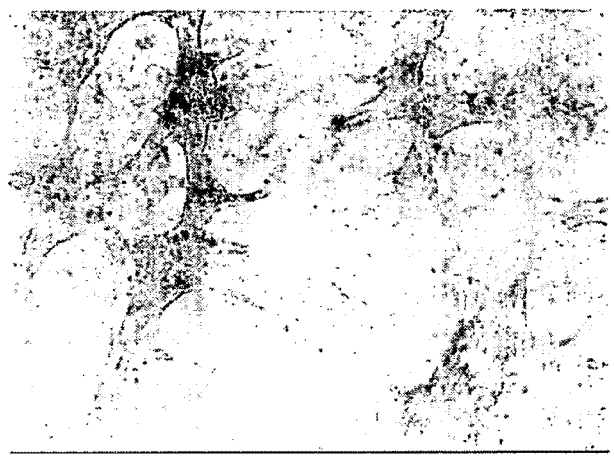
FIGS. 6A-6C are photomicrographs of Vero cells in culture (6A) in the absence of Ebola virus infection and antisense treatment; (6B) with Ebola virus infection but no antisense treatment; and (6C) with Ebola virus infection and treatment with VP35-AUG (SEQ ID NO:17) antisense compound.
Figure 6B:
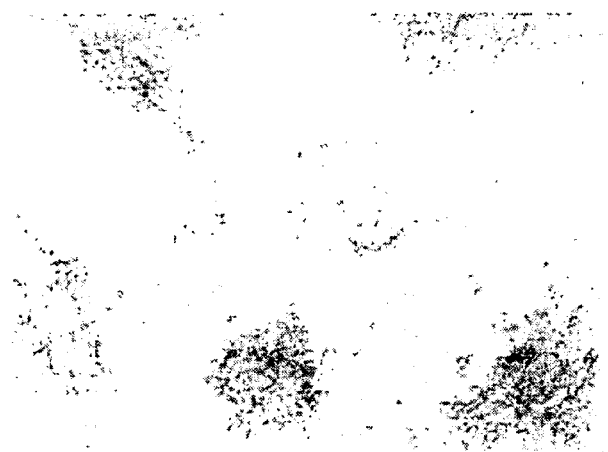
Figure 6C:
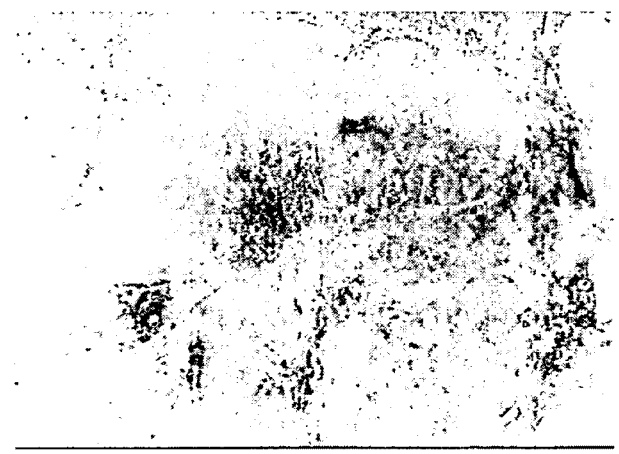

Vero cells were pretreated with different concentrations of the PMO (namely 0.1, 0.5, 1.0, 2.5, 5.0 and 10 μM), infected with EBOV for 1 h and the same concentration of PMO was added back afterwards. The 1 μM concentration of VP35-AUG (SEQ ID NO:21) inhibitor reduced the cytopathic effect (CPE) significantly compared to 0.5 μM concentration. The reduction in CPE has been repeatedly observed in culture and an example of these studies is seen in FIGS. 6A-6C for non-infected (FIG. 6A), infected, no treatment (FIG. 6B), and infected and treated (FIG. 6C).

B. Treatment in Infected Mice

These observations involved C57BL mice treated intraperitoneally (IP) with PMO at −24 and −4 hours prior to viral challenge at time 0. Each treatment group is composed of 10 male mice. The Ebola Zaire infection involves 100 pfu injected IP and death is the endpoint observed between days 7 and 10 post infection. A summary of studies to date is provided in Table 7. The dose×2 indicates the dose given at the two times prior to viral infection. The VP35-AUGcon compound refers to the VP35-AUG PMO that has been conjugated with the arginine-rich peptide $R_9F_2C$ (SEQ ID NO:61).

TABLE 7

Summary of Treatment in Mice

| Group | Dose | Survivors/challenged |
|---|---|---|
| Saline | na | 1/10 |
| Str. Ihn 1 (SEQ ID NO: 15) | 0.5 mg × 2 | 0/10 |
| VP35-AUG (SEQ ID NO: 21) | 0.5 mg × 2 | 6/10 |
| Saline | na | 0/10 |
| Str. Ihn 1 (SEQ ID NO: 15) | 1.0 mg × 2 | 2/10 |
| VP35-AUG (SEQ ID NO: 21) | 1.0 mg × 2 | 7/10 |
| Scramble (SEQ ID NO: 60) | 1.0 mg × 2 | 1/10 |
| VP35-AUG + Str Inh 1 (SEQ ID NOs: 21 and 15) | 1.0 mg × 2 | 6/10 |
| VP35-AUG-P003 + VP35-AUG (SEQ ID NO: 21 + 61 and 21) | 0.5 mg + 1.0 mg | 9/10 |
| VP35-AUG-P003 (SEQ ID NO: 21 + 61) | 0.5 mg × 2 | 9/10 |

Mice that survived the viral challenge described in TABLE 7 were rechallenged with virus to determine the immunological consequence of treatment. The results of the first studies are summarized in TABLE 8.

TABLE 8

Rechallenge Studies in Mice

| Group | Earlier Dose | Survivors/challenged |
|---|---|---|
| Saline | na | 0/10 |
| Str. Ihn 1, 0-1-63-412 | 0.5 mg × 2 | 1/2 |
| VP35, 0-1-63-413 | 0.5 mg × 2 | 6/6 |
| VP35, 0-1-63-413 | 1.0 mg × 2 | 7/7 |

All survivors from earlier Ebola challenge studies were evaluated in re-challenge studies 2 to 4 weeks after the initial viral exposure. The MOI for the re-challenge was identical to the initial challenge. All of the re-challenged survivors from therapeutic treatment with the PMO targeting VP35-AUG survived the re-challenge. These observations suggest viral replication was initiated in the viral challenge leading to a robust immune response, essentially a perfect vaccination. In accordance with another aspect, the invention includes a method of vaccinating a mammalian subject against Ebola virus by (i) pretreating the subject with antisense to Ebola virus, e.g., administering a VP35 antisense or compound combination at one or two times prior to Ebola virus challenge, and (ii) challenging the individual with the virus, preferably in an attenuated form incapable of producing serious infection.

Figures 7, 8:
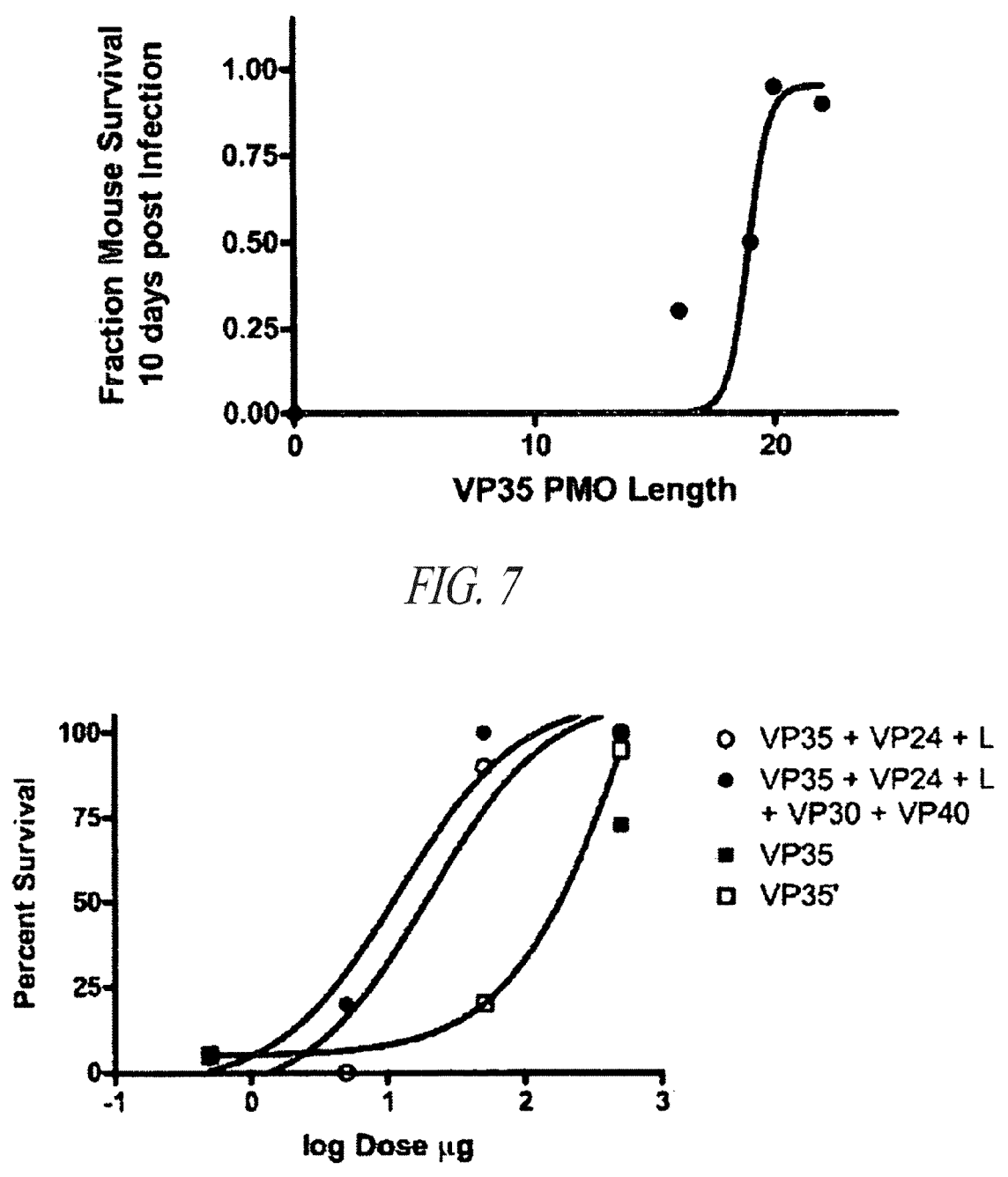

Similar treatment methods were aimed at determining the optimal length for anti-Ebola PMO antisense, employing various length VP35 antisense PMO. As seen from the data below (Table 9) and the plot in FIG. 7, the 16-mer is less effective than the 19-mer which is less effective than the 22-mer which is in the same order as the predicted Tm.

TABLE 9

Studies to Identify Optmal VP35-AUG Targeting Sequence

| Group | AVI Number | Survivors/challenged* |
|---|---|---|
| Saline | NA | 1/10 |
| VP35scr | SEQ ID NO: 60 | 1/10 |
| VP35-16 | SEQ ID NO: 25 | 3/10 |
| VP35-19 | SEQ ID NO: 24 | 5/10 |
| VP35-22 | SEQ ID NO: 23 | 9/10 |
| VP35'-AUG | SEQ ID NO: 22 | 10/10; 9/10 |

*Observations as of day 9 post challenge

Antisense compounds against six of the seven different genes expressed by Ebola were evaluated in the mouse model in a head-to-head experiment. (The GP gene was not included). As seen in Table 10, below, the most effective PMOs target VP24 and VP35 with L, VP40 and VP30 demonstrating less robust but significant activity in reducing mortality. The mice treated with VP40 died later than controls and those that survived appeared to be less active. These data indicate differences in the efficacy for the different gene targets. As single antisense compounds, the antisense against VP35 and VP24 are preferred therapeutic agents.

TABLE 10

Comparison of Ebola Gene Targets

| Target | SEQ ID NO | Survivors/challenged* |
|---|---|---|
| NP-AUG | 27 | 2/10 |
| VP40-AUG | 32 | 5/10 |
| VP30-AUG | 33 | 5/10 |
| VP24-AUG | 34 | 10/10; 5/10 |

TABLE 10-continued

Comparison of Ebola Gene Targets

| Target | SEQ ID NO | Survivors/challenged* |
|---|---|---|
| L'-AUG | 17 | 6/10; 2/10 |
| VP35-22 | 23 | 9/10 |
| Scramble | 60 | 0/10; 0/10 |
| PBS | NA | 1/10; 0/10 |

*Dose 0.5 mg IP at −24 and −4 hours to challenge, second survival numbers are from repeat experiment with fresh virus preparation.

In one embodiment, the antisense compound is administered in a composition (or separately) in combination with one or more other antisense compounds. One preferred combination is VP35-AUG (SEQ ID NO:21) plus VP24-AUG (SEQ ID NO:34); another is VP35-AUG, VP24-AUG and L-AUG (SEQ ID NOs:21, 34 and 16, respectively). As seen in Table 11 below, and as plotted in FIG. 8, the dose response curves for a combination of the 3 compounds (VP35-AUG, VP24-AUG and L-AUG, each given IP at 0.5 mg/dose) is not different from 5 different compounds (VP35-AUG, VP24-AUG, L-AUG, VP24-AUG and VP40-AUG). The dose of 0.5 mg/mouse provides 100 percent survival from either combination. Further, these data indicate the $EC_{50}$ for combination therapy is between 10 and 30 μg/mouse and that the $EC_{90}$ is approximately 50 μg/mouse.

TABLE 11

Combination Treatment for Ebola

| Group | SEQ ID NOs | Survivors/ Challenged |
|---|---|---|
| PBS | NA | 0/10 |
| NP-AUG, VP40-AUG, VP30-AUG, VP24-AUG, and L'-AUG | 27, 32-34 and 17 | 9/10 |
| NP-AUG, VP40-AUG, VP30-AUG, VP24-AUG, L'-AUG and VP35-AUG | 27, 32-34, 17 and 21 | 10/10 |
| VP35-AUG, VP24-AUG and L'-AUG | 21, 34 and 17 | 10/10 |
| VP35-AUG, VP24-AUG, L'-AUG, VP40-AUG and VP30-AUG | 21, 34, 17, 32 and 33 | 10/10 |

*Each agent in the combination administered 0.5 mg via IP route.

Figures 9A, 9B:
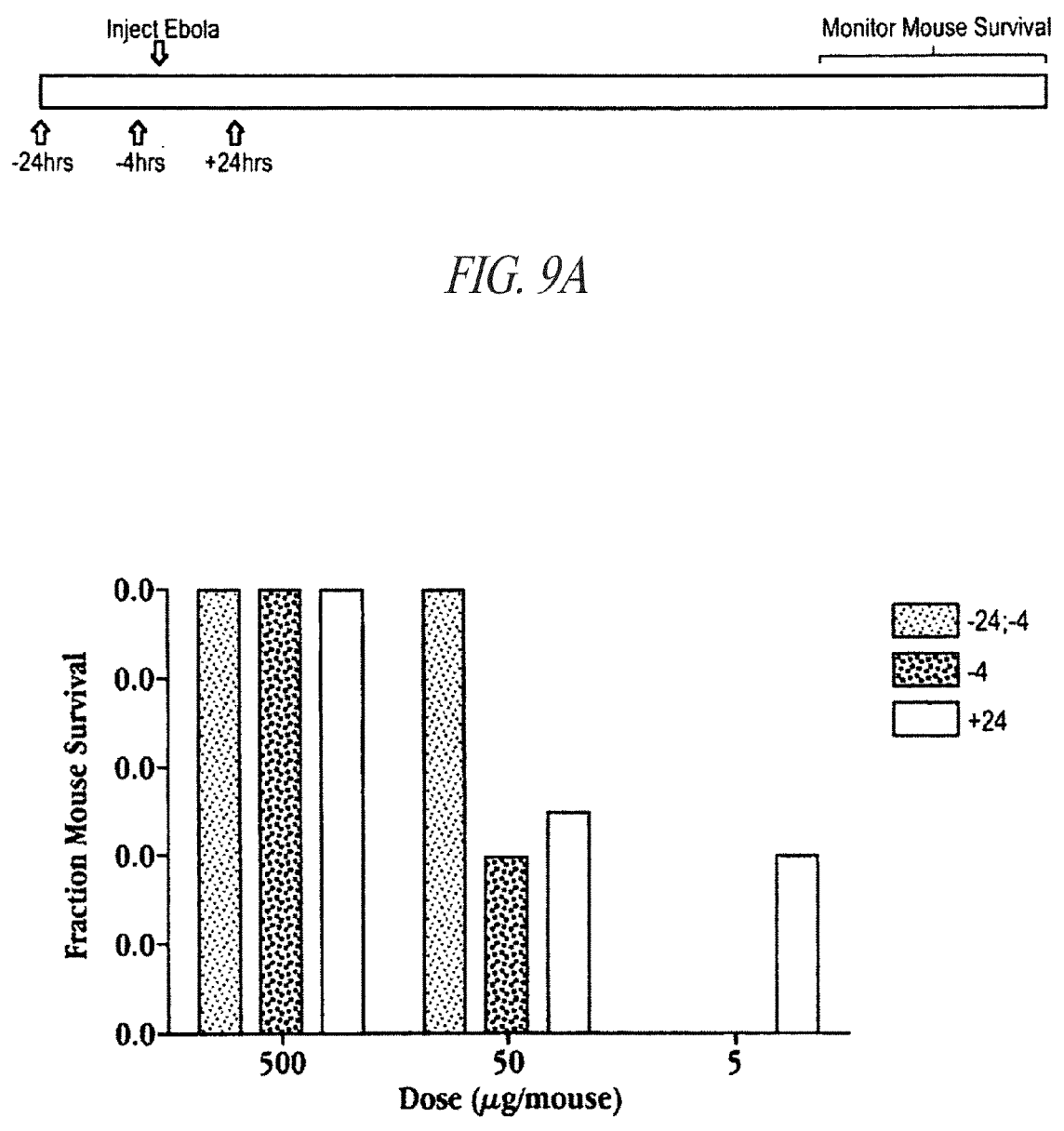

The success with 100 percent survival from a single IP injection 24 hours after Ebola infection (via IP route) indicates the antisense mechanism can suppress virus after viral replication has distributed throughout the body and that these agents can be used as therapy for infected individuals (Table 12 and FIG. 9). The comparison of dose-response in the −24 and −4 hour regimen between VP35-AUG only and the 3 agent combination is clear evidence of synergy. The combination could be more effective at 0.1× the dose than a single agent.

TABLE 12

Comparison of Dose Regimens

| Treatment | Dose (mg) | −24 and −4 hours | −4 hours only | +24 hours |
|---|---|---|---|---|
| VP35-AUG (SEQ ID NO: 21) | 0.5 | 9/10 | | |
| | 0.05 | 4/10 | | |
| VP35-AUG, VP24-AUG and L'-AUG (SEQ ID NOs: 21, 34 & 17) | 0.5 | 10/10 | 10/10 | 10/10 |
| | 0.05 | 10/10 | 4/10 | 5/10 |
| | 0.005 | | 0/10 | 4/10 |

V. Treatment Method

The antisense compounds detailed above are useful in inhibiting Ebola viral infection in a mammalian subject, including human subjects. Accordingly, the method of the invention comprises, in one embodiment, contacting a cell infected with the virus with an antisense agent effective to inhibit the replication of the virus. In one embodiment, the antisense agent is administered to a mammalian subject, e.g., human or domestic animal, infected with a given virus, in a suitable pharmaceutical carrier. It is contemplated that the antisense oligonucleotide arrests the growth of the RNA virus in the host. The RNA virus may be decreased in number or eliminated with little or no detrimental effect on the normal growth or development of the host.

A. Identification of the Infective Agent

The specific Ebola strain causing the infection can be determined by methods known in the art, e.g. serological or cultural methods, or by methods employing the antisense oligomers of the present invention.

Serological identification employs a viral sample or culture isolated from a biological specimen, e.g., stool, urine, cerebrospinal fluid, blood, etc., of the subject. Immunoassay for the detection of virus is generally carried out by methods routinely employed by those of skill in the art, e.g., ELISA or Western blot. In addition, monoclonal antibodies specific to particular viral strains or species are often commercially available.

Another method for identifying the Ebola viral strain employs one or more antisense oligomers targeting specific viral strains. In this method, (a) the oligomer(s) are administered to the subject; (b) at a selected time after said administering, a body fluid sample is obtained from the subject; and (c) the sample is assayed for the presence of a nuclease-resistant heteroduplex comprising the antisense oligomer and a complementary portion of the viral genome. Steps (a)-(c) are carried for at least one such oligomer, or as many as is necessary to identify the virus or family of viruses. Oligomers can be administered and assayed sequentially or, more conveniently, concurrently. The viral strain is identified based on the presence (or absence) of a heteroduplex comprising the antisense oligomer and a complementary portion of the viral genome of the given known virus or family of viruses.

Preferably, a first group of oligomers, targeting broad families, is utilized first, followed by selected oligomers complementary to specific genera and/or species and/or strains within the broad family/genus thereby identified. This second group of oligomers includes targeting sequences directed to specific genera and/or species and/or strains within a broad family/genus. Several different second oligomer collections, i.e. one for each broad virus family/genus tested in the first stage, are generally provided. Sequences are selected which are (i) specific for the individual genus/species/strains being tested and (ii) not found in humans.

B. Administration of the Antisense Oligomer

Effective delivery of the antisense oligomer to the target nucleic acid is an important aspect of treatment. In accordance with the invention, routes of antisense oligomer delivery include, but are not limited to, various systemic routes, including oral and parenteral routes, e.g., intravenous, subcutaneous, intraperitoneal, and intramuscular, as well as inhalation, transdermal and topical delivery. The appropriate route may be determined by one of skill in the art, as appropriate to the condition of the subject under treatment. For example, an appropriate route for delivery of a antisense oligomer in the treatment of a viral infection of the skin is topical delivery, while delivery of a antisense oligomer for the treatment of a viral respiratory infection is by inhalation. The oligomer may also be delivered directly to the site of viral infection, or to the bloodstream.

The antisense oligomer may be administered in any convenient vehicle which is physiologically acceptable. Such a composition may include any of a variety of standard pharmaceutically accepted carriers employed by those of ordinary skill in the art. Examples include, but are not limited to, saline, phosphate buffered saline (PBS), water, aqueous ethanol, emulsions, such as oil/water emulsions or triglyceride emulsions, tablets and capsules. The choice of suitable physiologically acceptable carrier will vary dependent upon the chosen mode of administration.

In some instances, liposomes may be employed to facilitate uptake of the antisense oligonucleotide into cells. (See, e.g., Williams, S. A., Leukemia 10(12): 1980-1989, 1996; Lappalainen et al., Antiviral Res. 23:119, 1994; Uhlmann et al., "Antisense oligonucleotides: A new therapeutic principle," Chemical Reviews, Volume 90, No. 4, pages 544-584, 1990; Gregoriadis, G., Chapter 14, Liposomes, Drug Carriers in Biology and Medicine, pp. 287-341, Academic Press, 1979). Hydrogels may also be used as vehicles for antisense oligomer administration, for example, as described in WO 93/01286. Alternatively, the oligonucleotides may be administered in microspheres or microparticles. (See, e.g., Wu, G.Y. and Wu, C. H., J. Biol. Chem. 262:4429-4432, 1987). Alternatively, the use of gas-filled microbubbles complexed with the antisense oligomers can enhance delivery to target tissues, as described in U.S. Pat. No. 6,245,747.

Sustained release compositions may also be used. These may include semipermeable polymeric matrices in the form of shaped articles such as films or microcapsules.

The antisense compound is generally administered in an amount and manner effective to result in a peak blood concentration of at least 200-400 nM antisense oligomer. Typically, one or more doses of antisense oligomer are administered, generally at regular intervals, for a period of about one to two weeks. Preferred doses for oral administration are from about 5-1000 mg oligomer or oligomer cocktail per 70 kg individual. In some cases, doses of greater than 500 mg oligomer/patient may be necessary. For i.v., i.p or s.q. administration, preferred doses are from about 100-1000 mg oligomer or oligomer cocktail per 70 kg body weight. The antisense oligomer may be administered at regular intervals for a short time period, e.g., daily for two weeks or less. However, in some cases the oligomer is administered intermittently over a longer period of time. Administration may be followed by, or concurrent with, administration of an antibiotic or other therapeutic treatment. The treatment regimen may be adjusted (dose, frequency, route, etc.) as indicated, based on the results of immunoassays, other biochemical tests and physiological examination of the subject under treatment.

EXAMPLES

Materials and Methods:

Synthesis of PMOs. PMOs were designed with sequence homology near or overlapping the AUG start site of Ebola virus VP35 (VP35'-AUG, SEQ ID NO:22), VP24 (VP24-AUG, SEQ ID NO:36), and L (L'-AUG, SEQ ID NO:17). Unrelated, scrambled PMOs (SEQ ID NOs:59 and 60) were used as a control in all experiments. The PMOs were synthesized by AVI Biopharma, Inc. (Corvallis, Oreg.), as previously described (Summerton and Weller 1997).

In vitro translation assay. The protein coding sequence for firefly luciferase, without the initiator-Met codon ATG, was subcloned into the multiple cloning site of plasmid pCiNeo (Promega). Subsequently, complementary oligonucleotides for Ebola virus VP35 (−98 to +39 bases 3020 to 3157), Ebola virus VP24 (−84 to +43 or bases 10261 to 10390), Ebola virus L (−80 to +49 or bases 11501 to 11632) were duplexed and subcloned into Nhe 1 and Sal 1 sites. RNA was generated from the T7 promoter with T7 Mega script (Ambion, Inc., Austin, Tex.). The in vitro translations were carried out by mixing different concentrations of PMO with 6 nM RNA. A sigmoidal curve to determine the $EC_{50}$ values was generated with the observed luciferase light emission (n=3 per PMO concentration) and the PMO concentration.

Figure 10:
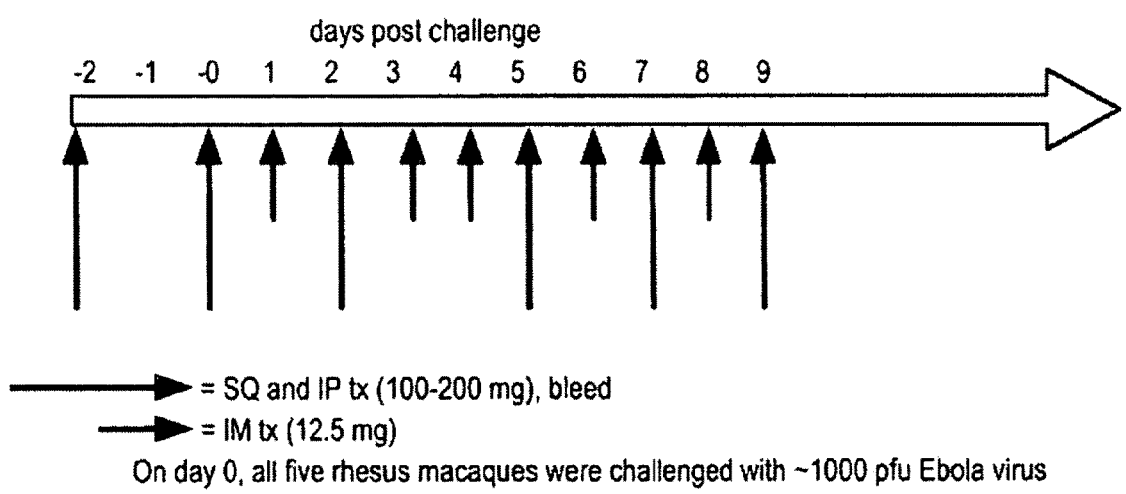
FIG. 10 is a schematic of the treatment schedule for a trial using PMO to treat Ebola infection in nonhuman primates.

Ebola virus infection of PMO-treated animals. C57Bl/6 mice, aged 8-10 weeks of both sexes, were obtained from National Cancer Institute, Frederick Cancer Research and Development Center (Frederick, Md.). Mice were housed in microisolator cages and provided autoclaved water and chow ad libitum. Mice were challenged by intraperitoneal injection with ~1000 pfu of mouse-adapted Ebola virus diluted in phosphate buffered saline (PBS) (Bray, Davis et al. 1998). Mice were treated with a combination of 1 mg, 0.1, or 0.01 mg of each of the VP24-AUG, L'-AUG and VP35'-AUG PMOs (SEQ ID NOs:34, 17 and 22, respectively) or the scramble control PMO (SEQ ID NO:60) either split between two equivalent doses at 24 and 4 hours prior to Ebola virus challenge or a single dose 24 hours after challenge. C57B1/6 mice were challenged intraperitoneally with 1000 plaque-forming units of mouse-adapted Ebola virus (Bray, Davis et al. 1998). Hartley guinea pigs were treated intraperitoneally with 10 mg of each of the VP24-AUG, VP35'-AUG, and L'-AUG PMOs 24 hours before or 24 or 96 hours after subcutaneous challenge with 1000 pfu of guinea-pig adapted Ebola virus (Connolly, Steele et al. 1999). Female rhesus macaques of 3-4 kg in weight were challenged with ~1000 pfu of Ebola virus ('95 strain) (Jahrling, Geisbert et al. 1999) by intramuscular injection following PMO treatment. The monkeys were treated from days −2 through day 9 via a combination of parenteral routes as shown in FIG. 10. The dose of the VP24-AUG PMO was 12.5-25 mg at each injection and the dose of the VP35'-AUG and L'-AUG PMOs ranged from 12.5-100 mg per injection.

Example 1

Antiviral Efficacy of Ebola Virus-Specific PMOS in Rodents

Figure 11A:
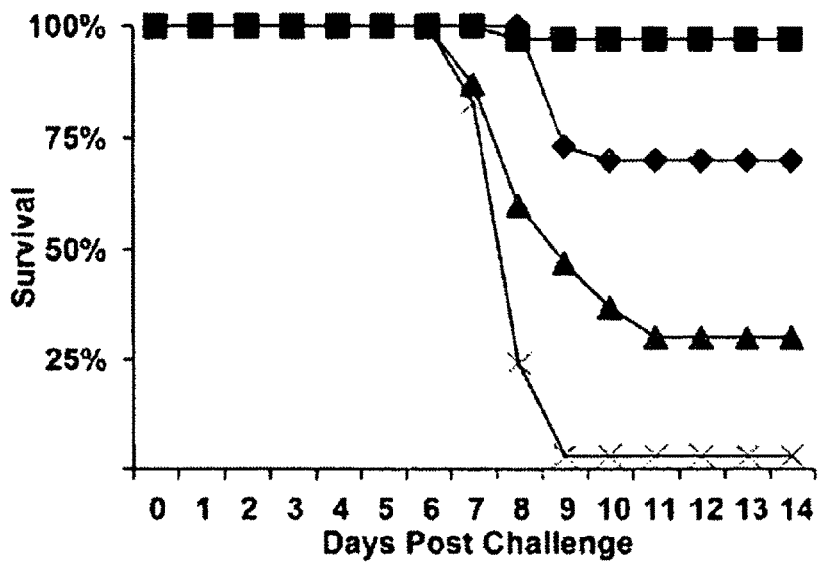
FIG. 11 shows Ebola-specific PMOs protect mice from lethal Ebola virus infection. (A) Survival of mice pretreated at 4 and 24 hours before EBOV infection with 500 µg of PMOs targeting VP24 (♦), VP35 (■), L (▲), or with an unrelated sequence (X). (B) Survival of mice pretreated with 1 mg (◇), 0.1 mg (□), or 0.01 mg (Δ) of a combination of the VP24, VP35, and L) PMOs or 1 mg (♦), 0.1 mg (■), or 0.01 mg (▲) of VP35 PMO only or an unrelated sequence (X). (C) Survival in mice treated 24 hours following EBOV infection with 1 mg (♦), 0.1 mg (■), or 0.01 mg (▲) of the combination of PMOs or an unrelated sequence (X). (D-G) C57B1/6 mice were challenged intraperitoneally with 1000 plaque-forming units of EBOV following treatment with PMOs. Immunoperoxidase stain is brown with hematoxylin counterstain. Viral antigen within the spleen (100×) of a mouse treated with scrambled PMO (D) or the EBOV PMOs (E) three days after EBOV infection. Diffuse staining pattern in the livers (600×) of the scrambled PMO-treated mice (F) on day 6 of EBOV infection, compared to focal areas of infection in the mice treated with the combination of PMOs (G).
Figure 11B:
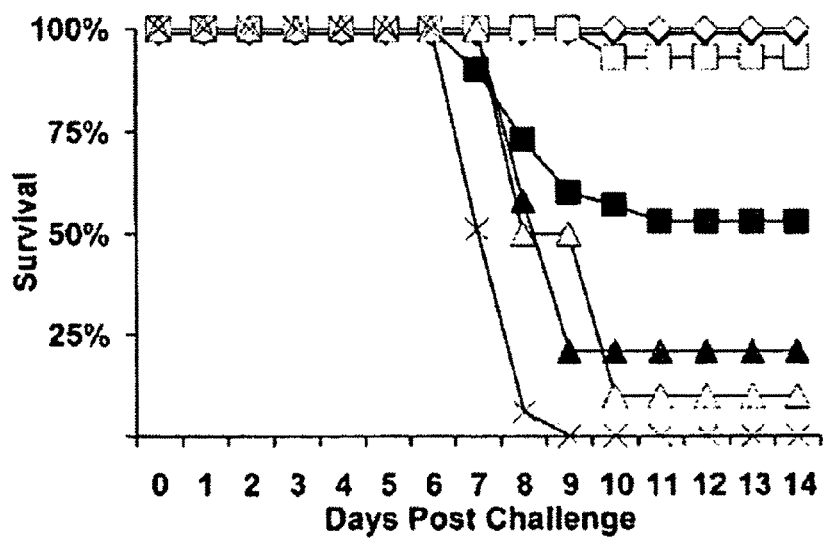
Figure 11C:
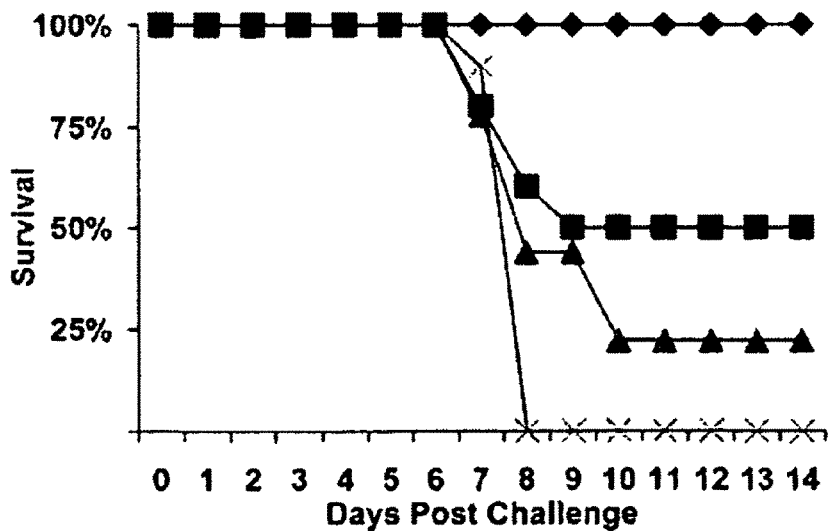
Figure 11D:
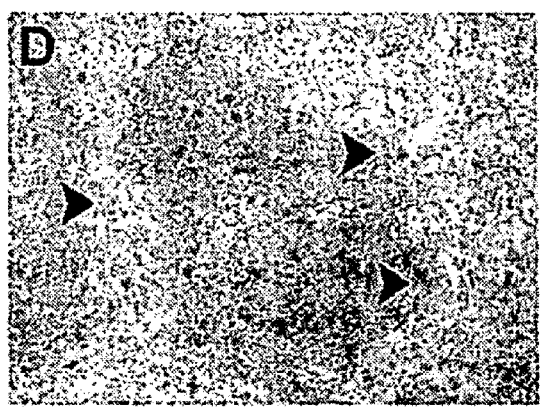
Figure 11E:
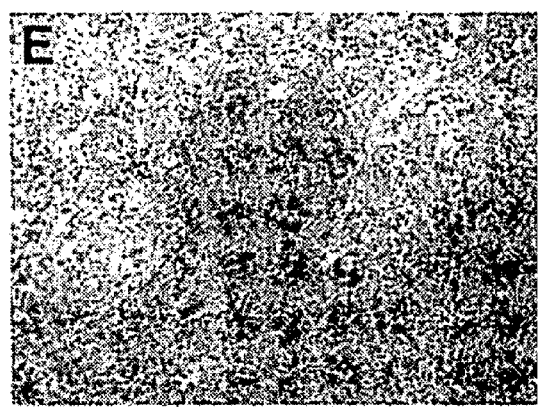
Figure 11F:
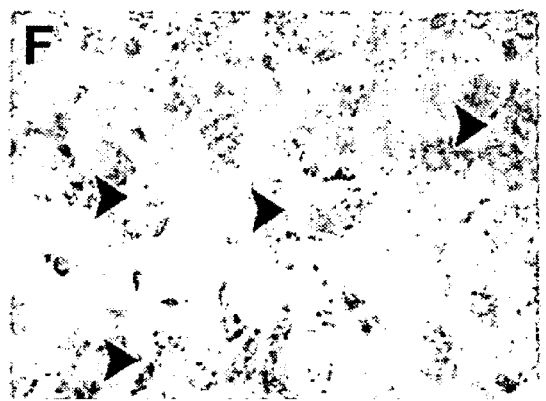
Figure 11G:
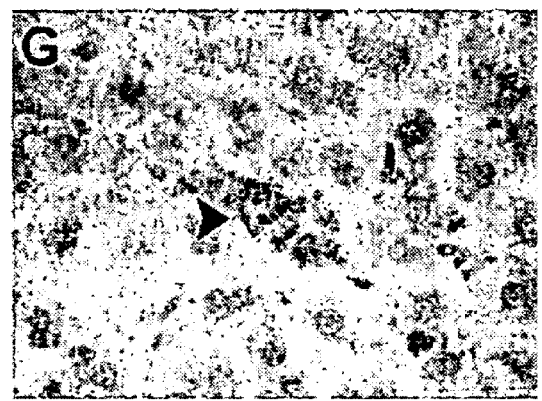
Figure 12:
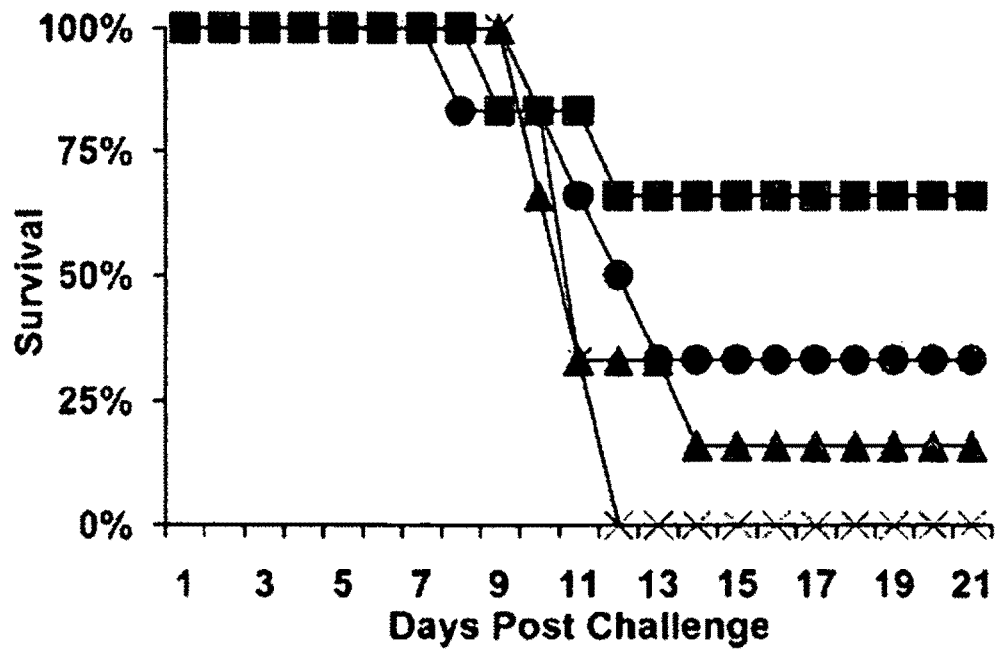
FIG. 12 shows that treatment of guinea pigs with antisense PMOs increases survival following lethal Ebola virus infection. Hartley guinea pigs were treated intraperitoneally with 10 mg each of VP24, VP35, and L PMO in PBS at −24 (▲), +24 (●), or +96 (■) hours post challenge. Control guinea pigs were injected with PBS only (X). The guinea pigs were infected subcutaneously with ~1000 pfu of EBOV and monitored for illness for 21 days. The data are presented as percent survival for each group (n=6).

To determine the in vivo efficacy of the Ebola virus-specific PMOs, the survival of mice treated with 500 μg doses of the individual PMOs (VP24-AUG, L'-AUG and VP35'-AUG, SEQ ID NOs:34, 17 and 22, respectively) at 24 and 4 hours before challenge with 1000 plaque-forming units (pfu) of mouse-adapted Ebola virus was determined. The VP35'-AUG, VP24-AUG and L'-AUG PMOs exhibited a wide range of efficacy against lethal EBOV infection and the VP35'-specific PMO provided nearly complete protection (FIG. 11A). Next, we performed a dose response experiment with the VP35 PMO and found that reducing the dose of the PMO from 1,000 to 100 μg reduced the efficacy substantially (FIG. 11B). Hence, to further enhance efficacy, we decided to use a combination of all three PMOs. This combination of PMOs administered 24 and 4 h before lethal Ebola virus challenge resulted in robust protection and showed substantial enhancement in protection afforded by the VP35 PMO alone, especially at lower doses (FIG. 11B). To determine the efficacy of the combination of PMOs in a post-challenge treatment regimen, mice were injected with 1,000 pfu of Ebola virus and were treated the next day with the PMOs (FIG. 11C). Mice that were given a single dose of 1,000 μg 24 h after the lethal challenge and survival was scored for 14 days. Again, Ebola virus-infected mice were fully protected and lower doses showed substantial protection as compared to the control PMO. To determine the effectiveness of the PMO treatment in Ebola virus-infected guinea pigs, the combination of PMOs was administered 24 hours before or 24 or 96 hours after EBOV infection. Survival was greatly increased in guinea pigs receiving the PMOs either 24 or 96 hours after infection, as compared to untreated or pretreated guinea pigs as shown in FIG. 12.

Figure 13:
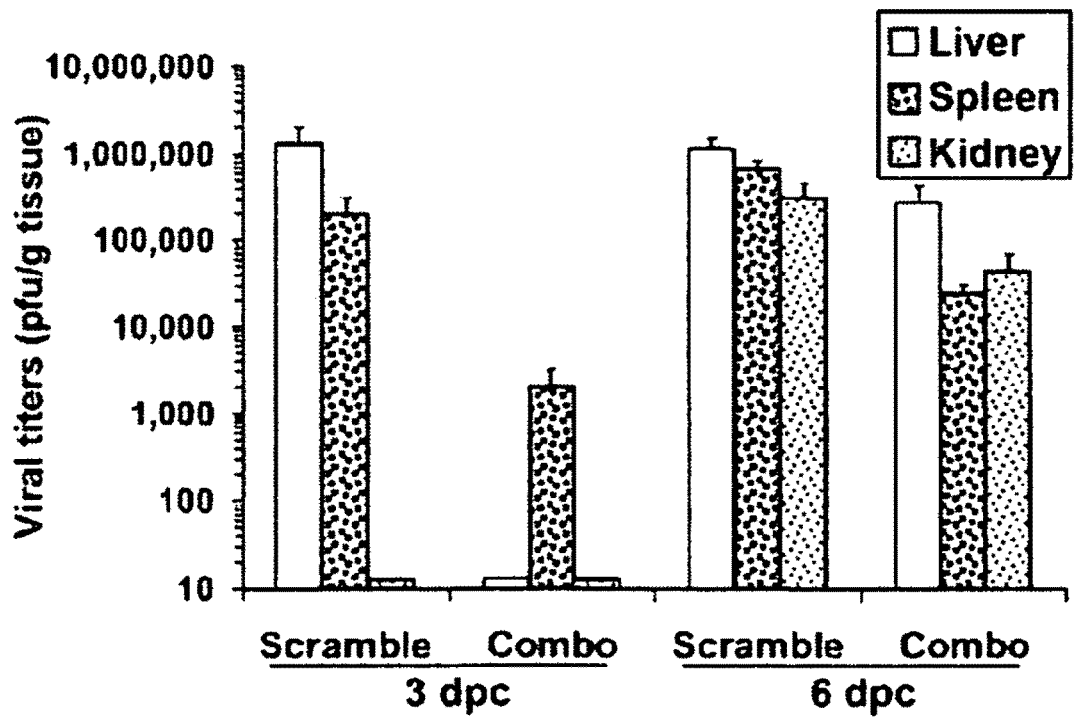
FIG. 13 shows that Ebola-specific PMOs reduce viral replication in vivo. Viral titers in tissues from mice treated with a combination of PMO and infected with 1000 pfu of EBOV. Samples of the liver, spleen, and kidney were taken at 3 or 6 days post challenge (dpc), macerated, and analyzed for viral titer using plaque assay. The data are presented as the mean viral titer of 3 mice with error bars representing the standard deviation.
Figure 14A:
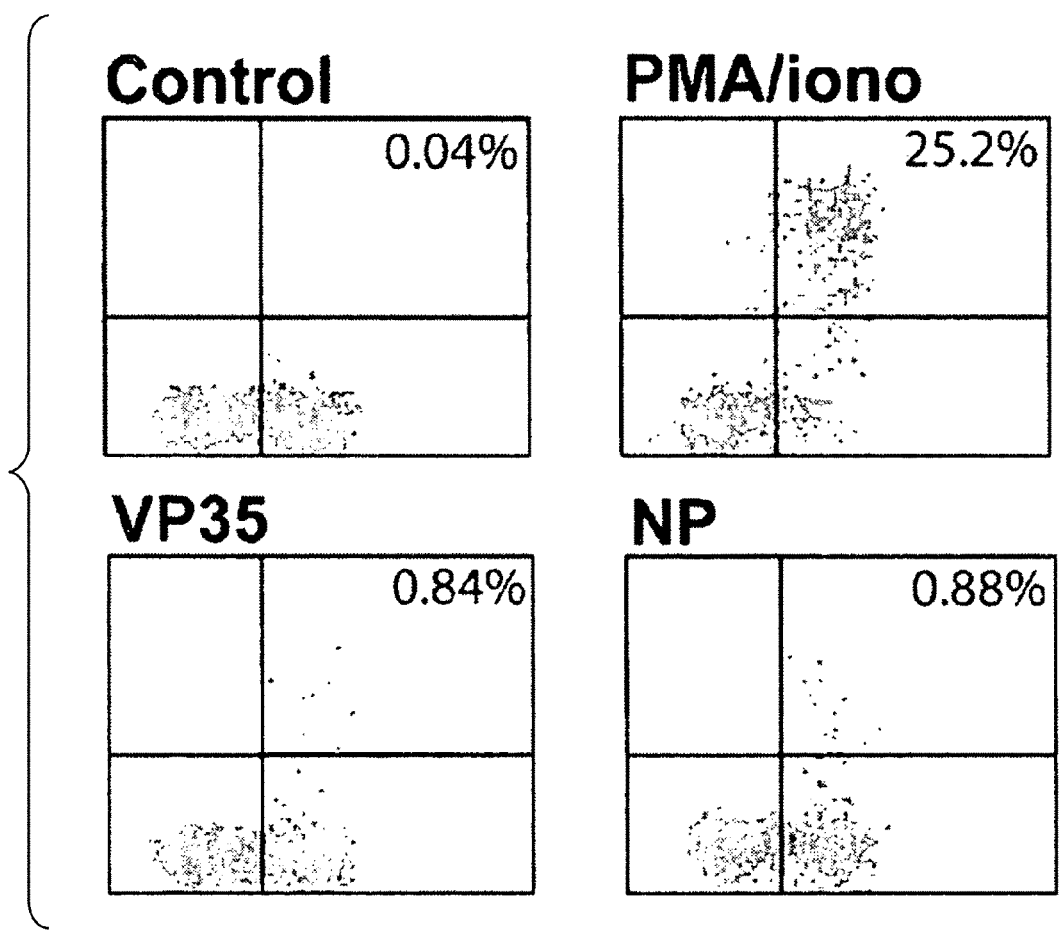
FIG. 14 shows the immune responses of PMO-treated mice following survival of Ebola virus infection. (A) PMO-treated C57BL/6 mice that have previously survived EBOV infection generate EBOV-specific CD8+ responses. Pooled splenocytes from three PMO-treated EBOV survivors were re-stimulated in vitro with EBOV-specific VP35 or NP peptides, an irrelevant Lassa NP peptide as a negative control, or PMA/ionomycin as a positive control. The stimulated cells were stained after for 4 hours in culture with anti-CD44 FITC, anti-IFN-γ PE, and anti-CD8 Cy-Chrome. The percent of CD44+, IFN-γ+ cells among CD8+ lymphocytes is indicated in the upper right quadrant of each plot. These data are representative of the Ebola CD8 specific epitopes observed after challenge. (B) Total serum anti-Ebola virus antibodies were measured in surviving mice prior to or 4 weeks following treatment and challenge. PMO mice were treated with the combination of PMOs 24 and 4 hours before challenge and their antibody responses are compared with mice treated with Ebola VLPs 24 hours before EBOV infection. The results are depicted as the endpoint titers of the individual mice (circles). The horizontal line in each column represents the geometric mean titer of the group. (C) Mice that previously survived EBOV challenge following PMO treatment were re-challenged with 1000 pfu of mouse-adapted Ebola virus 4 weeks after the initial challenge. Results are plotted as percent survival for the PMO-treated mice (black) and naïve control mice (n=10 per group).
Figures 14B, 14C:
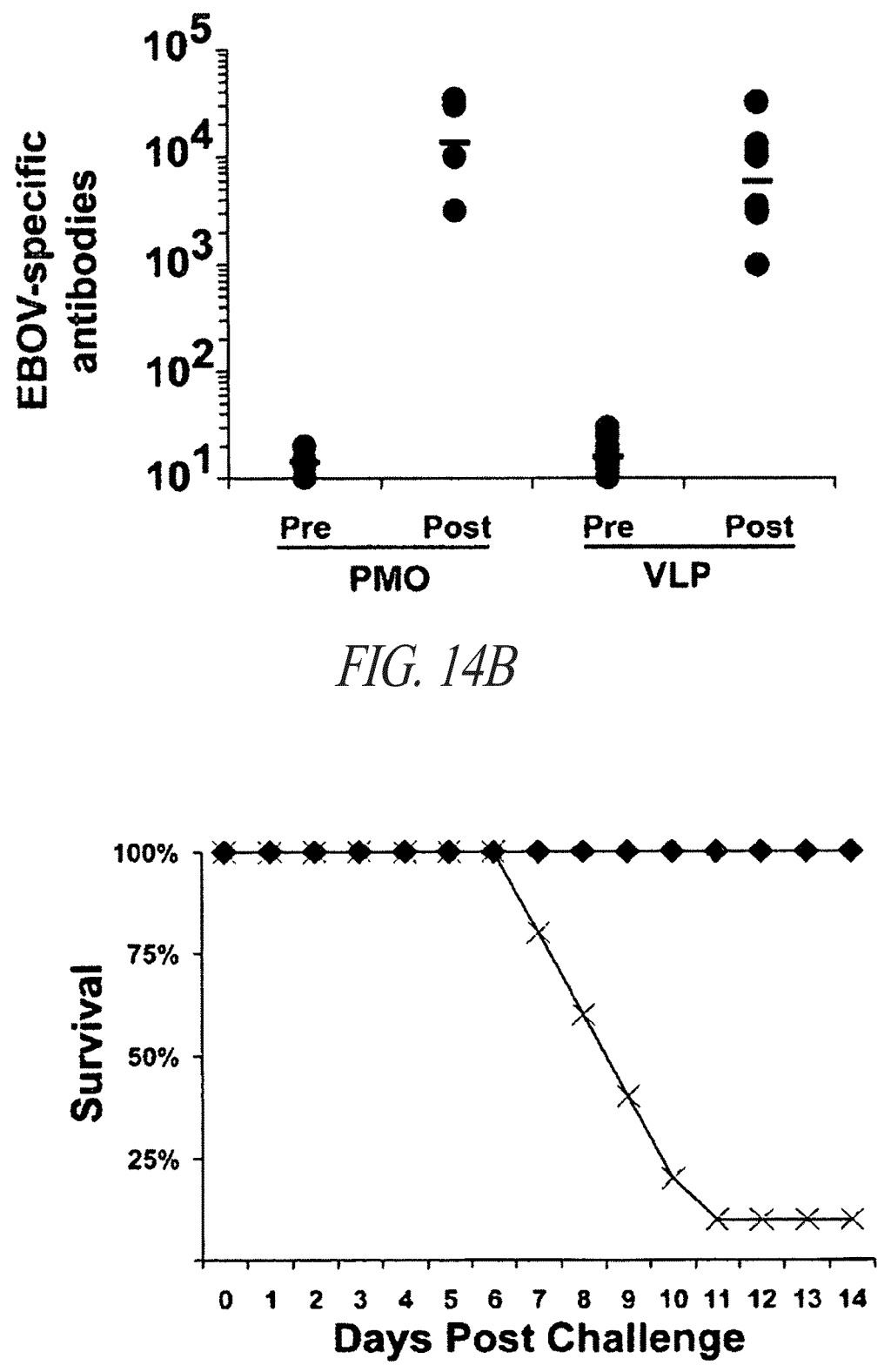

Examination of tissues shortly following infection showed that treatment of mice with the combination of Ebola virus-specific PMO slowed viral spread compared to mice treated with the scrambled PMO. Three days after the infection, multiple foci of infected cells were easily observed in the spleens of the mice treated with the scrambled PMO (FIG. 13D). In contrast, very few EBOV-infected cells could be found in the spleens of the anti-EBOV PMO-treated mice (FIG. 13E). Six days after viral inoculation, the infection was fulminant in the spleens of all animals (data not shown) and had spread to the livers of both mice treated with scrambled and combination PMOs (FIGS. 13F and 13G). However, the extent of the infection was limited in the combination PMO-treated mice, and, unlike the scrambled PMO-treated mice, EBOV antigen was not detectable within their hepatocytes, (FIGS. 13F and 13G). The observed pattern of antigen staining within the tissues was corroborated by the viral titers as shown in FIG. 14.

Figure 15A:
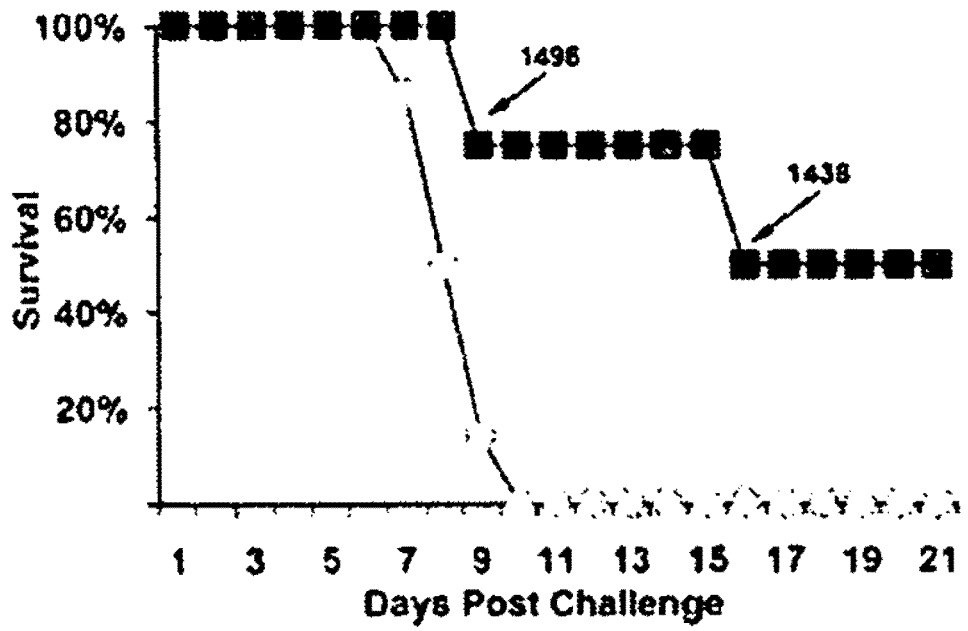
FIG. 15 shows that treatment of rhesus macaques with antisense PMOs provide protection against lethal Ebola virus infection. (A) Survival following infection with 1000 pfu of EBOV in monkeys treated with a combination of PMOs (■) or untreated monkeys (○). The arrows indicate the monkeys that died at the time indicated. (B-D) Viral titers (B), platelet counts (C), or alkaline phosphatase levels (D) in the blood of the PMO-treated monkeys [0646 (♦), 1438 (▲), 1496 (X), 1510 (■)] or an untreated monkey (○).
Figure 15B:
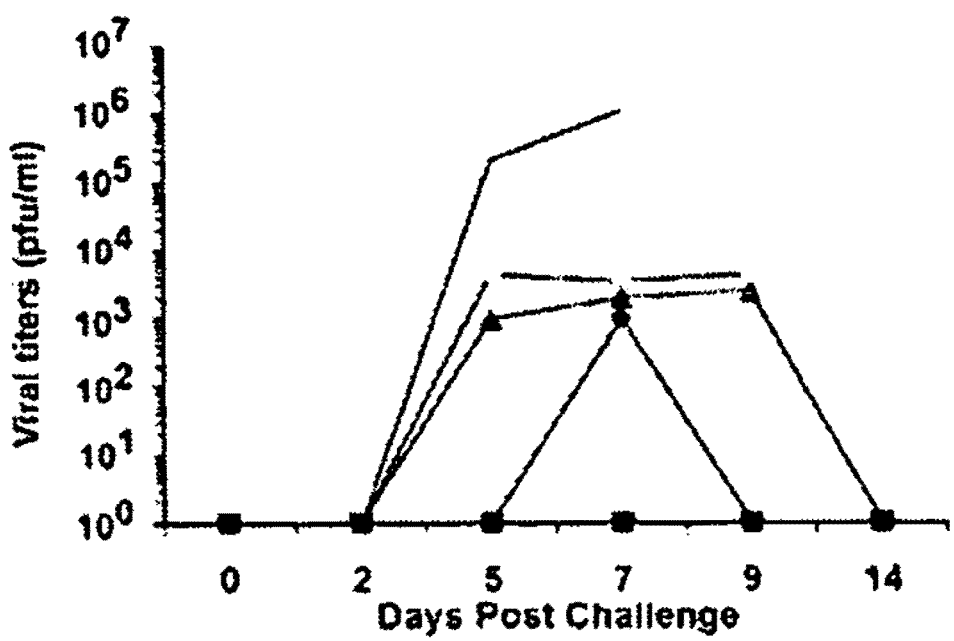
Figure 15C:
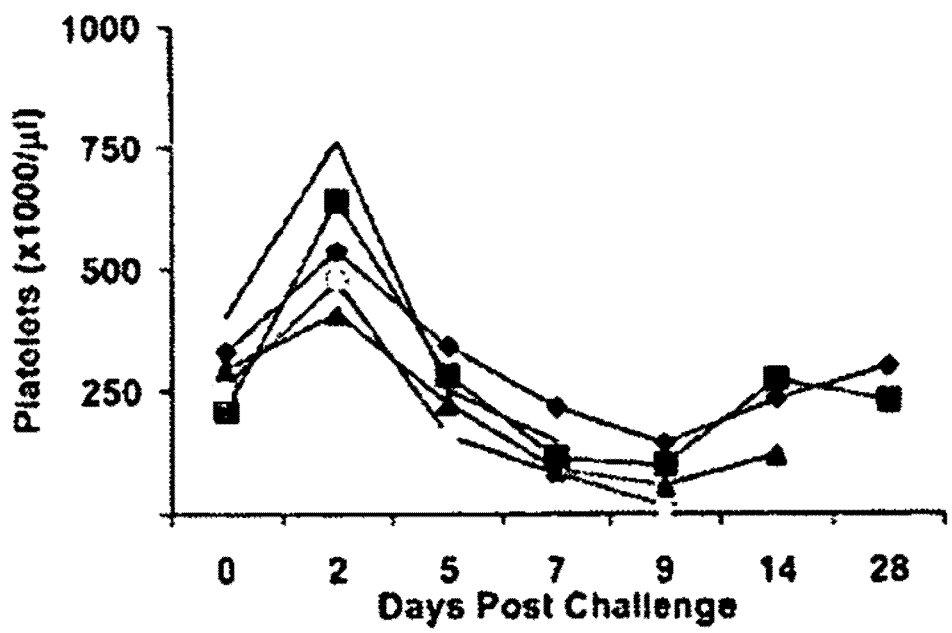
Figure 15D:
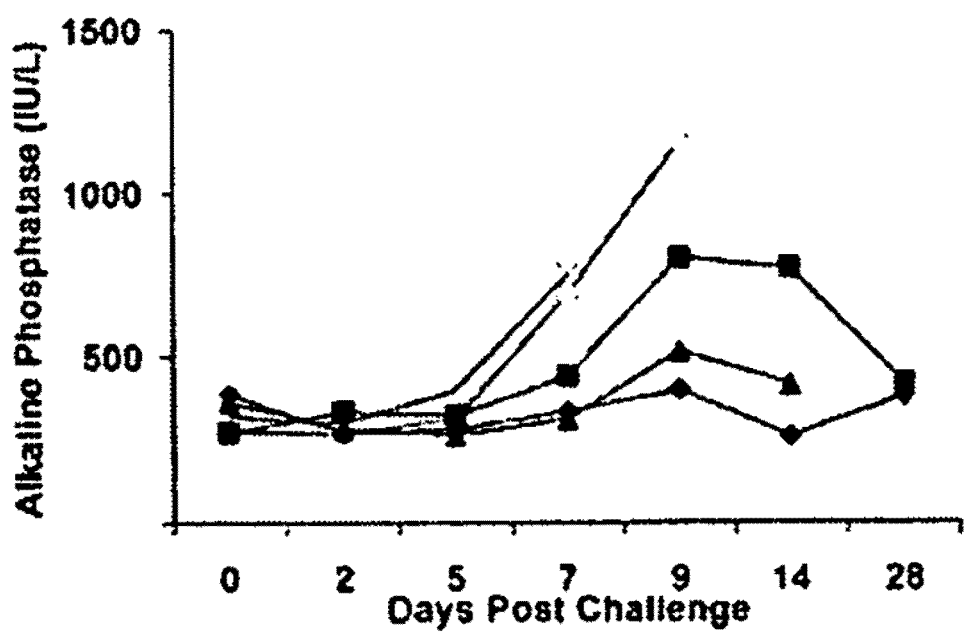

To determine whether mice treated with the PMO therapeutics generated immune responses to Ebola virus, they were tested for Ebola virus-specific cell-mediated and humoral immune responses. Four weeks after infection, the mice demonstrated both CD4+ and CD8+ T cell responses to multiple Ebola virus peptides, including NP and VP35 as shown in FIG. 15A. They also generated strong serum Ebola virus-specific antibody responses that were similar to the post-challenge antibody responses of mice protected by a therapeutic Ebola virus-like particle vaccine as shown in FIG. 15B (Warfield, Perkins et al. 2004). To study if the generated immune responses were protective, PMO-treated mice were rechallenged with another dose of 1,000 pfu of Ebola virus four weeks after surviving the initial challenge and these mice were completely protected from a second lethal Ebola virus infection as shown in FIG. 15C.

Example 2

Antiviral Efficacy of Ebola Virus-Specific PMOS in Non-Human Primates

Based on the encouraging results both in vitro and in rodents, a trial in nonhuman primates was performed. Four rhesus monkeys were treated with PMO from two days prior to Ebola virus infection through day 9 of the infection. The naïve control monkey in this experiment received no treatment and succumbed to Ebola virus infection on day 10 as shown in FIG. 16A. Of 12 rhesus monkeys that have been infected in the inventors' laboratory with the same seed stock of virus, all died of Ebola virus between days 7 and 10 as shown in FIG. 16A. One of the PMO-treated monkeys succumbed to the infection on day 10. A second PMO-treated monkey cleared the EBOV infection from its circulation between days 9 and 14, but was unable to recover from disease and died on day 16 as shown in FIGS. 16A and 16B. The two surviving monkeys had no symptoms of disease beyond mild depression until day 35, at which time they were euthanized. Incorporating historical controls, there were significant differences in survival curves between groups (p=0.0032). The mean survival time for the treatment group was 14.3 days with a standard error of 2.1 days. The mean survival time for the control group was 8.3 days with a standard error of 0.2 days. The overall survival rate demonstrated a significant p value of 0.0392, when compared to historical data.

There were early clinical signs or laboratory values that correlated with survival. The laboratory tests that most closely predicted survival were viral titers, platelet counts, and liver-associated enzymes in the blood. The monkeys that did not survive infection had detectable virus by day 5, in stark contrast to the PMO-treated monkeys that survived, which had little to no viremia on day 5 (FIG. 16B). As expected in a hemorrhagic disease, both the PMO-treated and naïve monkeys exhibited thrombocytopenia. However, the PMO-treated monkeys that survived did not have platelet counts far below 100,000 at any time, and their platelet counts began to recover coincident with viral clearance (FIG. 16C). Similarly, all the monkeys experienced increases in their liver-associated enzyme levels, including alkaline phosphatase. However, the levels in the surviving monkeys did not climb as high as those that succumbed to the infection, and they returned to normal levels within the month after the EBOV infection (FIG. 16D). No correlation was found between survival and multiple other hematological values, body temperature, serum cytokines, or fibrin degradation products. Since the surviving PMO-treated monkeys had low to undetectable viremias following infection, we assessed the immune responses of the surviving monkeys. By 28 days after Ebola virus challenge, the surviving rhesus monkeys had high levels of both anti-EBOV antibodies and T cell responses, similar to the PMO-protected mice.

Example 3

Increased Antisense of Activity Using PMO With Cationic Linkages

Figure 16:
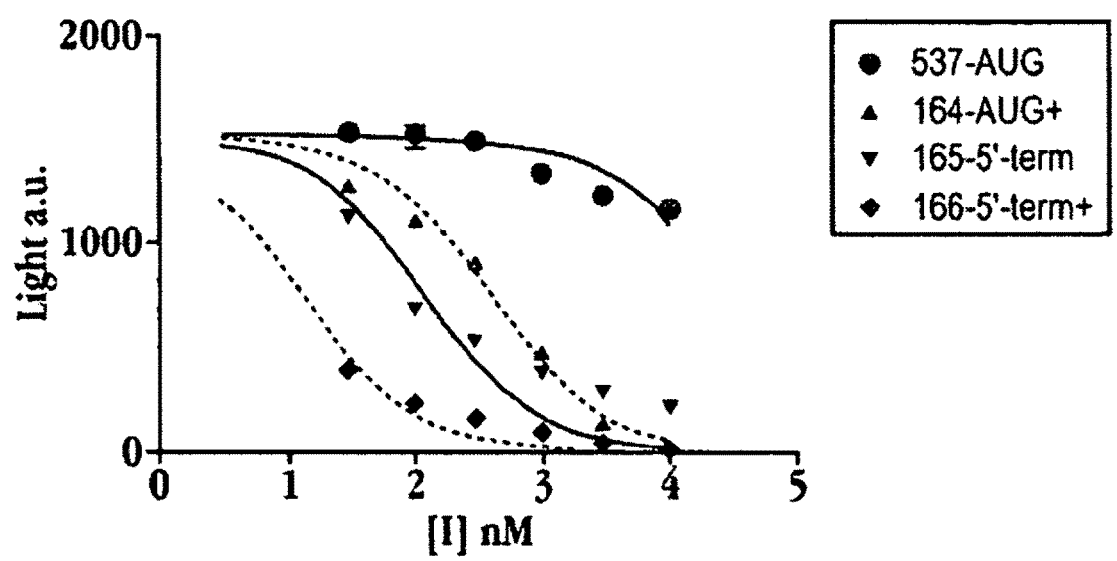
FIG. 16 shows the increased antisense activity of PMOs with cationic linkages targeting the EBOV VP24 mRNA in a cell free translation assay. PMOs used were 537-AUG (SEQ ID NO:34), 164-AUG+ (SEQ ID NO:40), 165-5'-term (SEQ ID NO:39) and 166-5'-term+ (SEQ ID NO:41).
Figure 17:
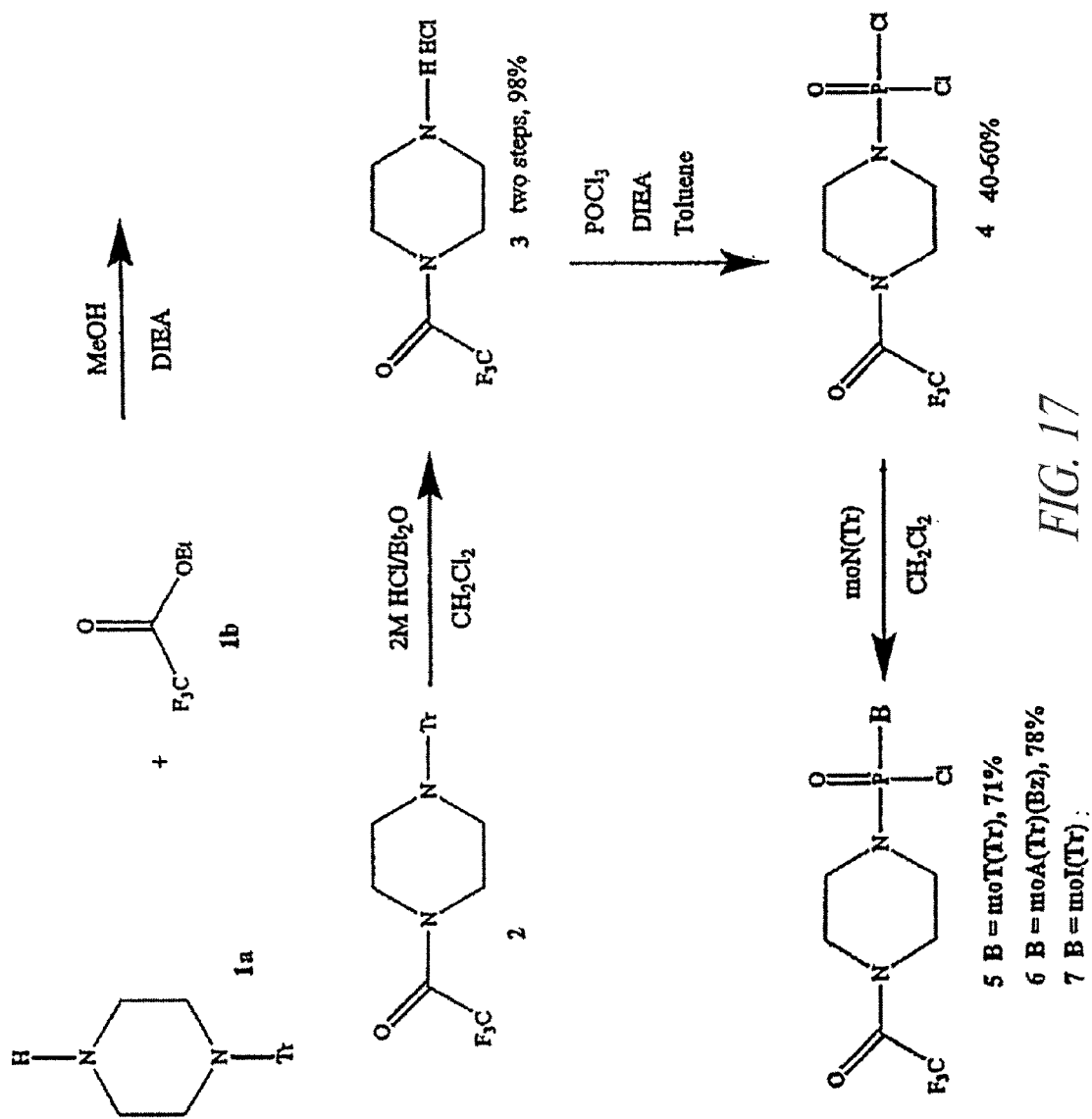
FIG. 17 shows the synthetic steps to produce subunits used to produce PMOplus containing the (1-piperazino) phosphinylideneoxy cationic linkage as shown in FIG. 2H.

Two PMOs were synthesized using cationic linkages for a subset of the oligomer linkages as shown in Sequence Listing for SEQ ID NOs:40 and 41. These oligomers incorporated the cationic linkage (1-piperazino phosphoramidate) shown in FIG. 2H at the positions indicated with a "+". These two PMOs target the EBOV VP24 mRNA. A cell free translation assay was performed using the VP24:luciferase mRNA as the input RNA. PMO with and without cationic linkages were compared for their ability to inhibit luciferase expression and the results are shown in FIG. 16. Compared to the uncharged PMO with the same base sequence, the PMOs with between 6 and 8 cationic linkages demonstrated between 10 and 100-fold increased antisense activity in this assay.

Based on the experiments performed in support of the invention as described above in the Examples, efficacious anti-filovirus PMOs have been identified.

The antiviral PMOs demonstrate favorable anti-Ebola viral activity both in vitro and in vivo in both rodents and non-human primates. Together, the compounds and methods of the present invention provide a highly efficacious therapeutic treatment regimen for lethal Ebola virus infections. PMOs have already been tested in clinical trials and have appropriate pharmacokinetic and safety profiles for use in humans (Arora and Iversen 2001). The results presented here have far-reaching implications for the treatment of highly lethal Ebola virus hemorrhagic fever, as well as diseases caused by other filovirus biothreats including Marburg virus.

Example 4

PMOplus Oligomers Provide Post-Exposure Protection Against Lethal Zaire Ebola and Marburg Virus Infection in Monkeys Zaire Ebola Virus (ZEBOV) and Marburg Virus (MARV) are highly virulent emerging pathogens of the family Filoviridae and are causative agents of viral hemorrhagic fever (HF). Nonhuman primate infection models closely reproduce the clinical, histopathologic, and pathophysiologic aspects of fatal filovirus hemorrhagic fever (HF) in man. Wild-type ZEBOV and MARV are highly lethal in nonhuman primate models of infection. Initial symptoms occur approximately 3-4 days following infection and include fever and lethargy as virus replicates to incipient detection levels in blood. Symptoms typically progress rapidly and include coagulation abnormalities such as frank hemorrhage, and thrombocytopenia; alteration of blood chemistry parameters (liver transaminases in particular); and immunological responses characterized by lymphocyte apoptosis and induction of proinflammatory cytokines. Death most often occurs 6-10 days following ZEBOV infection and 8-12 days after MARV infection. These non-human primate models were therefore used to test the protective abilities of AVI-6002 and AVI-6003 in Ebola and Marburg infections, respectively.

AVI-6002 is a combination therapeutic containing an approximately 1:1 mixture of equivalent concentrations (w/v) of PMOplus oligomers specific to the AUG start site region of Ebola VP24 (eVP24) and Ebola VP35 (eVP35). The eVP24-specific PMOplus (AVI-7537) oligomer contains five piperazine moieties at positions 3 (i.e., between bases 3 and 4), 8, 11, 14, and 16 along the phosphorodiamidate (PMO) backbone, and the eVP35-specific PMOplus (AVI-7539) oligomer contains five piperazines at positions 2, 7, 12, 15, and 18 along the PMO backbone (from 5' to 3').

AVI-6003 is a combination therapeutic containing a 1:1 mixture of equivalent concentrations (w/v) of PMOplus oligomers specific to the AUG start site region of Marburg NP (mNP) and Marburg VP24 (mVP24). The mNP-specific PMOplus (AVI-7288) oligomer contains five piperazine moieties at positions 10, 12, 14, 18, and 19 along the PMO backbone, and the mVP24-specific PMOplus (AVI-7287) oligomer contains six piperazine moieties at positions 6, 7, 9, 16, 17, and 20 along the PMO backbone. The mNP-specific PMOplus oligomer also contains an inosine base at position 12, and the VP24-specific PMOplus oligomer contains two inosine bases at positions 9 and 19. All PMOs were synthesized by AVI BioPharma, Inc. The sequences of AVI-6002 and AVI-6003 are shown in Table 13 below. Also indicated are the positions of the piperazine linkages (e.g., A+T) and the inosine bases.

TABLE 13

AVI-6002 and AVI-6003 PMOplus components and sequences

| Formulation Name | Target Transcript | Genomic Location[a] | PMO sequence[b] | SEQ ID NO: |
|---|---|---|---|---|
| AVI-6002 | | | | |
| AVI-7537 | ZEBOV VP24 | 10331-10349 | 5'-GCC+ATGGT+TTT+TTC+TC+AGG-3' | 77 |
| AVI-7539 | ZEBOV VP35 | 3133-3152 | 5'-CC+TGCCC+TTTGT+TCT+AGT+TG-3' | 78 |
| AVI6003 | | | | |
| AVI-7288 | MARV NP | 73-95 | 5'-GAATATTAAC+AI+AC+TGAC+A+AGTC-3' | 79 |
| AVI-7287 | MARV VP24 | 10204-10224 | 5'-CGTTGA+T+AI+TTCTGCC+A+TIC+T-3' | 80 |

[a]Sequence locations obtained from GenBank accession number NC_002549 for ZEBOV-Kikwit and NC_001608 for MARV-Musoke.
[b]Positively charged piperazine moieties (e.g., A + T) are incorporated at the indicated positions into phosphorodiamidate linkages forming the PMOplus backbone.

For the ZEBOV portion of the experiments rhesus monkeys were challenged with approximately 1,000 PFU of ZEBOV-Kikwit by intramuscular injection. In MARV challenge experiments, cynomolgus monkeys were injected subcutaneously with approximately 1,000 PFU of MARV-Musoke. Virus challenge stocks were prepared in Dulbecco's Modified Eagle Medium supplemented with 1% fetal bovine serum. All PMOplus test or control articles were dissolved in sterile PBS and were delivered by bolus injection to anesthetized (ketamine/acepromazine) animals. Intravenous injections were delivered via the saphenous vein. The routes of delivery for each experiment are indicated in the Figures or the Brief Description of the Drawings. In all experiments, PMOplus were administered beginning 30-60 minutes after challenge and were delivered daily for about 10-14 days (exact regimen is noted in individual Figure descriptions). Animals were monitored at least twice daily to record clinical symptoms of hemorrhagic fever. Animals surviving for 28 days were deemed to be protected.

Animal-infection experiments were performed under Biosafety Level 4 (BL4) containment facilities the United States Army Medical Research Institute of Infectious Diseases (US-AMRIID) in Frederick, Md. Research was conducted in compliance with the Animal Welfare Act and others federal statutes and regulations relating to animals and experiments involving animals. Animal experiments adhered to principles stated in the National Research Council's Guide for the Care and Use of Laboratory Animals and USAMRIID is fully accredited by the Association for Assessment and Accreditation of Laboratory Animal Care International.

Analytical Methods. The concentration of PMO in biological samples was determined either by high-performance liquid chromatography (HPLC) or by Biacore T100 label-free interaction analysis. The Biacore T100 (GE Healthcare) interaction analysis was performed utilizing the SA chip (GE Healthcare), which has complementary biotin-DNA immobilized to the chip surface. Plasma and urine samples were diluted and analyzed directly. Tissue homogenates were extracted using a filter plate (Whatman 7700-7236) with 2:1 acetonitrile: sample then lyophilized and reconstituted in buffer. Quantification of recovery was based upon comparison with a calibration curve, prepared under the same conditions as the samples being investigated. Analysis of PMO molecules extracted from trypsin-digested tissue homogenates and plasma was evaluated by HPLC as previously described (see Amantana, A., et al., *Bioconjugate Chemistry.* 18:1325-1331, 2007).

Virus Detection. Virus plaque assays were conducted by adding serially diluted sera to duplicate wells of Vero-cell monolayers. Virus plaques were quantified after 7-10 d incubation. Plaque visualization was facilitated by applying neutral-red agarose overlay for 24 h. For quantitative RT-PCR of ZEBOV RNA, plasma was treated with Trizol and RNA was extracted using standard chloroform/phenol techniques. ZEBOV-specific primers were used to amplify a region of the glycoprotein gene.

Blood chemistry, hematology, and cytokine analysis. Serum cytokines were quantified using a BioRad system analyzed using Luminex technology according to manufacturer's directions. Blood chemistry profiles were determined from plasma using a Piccolo Xpress Chemistry Analyzer (Abaxis) fitted with a General Chemistry 13 reagent disc. Hematologic parameters were analyzed using Beckman/Coulter Act10 instrumentation according to the manufacturers recommended protocol.

Statistical Analysis. Animals were randomly assigned to experimental groups using SAS software. T-test with step-down bootstrap adjustment was conducted to compare mean platelet, lymphocyte, AST, and MARV viremia between the PMOplus negative-control group and each treatment group at each time point. For AST values that exceeded instrument quantification limits, we substituted the highest quantifiable value (as defined by instrument manufacturer) for statistical analysis. ZEBOV viremia data did not meet normality and homogeneity of variance requirements for parametric analysis. As a result the Wilcoxon-Mann-Whitney test was utilized with Sidak adjustment for multiple comparisons at each time point. Survival differences between treatment groups and the PMOplus negative-control group were determined using log-rank analysis. Pair-wise comparisons were considered statistically significant at P-values $\leq 0.05$.

Figure 18A:
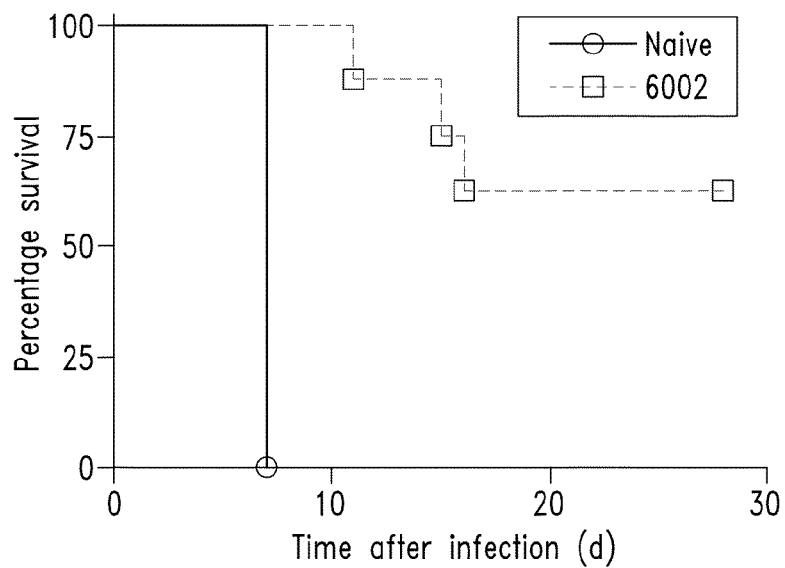
FIGS. 18A-F shows the results of post-exposure protection of Zaire Ebola virus (ZEBOV)-infected rhesus monkeys by AVI-6002. In all experiments, monkeys were challenged with approximately 1,000 plaque forming units of ZEBOV-Kikwit by intramuscular injection, and PMOplus were administered in PBS beginning 30-60 min after challenge.

The results of two independent ZEBOV infection experiments are shown in FIGS. 18A-F. FIG. 18A shows the results of an initial experiment, in which an untreated monkey developed progressive clinical signs consistent with ZEBOV HF and succumbed to infection on day 7, whereas five out of eight (62.5%) of AVI-6002-treated animals survived ZEBOV infection. For this experiment, treatments were administered using a combination of subcutaneous and intraperitoneal delivery routes.

Figure 18B:
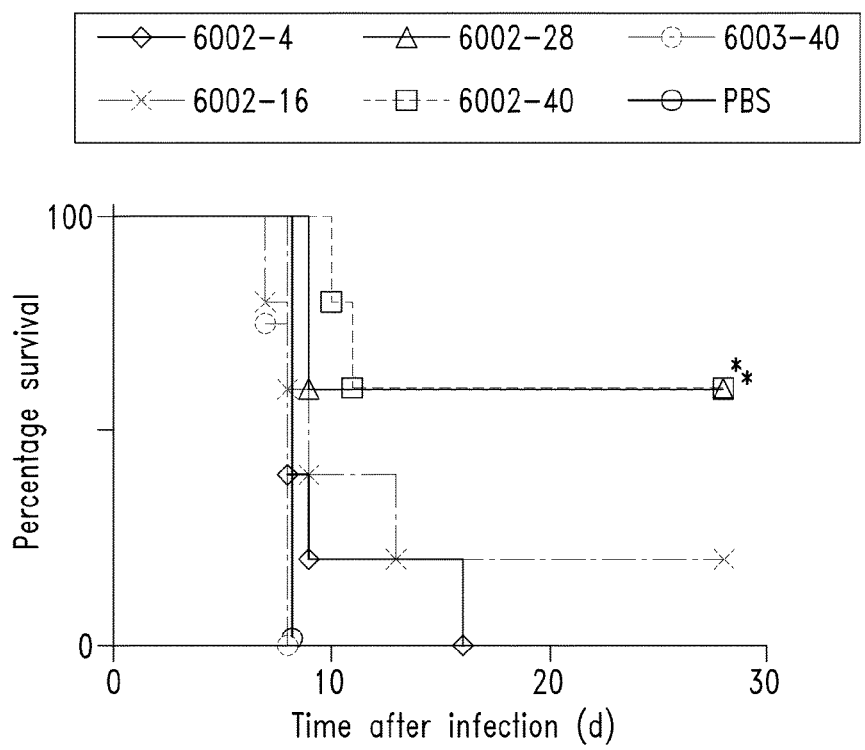
Figure 18C:
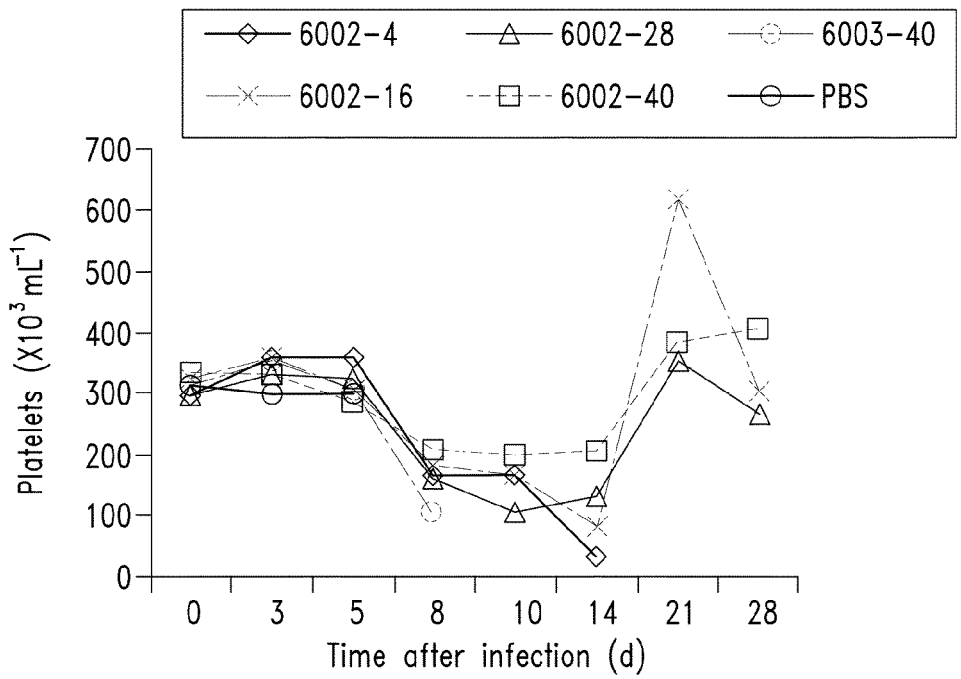
Figure 18D:
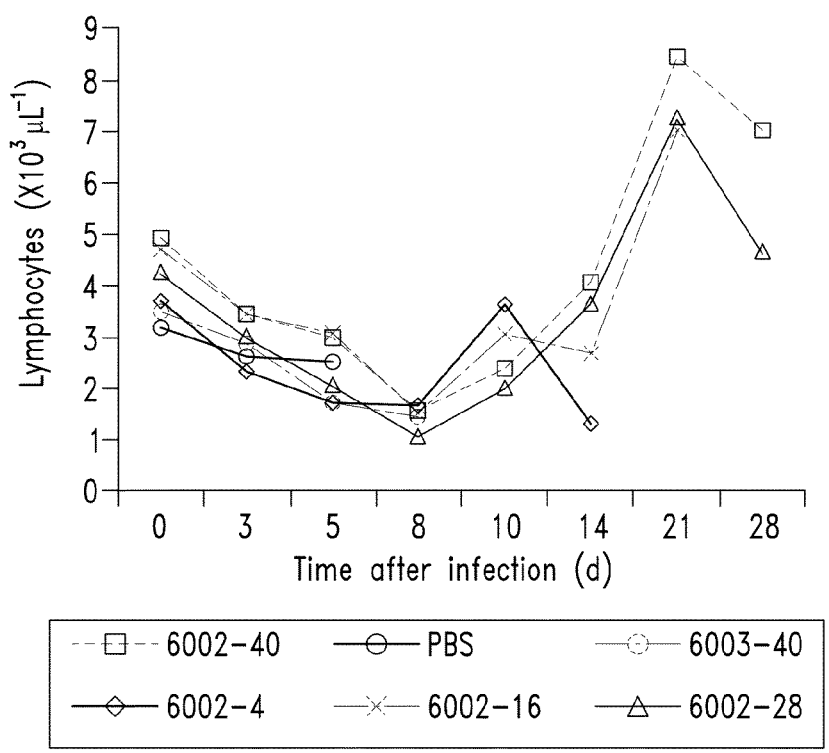

Following the promising results obtained from this initial experiment, the post-exposure efficacy of AVI-6002 was then explored in a randomized, single-blind, multiple-dose evaluation. To control for possible off-target effects, four monkeys were treated with AVI-6003 (n=4), a negative-control PMOplus combination containing two MARV-specific molecules, which lacks complementarity to ZEBOV targets. In this experiment, treatments were delivered by intravenous administration to mirror treatment approaches that may be used following accidental needlestick injuries occurring in research or medical settings. FIG. 18B shows the results these experiments, in which all phosphate buffered saline (PBS)-treated and AVI-6003 (MARV-specific negative control)-treated animals succumbed by day 8 post infection after developing characteristic HF signs such as fever and petechia, whereas 60% (three out of five) of the monkeys in each of the groups treated with either 28 or 40 mg/kg AVI-6002 survived. A gradient of protective efficacy was observed in treatments groups receiving 16 (20% survival) and 4 mg/kg AVI-6002 (no survivors).

Figure 18E:
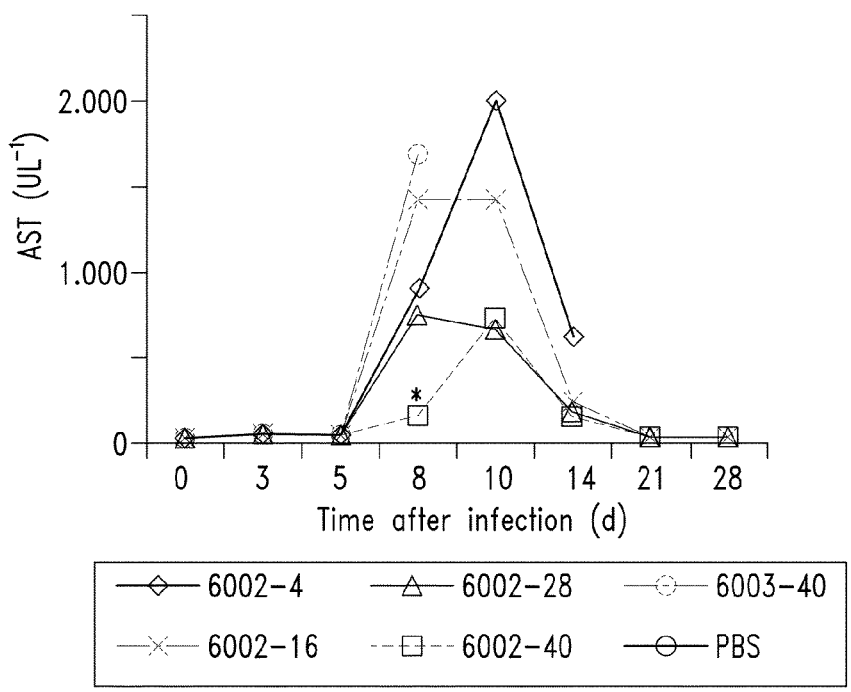
Figure 18F:
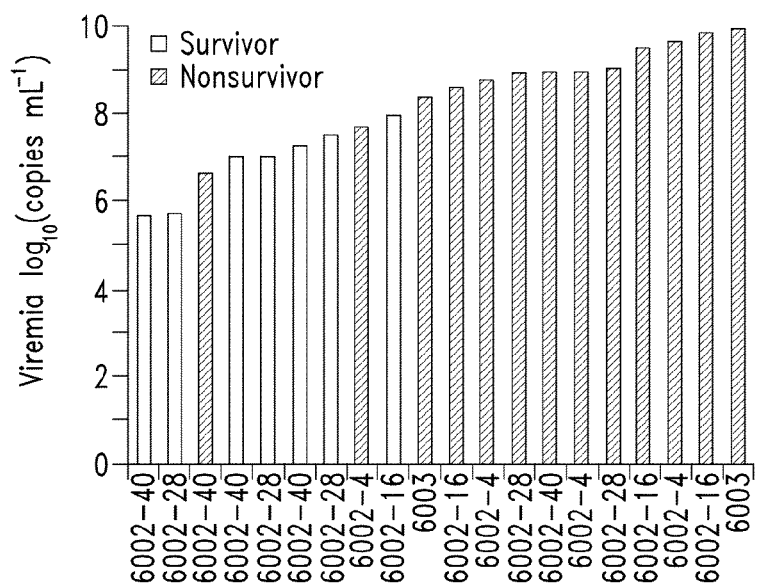
Figure 20A:
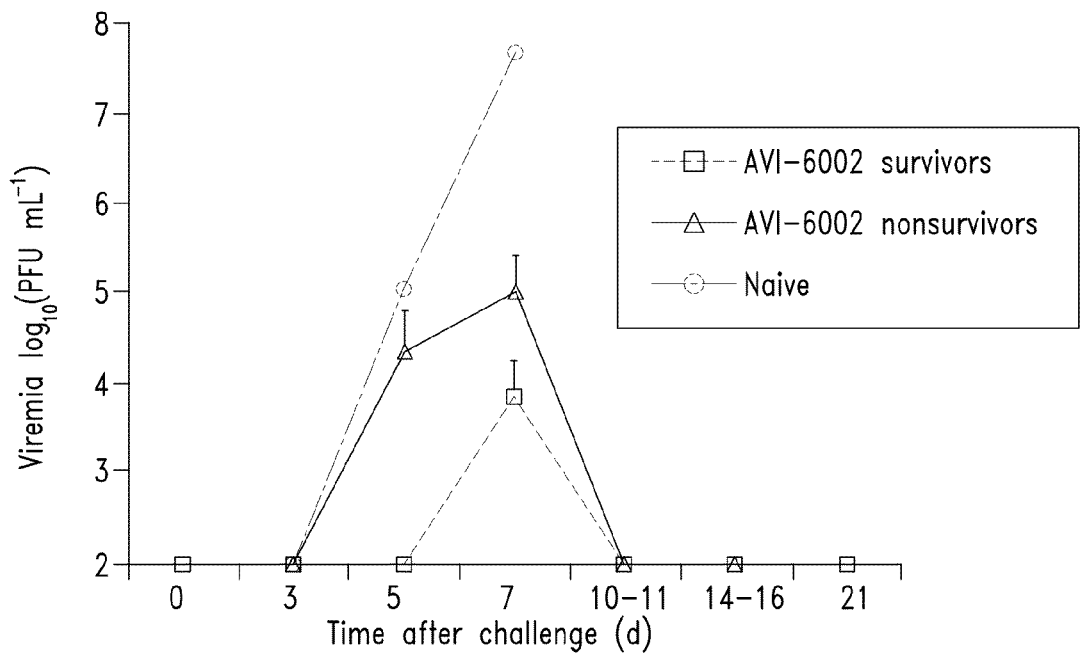
FIG. 20 shows that treatment with AVI-6002 protected rhesus monkeys against ZEBOV. Animals were infected with approximately 1,000 PFU of ZEBOV by intramuscular injection. AVI-6002 was administered in PBS daily at 40 mg/kg starting 30-60 min after challenge and continuing for 10 days in one treatment group (n=4) or 14 days in a second treatment group (n=4). Treatments were administered by injecting equal volumes at subcutaneous and intraperitoneal sites. A single untreated monkey served as a naïve infection-control subject. Average plasma viremia (FIG. 20A), aspartate aminotransferase (AST) (FIG. 20B), serum IL-6 (FIG. 20C) and MCP-1 (FIG. 20D) values from naïve, non-surviving (n=3) and surviving (n=5) animals from two experiments are displayed.
Figure 20B:
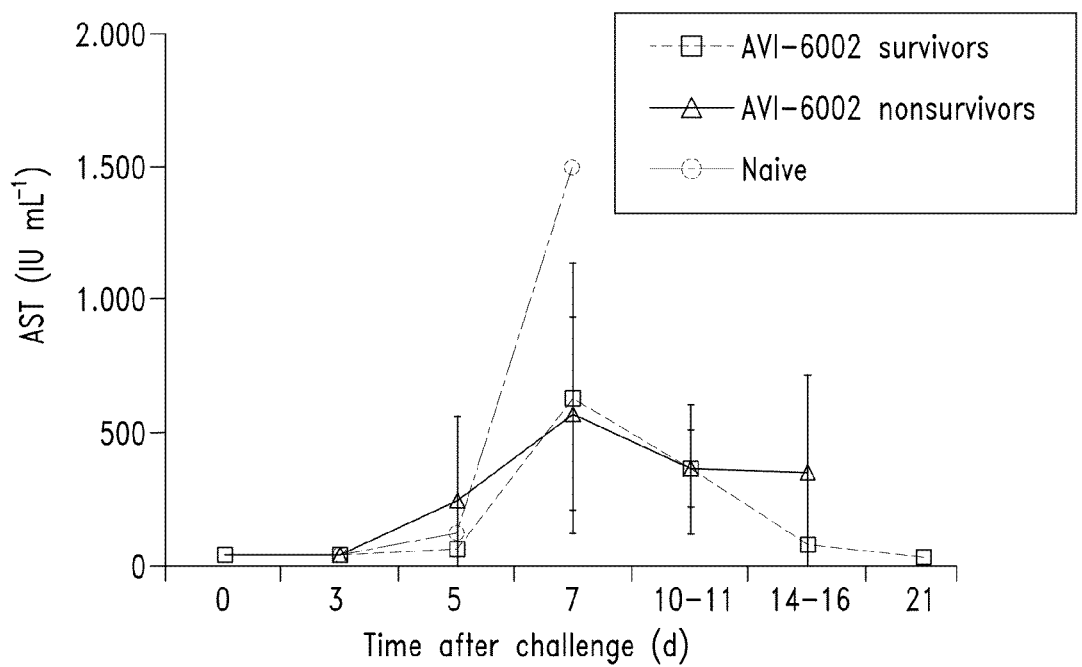
Figure 20C:
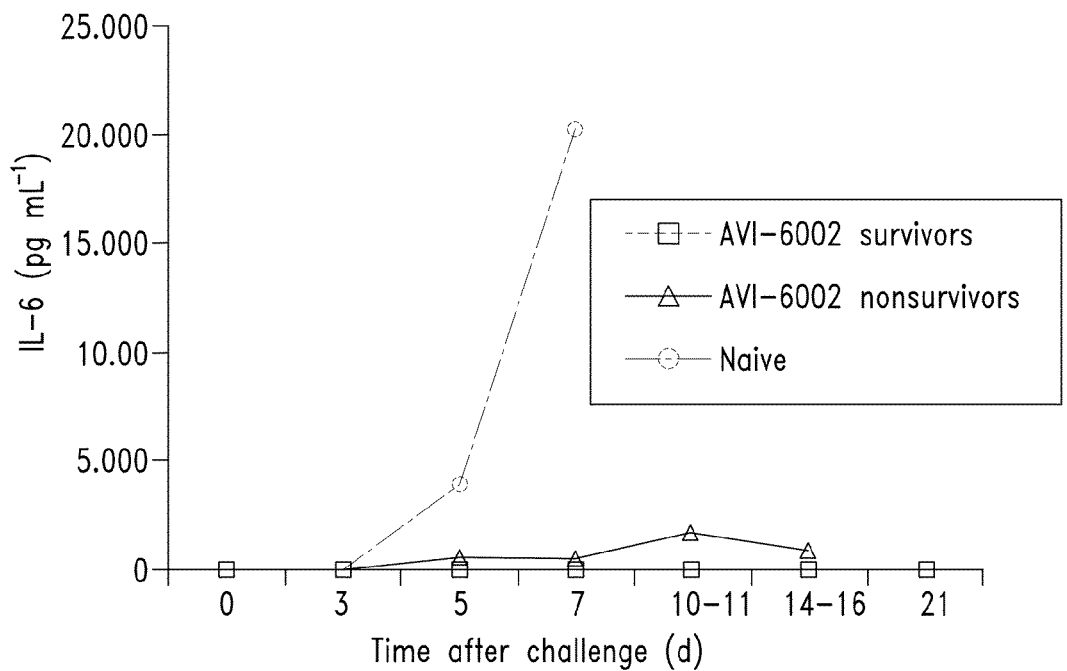
Figure 20D:
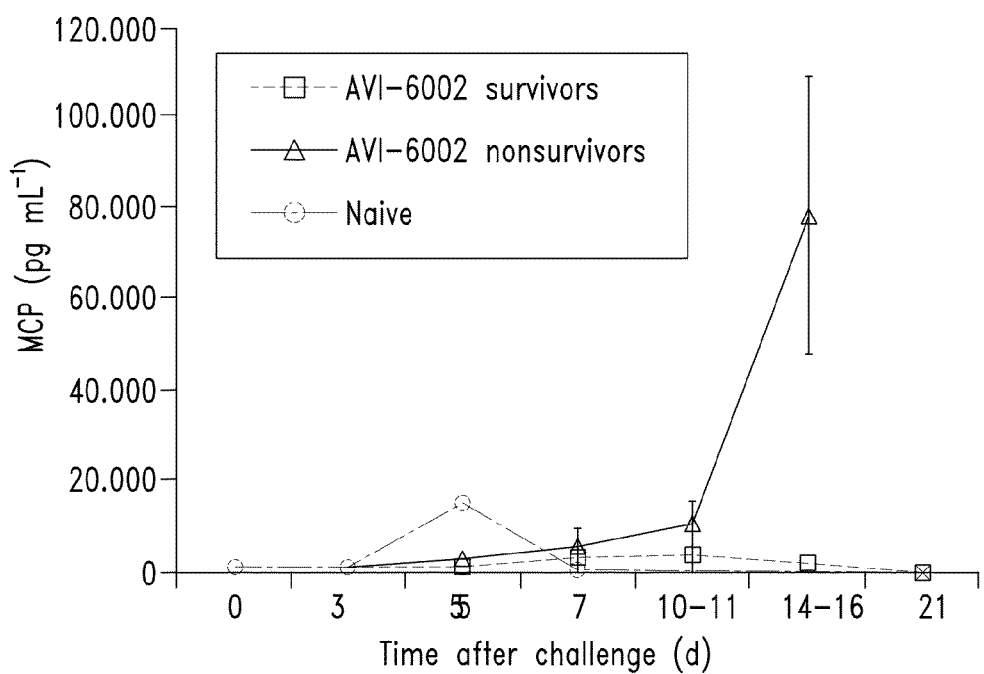

While the severity of thrombocytopenia (FIG. 18C) and lymphocytopenia (FIG. 18D), observed in all treatment groups through day 8, was unaffected by AVI-6002 treatments, platelets and lymphocytes rebounded in survivors, indicative of disease resolution. Administration of 28 or 40 mg/kg AVI-6002 mitigated indices of liver damage such as serum AST (FIG. 18E). At the peak of plasma viremia (occurring on day 8 post infection in all animals) mean viral load in AVI-6002-treated monkeys (40 mg/kg dose level) was suppressed approximately 100-fold relative to that of AVI-6003-treated control monkeys (analysis not shown). Viremia levels in animals that survived to day 8 were generally well correlated with survival (FIG. 18F), suggesting that suppression of viral replication may be a critical mechanism of AVI-6002-mediated protection. In surviving animals, plasma viremia (FIG. 20A) and circulating levels of aspartate aminotransferase (AST) (FIG. 20B), interleukin-6 (IL-6) (FIG. 20C) and monocyte chemotactic protein-1 (MCP-1)(Figure 20D) suggest that administration of AVI-6002 successfully suppressed virus replication, liver damage, and potentially harmful inflammatory responses.

Figure 19A:
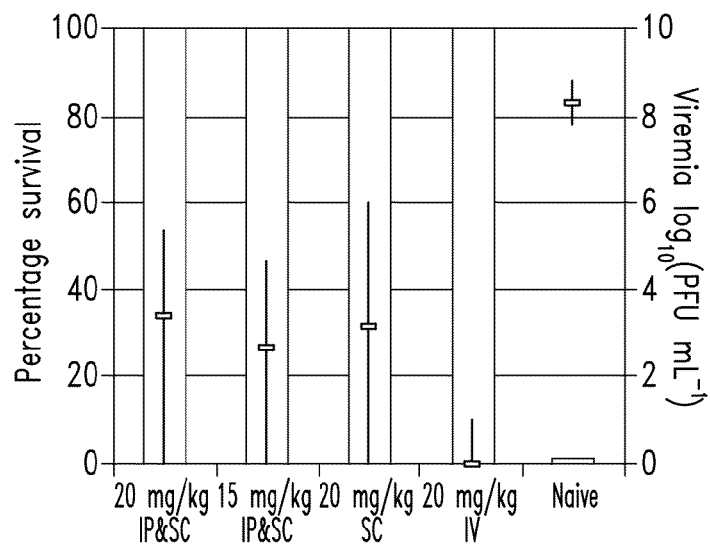
FIGS. 19A-F show the results of post-exposure protection of Marburg virus (MARV)-infected cynomolgus monkeys by AVI-6003. In all experiments, monkeys were challenged with approximately 1,000 PFU of MARV-Musoke by subcutaneous injection, and treatments were initiated beginning 30-60 min after challenge and were administered daily through day 14 post-infection. PMOplus oligomers were formulated in PBS for delivery.

The results of two different MARV infection experiments are shown in FIGS. 19A-F. For one experiment, treatments were initiated 30-60 minutes following infection and AVI-6003 was delivered using one of four treatment strategies, as indicated in FIG. 19A (SC=subcutaneous; IP=intraperitoneal; IV=intravenous). Untreated, infection-control subjects became moribund and were euthanized on day 9 post infection after developing clinical signs characteristic of MARV infection. In contrast, treatment with AVI-6003 completely protected all 13 monkeys, regardless of dose or route of administration, and suppressed plasma viremia in all groups relative to controls (see FIG. 19A).

Figure 19B:
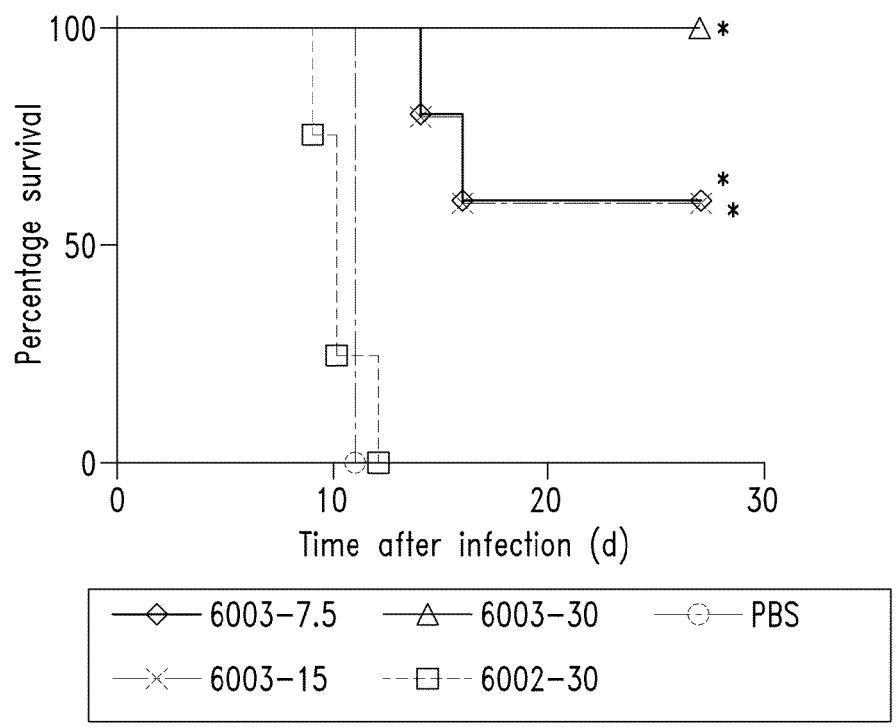
Figure 19C:
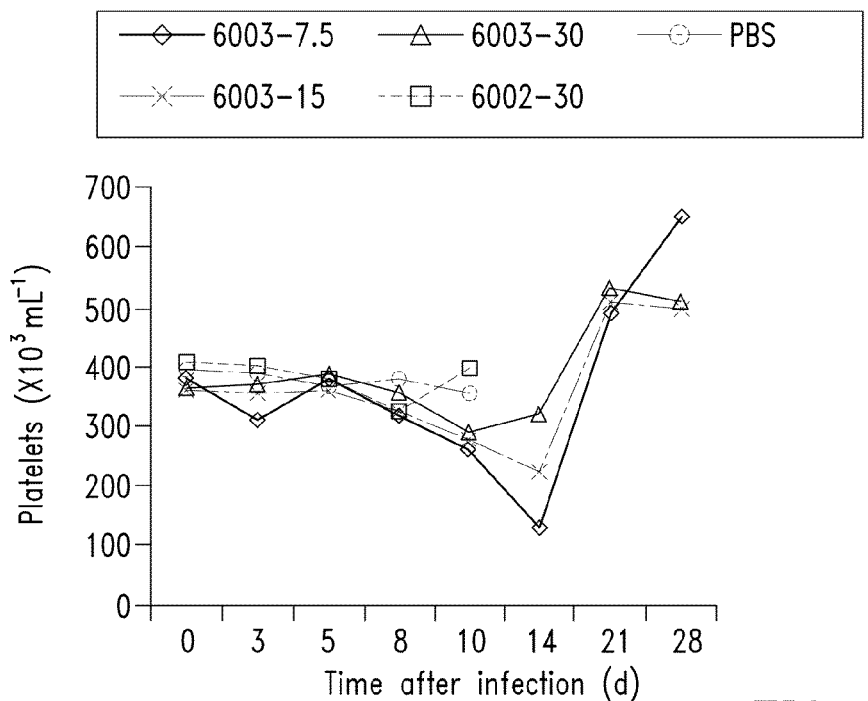
Figure 19D:
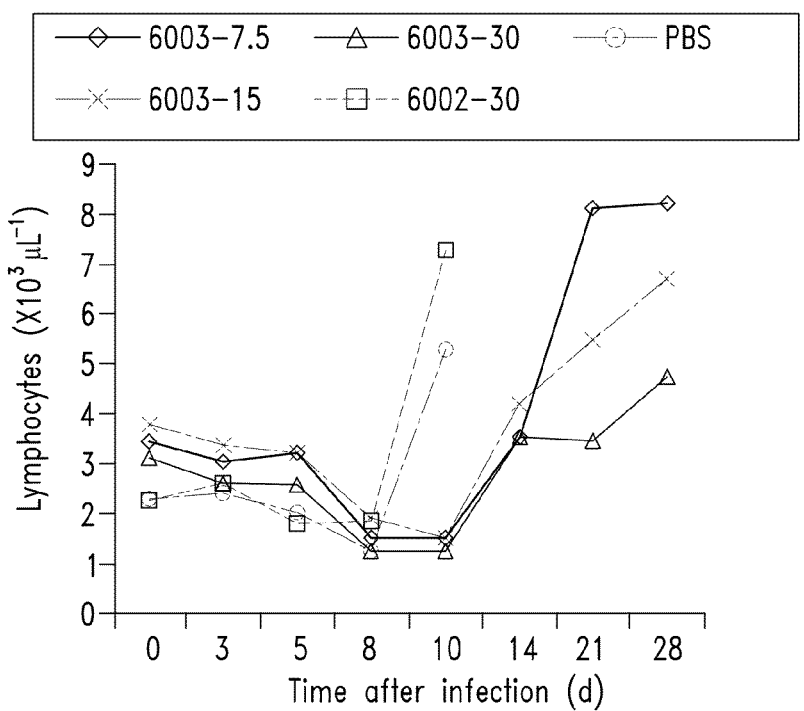
Figure 19E:
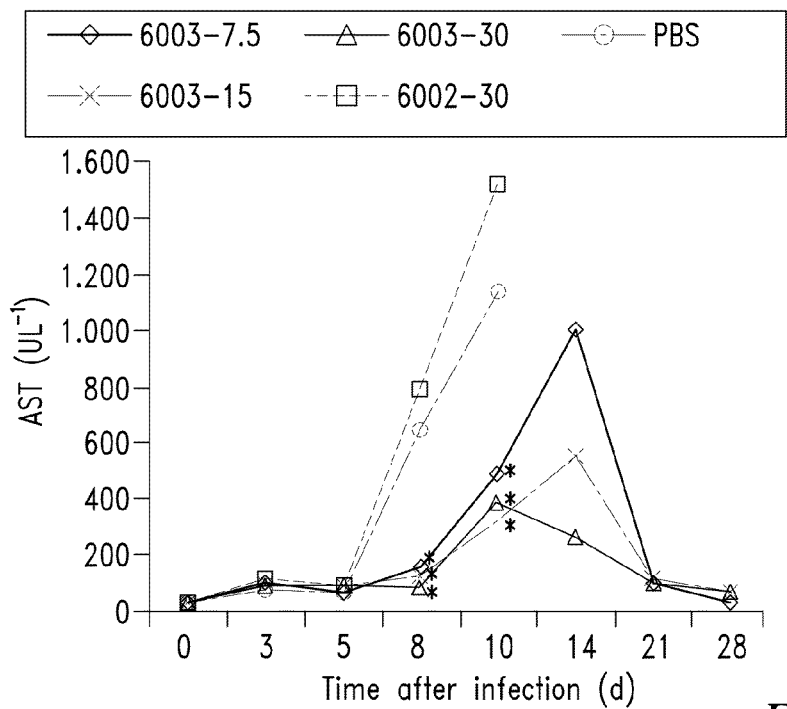
Figure 19F:
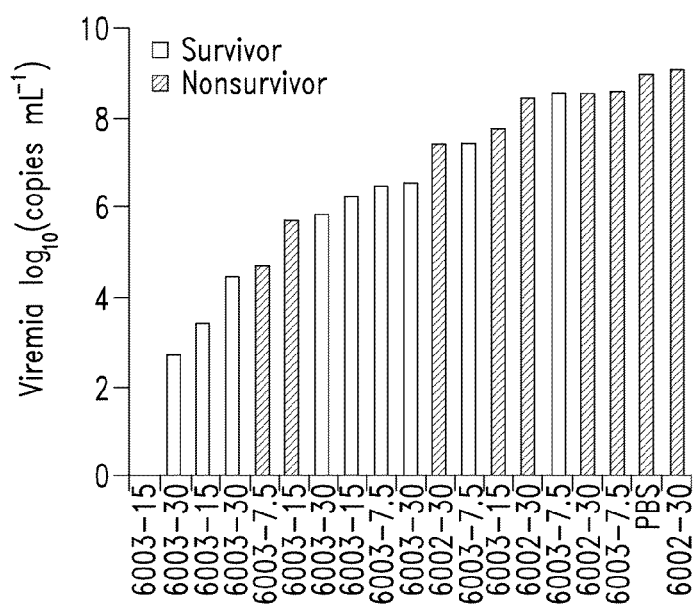

To determine the post-exposure therapeutic dose range of AVI-6003 and to rule out possible protection by nonspecific mechanisms, a randomized, multiple-dose, negative-PMOplus controlled study using single-blind experimental conditions was then conducted. Twenty cynomolgus monkeys were infected with a lethal dose of MARV-Musoke, and animals were intravenously treated with either PBS, AVI-6002 (negative control), or one of three doses of AVI-6003 beginning 30-60 min following infection. As shown in FIG. 19B, control animals treated with either PBS or AVI-6002 died on days 9-12, showing clinical signs characteristic of MARV HF including petechia, weight loss, fever and/or lethargy. One monkey, treated with 30 mg/kg AVI-6003, died unexpectedly due to complications of anesthesia on day 12 and was excluded from the survival analysis. All four remaining animals treated with 30 mg/kg AVI-6003 survived the infection and three out of five (60%) of monkeys in each of the groups treated with either 7.5 or 15 mg/kg survived. In AVI-6003-treated animals that succumbed to infection, mean time-to-death was delayed by >4 days relative to that of control subjects. While administration of AVI-6003 generally provided little protective effect against MARV-induced thrombocytopenia (FIG. 19C) and lymphocytopenia (FIG. 19D), AVI-6003 significantly reduced circulating levels of AST (FIG. 19E) relative to control treatments at days 8 and 10 post infection. Analysis of peak viremia levels in individual animals suggests that AVI-6003 mediated protection, at least in part, by reducing viral burden (FIG. 19F).

Taken together these studies provide an important advancement in therapeutic development efforts for treatment of filovirus hemorrhagic fever. Although the 30-60 min interval between virus exposure and initiation of treatment we used in these experiments reflects a timing useful for treating accidental exposures in research or medical settings, the efficacy of delayed treatment we observed in the mouse model of infection (see Example 6 below) suggests that the window for effective treatment in primates may be wider than previously tested.

PMOplus agents possess multiple drug properties favorable for further development for use in humans to counter filoviruses or other highly virulent emerging viruses. PMOplus agents are highly stable, and can be rapidly synthesized, purified, and evaluated for quality. They are readily amenable to formulation in isotonic solutions, and, as shown herein, are efficacious by a number of delivery routes. Moreover, PMOplus are well tolerated in primates and multiple laboratory-animal species, and possess favorable pharmacokinetic properties (see Example 5, below). Both AVI-6002 and AVI-6003 have received approval by the US Food and Drug Administration for Investigational New Drug applications.

Example 5

Pharmacokinetics of PMOplus Oligomers

Pharmacokinetic evaluations of AVI-6002 and AVI-6003 were conducted in uninfected Spraque-Dawley rats obtained from Charles River Laboratories and were housed at Oregon State University Laboratory Animal Resources. PMOs were delivered via catheter to the right jugular vein. Catheters were surgically implanted by the supplier 2-4 d prior to shipping and head-mounted venous access ports were used to draw blood and deliver PMOs. Rats were housed in steel metabolism cages, which allowed for collection of urine samples. The results are shown in Tables 14 and 15 below. Table 14 shows a comparison of plasma and urine kinetics following a single intravenous or intraperitoneal dose of AVI-6002 in rats, and Table 15 shows a summary of plasma and urine kinetics of single 32.8 mg/kg intravenous or intraperitoneal dose of AVI-6003 in rats.

TABLE 14

Comparison of plasma and urine kinetics following a single intravenous or intraperitoneal dose of AVI-6002 in rats

|  | IV Administration[a] | | IP Administration[b] | |
| --- | --- | --- | --- | --- |
|  | AVI-7537 | AVI-7539 | AVI-7537 | AVI-7539 |
| Plasma | | | | |
| $C^0_{pl}$ (µg mL$^{-1}$) | 12.36 | 23.77 | 1.16 | 20.63 |
| $t_{1/2}$ (h) | 2.98 | 2.58 | 4.98 | 2.86 |
| Vd (L) | 0.40 | 0.21 | 1.30 | 2.37 |
| AUC (µg * min mL$^{-1}$) | 1242 | 2155 | 375 | 1935 |
| $CL_{TOT}$ (mL min$^{-1}$) | 4.03 | 2.32 | 13.69 | 10.47 |
| Tmax (h) | — | — | 1.07 | 0.83 |
| Cmax (µg mL$^{-1}$) | 16.73 | 35.92 | 1.84 | 9.3 |

TABLE 14-continued

Comparison of plasma and urine kinetics following a single intravenous or intraperitoneal dose of AVI-6002 in rats

|  | IV Administration[a] | | IP Administration[b] | |
| --- | --- | --- | --- | --- |
|  | AVI-7537 | AVI-7539 | AVI-7537 | AVI-7539 |
| Urine | | | | |
| Cum Ae (mg) | 0.16 | 0.42 | 0.0069 | 0.286 |
| % Dose | 3.0 | 8.0 | 0.14 | 5.7 |
| $t_{1/2}$ renal (h) | 5.24 | 4.94 | 3.19 | 5.33 |

[a] AVI-6002 was delivered to four male Sprague-Dawley rats via a single intravenous dose containing 35 mg/kg total PMOplus. Values of the individual PMOplus components (AVI-7537 and AVI-7539) were derived from serum and urine samples obtained at 0.2, 0.5, 1, 2, 4, 8, 12, and 24 h following AVI-6002 delivery.
[b] AVI-6002 was administered to four male Sprague-Dawley rats via a single intraperitoneal injection containing 36 mg/kg total PMOplus.

TABLE 15

Summary of plasma and urine kinetics of single 32.8 mg/kg intravenous or intraperitoneal dose of AVI-6003 in rats

|  | IV Administration[a] | | IP Administration[b] | |
| --- | --- | --- | --- | --- |
|  | AVI-7288 | AVI-7287 | AVI-7288 | AVI-7287 |
| Plasma | | | | |
| $C^0_{pl}$ (µg mL$^{-1}$) | 19.8 | 29.8 | 4.90 | 5.34 |
| $t_{1/2}$ (h) | 0.82 | 0.78 | 4.82 | 3.83 |
| Vd (L) | 0.25 | 0.17 | 1.03 | 1.61 |
| AUC (µg * min mL$^{-1}$) | 434 | 612 | 972 | 584 |
| $CL_{TOT}$ (mL min$^{-1}$) | 11.5 | 8.2 | 5.28 | 10.6 |
| Tmax (h) | — | — | 1.25 | 1.0 |
| Cmax (µg mL$^{-1}$) | 18.3 | 26.8 | 4.38 | 3.98 |
| Urine | | | | |
| Cum Ae (mg) | 1.69 | 1.13 | ND | ND |
| % Dose | 34 | 23 | ND | ND |
| CL ren (mL min$^{-1}$) | 5.46 | 11.26 | ND | ND |
| $t_{1/2}$ renal (h) | 3.85 | 4.35 | ND | ND |

[a] AVI-6003 was delivered to four male Sprague-Dawley rats via a single intravenous dose containing 32.8 mg/kg total PMOplus. Values of the individual PMOplus components (AVI-7288 and AVI-7287) were derived from serum and urine samples obtained at 0.2, 0.5, 1, 2, 4, 8, 12, and 24 h following AVI-6002 delivery.
[b] A single 37.4 mg/kg dose of AVI-6003 was delivered by intraperitoneal injection.
ND = Not Determined.

Example 6

Figure 21:
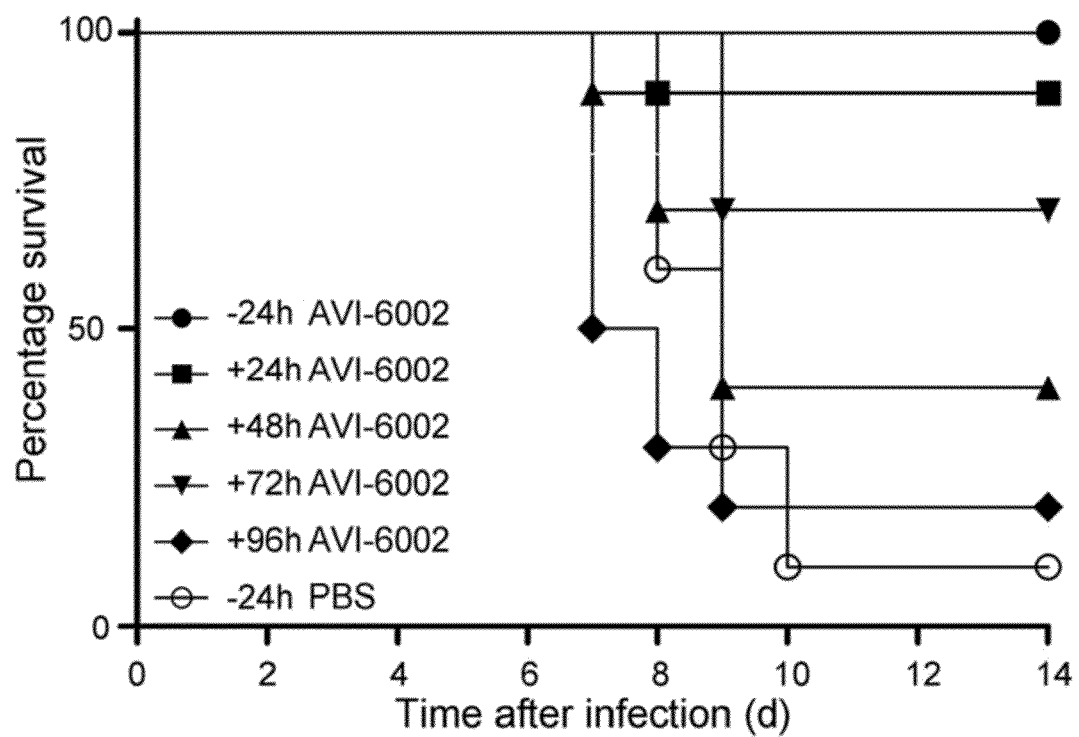
FIG. 21 shows that delayed treatment with AVI-6002 protects mice against mouse-adapted ZEBOV, as measured by percentage survival after infection. AVI-6002 (10 mg/kg) or PBS vehicle were delivered to C57BL/6 mice (n=10) by IP injection at the indicated times relative to infection. AVI-6002 was diluted in PBS for delivery. Mice were infected with 1,000 PFU of mouse-adapted EBOV-Z delivered by intraperitoneal injection and animal health was monitored for 14 days.

Delayed Treatment With PMOplus Oligomers Protects Mice Against Mouse-Adapted Zaire Ebola Virus To further evaluate the window for effective intervention in nonhuman models of Filovirus infection, C57BL/6 mice (n=10; aged 8-12 weeks) were infected with approximately 1,000 PFU of a mouse-adapted strain of ZEBOV by intraperitoneal injection, and treated with antisense agents at 24, 48, 72, and 96 hours post-infection. Antisense agents were diluted in PBS and delivered to C57BL/6 mice (n=10) by IP injection. Animal health was monitored daily and mice surviving for 14 days were deemed to be protected. As shown in FIG. 21, delayed treatment with AVI-6002 increased survival rates compared to untreated (PBS) controls, and thus protected mice against lethal ZEBOV infection.

Sequence Listing Table

| AVI No. | Name | Target Sequences 5'-3' | SEQ ID NO |
|---|---|---|---|
| NA | VP35-AUG | AAUGAUGAAGAUUAAAACCUUCAUCAUCCUUA CGUCAAUUGAAUUCUCUAGCACUCGAAGCUUA UUGUCUUCAAUGUAAAAGAAAAGCUGGUCUAA CAAGAUGACAACUAGAACAAAGGGCAGGG | 1 |
| NA | VP24-AUG | CGUUCCAACAAUCGAGCGCAAGGUUUCAAGGU UGAACUGAGAGUGUCUAGACAACAAAAUAUUG AUACUCCAGACACCAAGCAAGACCUGAGAAAA AACCAUGGCUAAAGCUACGGGACGAUACA | 2 |
| NA | VP30-AUG | AGAUCUGCGAACCGGUAGAGUUUAGUUGCAAC CUAACACACAUAAAGCAUUGGUCAAAAAGUCA AUAGAAAUUUAAACAGUGAGUGGAGACAACUU UUAAAUGGAAGCUUCAUAUGAGAGAGGAC | 3 |
| NA | VP40-AUG | AAACCAAAAGUGAUGAAGAUUAAGAAAAACCU ACCUCGGCUGAGAGAGUGUUUUUUCAUUAACC UUCAUCUUGUAAACGUUGAGCAAAAUUGUUAA AAAUAUGAGGCGGGUAUAUUGCCUACUG | 4 |
| NA | L-AUG | GUAGAUUAAGAAAAAGCCUGAGGAAGAUUAA GAAAAACUGCUUAUUGGGUCUUUCCGUGUUUU AGAUGAAGCAGUUGAAAUUCUUCCUCUUGAUA UUAAAUGGCUACACAACAUACCCAAUAC | 5 |
| NA | NP-AUG | UGAACACUUAGGGGAUUGAAGAUUCAACAACC CUAAAGCUUGGGGUAAAACAUUGGAAAUAGUU AAAAGACAAAUUGCUCGGAAUCACAAAAUUCC GAGUAUGGAUUCUCGUCCUCAGAAAAUCU | 6 |
| NA | Str. Ihn 1(-) | UAAAAAUUCUUCUUUCUUUUUGUGUGUCCG | 7 |
| NA | VP35-AUG | CUAAAAAUCGAAGAAUAUUAAAGGUUUUCUUU AAUAUUCAGAAAAGGUUUUUUAUUCUCUUCUU UCUUUUUGCAAACAUAUUGAAAUAAUAAUUUU CACAAUGUGGGACUCAUCAUAUAUGCAAC | 8 |
| NA | VP24-AUG | UUCAUUCAAACACCCCAAAUUUUCAAUCAUAC ACAUAAUAACCAUUUUAGUAGCGUUACCUUUC AAUACAAUCUAGGUGAUUGUGAAAAGACUUCC AAACAUGGCAGAAUUAUCAACGCGUUACA | 9 |
| NA | VP30-AUG | GAAGAACAUUAAGUGUUCUUUGUUAGAAUUAU UCAUCCAAGUUGUUUUGAGUAUACUCGCUUCA AUACAACUUCCCUUCAUAUUUGAUUCAAGAUU UAAAAUGCAACAACCCCGUGGAAGGAGU | 10 |
| NA | VP40-AUG | UCCCAAUCUCAGCUUGUUGAAUUAAUUGUUAC UUAAGUCAUUCUUUUUAAAAUUAAUUCACACA AGGUAGUUUGGGUUUAUAUCUAGAACAAAUUU UAAUAUGGCCAGUUCCAGCAAUUACAACA | 11 |
| NA | L-AUG | UCAUUCUCUUCGAUACACGUUAUAUCUUUAGC AAAGUAAUGAAAAAUAGCCUUGUCAUGUUAGAC GCCAGUUAUCCAUCUUAAGUGAAUCCUUUCUU CAAUAUGCAGCAUCCAACUCAAUAUCCUG | 12 |
| NA | NP-AUG | CACACAAAAACAAGAGAUGAUGAUUUUGUGUA UCAUAUAAAUAAAGAAGAAUAUUAACAUUGAC AUUGAGACUUGUCAGUCUGUUAAUAUUCUUGA AAAGAUGGAUUUACAUAGCUUGUUAGAGU | 13 |
| NA | Str Ihn 1(-) | CAAAAUCAUCAUCUCUUGUUUUUGUGUGUC | 14 |
| Ebola Virus Oligomer Targeting Sequences (5'-3') | | | |
| 305 | Str. Inh. 1 | CGGACACACAAAAAGAAAGAAG | 15 |
| 309 | L-AUG | GTAGCCATTTAATATCAAGAGG | 16 |
| 538 | L'-AUG | TGGGTATGTTGTGTAGCCAT | 17 |
| 1156 | L-29-AUG | CAAGAGGAAGAATTTCAACTGC | 18 |

-continued

| | Sequence Listing Table | | |
|---|---|---|---|
| 1157 | L + 4-AUG | GTATTGGGTATGTTGTGTAGC | 19 |
| 1158 | L + 11-AUG | CGTCTGGGTATTGGGTATGTT | 20 |
| 413 | VP35-AUG | GTTGTCATCTTGTTAGACCAGC | 21 |
| 539 | VP35'-AUG | CCTGCCCTTTGTTCTAGTTG | 22 |
| 565 | VP35-22-AUG | GATGAAGGTTTTAATCTTCATC | 23 |
| 540 | VP35-19-AUG | GTCATCTTGTAGACCAGC | 24 |
| 541 | VP35-16-AUG | GTCATCTTGTTAGACC | 25 |
| 1151 | VP35 + 2-AUG | CCTGCCCTTTGTTCTAGTTGTC | 26 |
| 534 | NP-AUG | GGACGAGAATCCATACTCGG | 27 |
| 1147 | NP + 4-AUG | CAGATTTTCTGAGGACGAGAATC | 28 |
| 1148 | NP + 11-AUG | CATCCAGATTTTCTGAGGAC | 29 |
| 1149 | NP + 18-AUG | CTCGGCGCCATCCAGATTTTC | 30 |
| 1150 | NP-19-AUG | CATACTCGGAATTTTGTGATTC | 31 |
| 535 | VP40-AUG | GGCAATATAACCCGCCTC | 32 |
| 536 | VP30-AUG | CCATTTAAAAGTTGTCTCC | 33 |
| 537 | VP24-AUG | GCCATGGTTTTTTCTCAGG | 34 |
| 1152 | VP24-28-AUG | CTCAGGTCTTGCTTGGTGTC | 35 |
| 1153 | VP24 + 4-AUG | TGTATCGTCCCGTAGCTTTAGC | 36 |
| 1154 | VP24 + 10-AUG | GATTGTATCGTCCCGTAGC | 37 |
| 1155 | VP24 + 19-AUG | GGCGATATTAGATTGTATCGTC | 38 |
| 0165 | VP24-5'trm | TTCAACCTTGAAACCTTGCG | 39 |
| 0164 | VP24(8+)-AUG | GCCA+TGG+T+T+T+T+TC+TCAGG | 40 |
| 0166 | VP24-5'trm(6+) | +T+TCAACC+T+TGAAACC+T+TGCG | 41 |
| NA | panVP35 | GATGAAGGTTTTAATCTTCATC | 42 |
| NA | Scr/3 | TTTTTCTTAATCTTCATC | 43 |
| | Marburg Virus Oligomer Targeting Sequences (5'-3') | | |
| NA | (-)3'term | GACACACAAAAACAAGAGATG | 44 |
| NA | L-AUG | GCTGCATATTGAAGAAAGG | 45 |
| 0177 | L + 7-AUG | CATCAGGATATTGAGTTGGATG | 46 |
| NA | VP35-AUG | GTCCCACATTGTGAAAATTAT | 47 |
| 0178 | VP35 + 7-AUG | CTTGTTGCATATATGATGAGTC | 48 |
| NA | NP-AUG | GTAAATCCATCTTTTCAAG | 49 |
| 0173 | NP-6-AUG | CAAGCTATGTAAATCCATCTTTTC | 50 |
| 0174 | NP + 4-AUG | CCTAACAAGCTATGTAAATC | 51 |
| 0176 | NP-5'SL | TAACAGACTGACAAGTCTCAA | 52 |
| NA | NP-5'UTR | CAATGTTAATATTCTTCTTTA | 53 |
| 0175 | NP-5'UTRb | ATATTCTTCTTTATTTATATGT | 54 |
| NA | VP30-AUG | GTTGCATTTTAAATCTTGAATC | 55 |
| NA | VP35-5'UTR | CCTTTAATATTCTTCGATTT | 56 |

-continued

Sequence Listing Table

| 0179 | VP24 + 5-AUG | GTTGTAACGCGTTGATAATTCTG | 57 |
|---|---|---|---|
| NA | NP-stem loop | CAAGTCTCAATGTCAATGTT | 58 |

Control Oligomers

| 183 | DSscr | AGTCTCGACTTGCTACCTCA | 59 |
|---|---|---|---|
| 542 | Scr | TGTGCTTACTGTTATACTACTC | 60 |

Peptide Conjugates*

| NA | R9F2C | NH$_2$-RRRRRRRRRFFC-CO$_2$H | 61 |
|---|---|---|---|
| NA | RXR4 | NH$_2$-RXRRXRRXRRXRXB-CO$_2$H | 62 |
| NA | P008RX8 | NH$_2$-RXRXRXRXRXRXRXRXB-CO$_2$H | 63 |
| NA | RX4 | NH$_2$-RXRXRXRXB-CO$_2$H | 64 |
| NA | RXR2 | NH$_2$-RXRRXRXB-CO$_2$H | 65 |
| NA | RXR3 | NH$_2$-RXRRXRRXRXB-CO$_2$H | 66 |

| GenBank Accession Number | Name | Target Regions | |
|---|---|---|---|
| gi\|101413003: 032-3154 | EBOV Zaire Mayinga_VP35 | GATGAAGATTAAAACCTTCATCATCCTTACGT CAATTGAATTCTCTAGCACTCGAAGCTTATTG TCTTCAATGTAAAAGAAAAGCTGGTCTAACA AGATGACAACTAGAACAAAGGGCAGGGG | 67 |
| gi\|33860540: 3032-3154 | EBOV Zaire 1995_VP35 | GATGAAGATTAAAACCTTCATCATCCTTACGT CAATTGAATTCTCTAGCACTCGAAGCTTATTG TCCTCAATGTAAAAGAAAAGCTGGTCTAACA AGATGACAACCAGAACAAAGGGCAGGGG | 68 |
| gi\|52352969: 3011-3163 | EBOV Sudan Gulu_VP35 | ATGATGAAGATTAAAACCTTCATCATCCTTTA AAAAGAGAGCTATTCTTTATCTGAATGTCCTT ATTAATGTCTAAGAGCTATTATTTTGTACCCT CTTAGCCTAGACACTGCCCAGCATATAAGCCA TGCAGCAGGATA GGACTTATAGACA | 69 |
| gi\|22671623: 3019-3180 | EBOV Reston PA_VP35 | GATGAAGATTAAAACCTTCATCGCCAGTAAAT GATTATATTGTCTGTAGGCAGGTGTTTACTCC ACCTTAAATTTGGAAATATCCTACCTTAGGAC CATTGTCAAGAGGTGCATAGGCATTACCACCC TTGAGAACATGTACAATAATAAATTGAAGGT ATG | 70 |
| gi\|450908: 2853-2944 | MARV Popp_VP35 | GAAGAATATTAAAGGTTTTCTTTAATATTCAG AAAAGGTTTTTTATTCTCTTCTTTCTTTTTGCA AACATATTGAAATAATAATTTTCACAA | 71 |
| gi\|10141003: 9885-10370 | EBOV Zaire Mayinga_VP24 | GATGAAGATTAATGCGGAGGTCTGATAAGAA TAAACCTTATTATTCAGATTAGGCCCCAAGAG GCATTCTTCATCTCCTTTTAGCAAAGTACTATT TCAGGGTAGTCCAATTAGTGGCACGTCTTTTA GCTGTATATCAGTCGCCCCTGAGATACGCCAC AAAAGTGTCTCTAAGCTAAATTGGTCTGTACA CATCCCATACATTGTATTAGGGGCAATAATAT CTAATTGAACTTAGCCGTTTAAAATTTAGTGC ATAAATCTGGGCTAACACCACCAGGTCAACTC CATTGGCTGAAAAGAAGCTTACCTACAACGA ACATCACTTTGAGCGCCCTCACAATTAAAAAA TAGGAACGTCGTTCCAACAATCGAGCGCAAG GTTTCAAGGTTGAACTGAGAGTGTCTAGACAA CAAAATATTGATACTCCAGACACCAAGCAAG ACCTGAGAAAAACCATGGCTAAAGCTACGG GACGATACAA | 72 |
| gi\|33860540: 9886-10371 | EVOV Zaire 1995_VP24 | GATGAAGATTAATGCGGAGGTCTGATAAGAA TAAACCTTATTATTCAGATTAGGCCCCAAGAG GCATTCTTCATCTCCTTTTAGCAAAGTACTATT TCAGGGTAGTCCAATTAGTGACACGTCTCTTA GCTGTATATCAGTCGCCCCTGAGATACGCCAC | 73 |

| | | Sequence Listing Table | | |
|---|---|---|---|---|
| gi\|52352969:<br>9824-10324 | EBOV Sudan<br>Gulu_VP24 | AAAAGTGTCTCTAAGCTAAATTGGTCTGTACA<br>CATCTCATACATTGTATTAGGGACAATAATAT<br>CTAATTGAACTTAGCCGTTTAAAATTTAGTGC<br>ATAAATCTGGGCTAACTCCACCAGGTCAACTC<br>CATTGGCTGAAAAGAAGCCTACCTACAACGA<br>ACATCACTTTGAGCGCCCTCACATTTAAAAAA<br>TAGGAACGTCGTTCCAACAATCGAGCGCAAG<br>GTTTCAAGGTTGAACTGAGAGTGTCTAGACAA<br>CAAAGTATCGATCCTCCAGACACCAAGCAAG<br>ACCTGAGAAAAACCATGGCTAAAGCTACGG<br>GACGATACAA<br><br>ATGATGAAAATTAATGAGAAGGTTCCAAGAT<br>TGACTTCAATCCAAACACCTTGCTCTGCCAAT<br>TTTCATCTCCTTAAGATATATGATTTTGTTCCT<br>GCGAGATAAGGTTATCAAATAGGGTGTGTAT<br>CTCTTTTACATATTTGGGCTCCCACTAGGCTA<br>GGGTTTATAGTTAAGGAAGACTCATCACATTT<br>TTTATTGAACTAGTCTACTCGCAGAATCCTAC<br>CGGGAATAGAAATTAGAACATTTGTGATACTT<br>TGACTATAGGAAATAATTTTCAACACTACCTG<br>AGATCAGGTTATTCTTCCAACTTATTCTGCAA<br>GTAATTGTTTAGCATCATAACAACGTTAT<br>AATTTAAGAATCAAGTCTTGTAACAGAAATA<br>AAGATAACAGAAAGAACCTTTATTATACGGG<br>TCCATTAATTTTATAGGAGAAGCTCCTTTTAC<br>AAGCCTAAGATTCCATTAGAGATAACCAGAA<br>TGGCTAAAGCCACA<br>GGCCGGTACAA | 74 |
| gi\|22671623:<br>9832-10328 | EBOV Reston<br>PA_VP24 | GATGAAGATTAATTGCGGAGGAATCAGGAAT<br>TCAACTTTAGTTCCTTAAGGCCTCGTCCGAAT<br>CTTCATCAGTTCGTAAGTTCTTTTATAGAAGT<br>CATTAGCTTCTAAGGTGATTATATTTTAGTATT<br>AAATTTTGCTAATTGCTTGCTATAAAGTTGAA<br>ATGTCTAATGCTTAAATGAACACTTTTTTGAA<br>GCTGACATACGAATACATCATATCATATGAAA<br>ACATCGCAATTAGAGCGTCCTTGAAGTCTGGC<br>ATTGACAGTCACCAGGCTGTTCTCAGTAGTCT<br>GTCCTTGGAAGCTCTTGGGGAGACAAAAGA<br>GGTCCCAGAGAGTCCCAACAGGTTGGCATAA<br>GGTCATTAACACCAGCATAGTCGGCTCGACCA<br>AGACTGTAAGCGAGTCGATTTCAACTAAAAA<br>GATTATTTCTTGTTGTTTAAACAAATTCCTTTT<br>GTGTGAGACATCCTCAAGGCACAAGATGGCT<br>AAAGCCACAGGCC<br>GATACAA | 75 |
| gi\|450908:<br>9997-10230 | MARV<br>Popp VP24 | GAAGAACATTAAGAAAAGGATGTTCTTATTT<br>TTCAACTAAACTTGCATATCCTTTGTTGATAC<br>CCTTGAGAGACAACTTTTGACACTAGATCACG<br>GATCAAGCATATTTCATTCAAACACCCCAAAT<br>TTTCAATCATACACATAATAACCATTTTAGTA<br>GCGTTACCTTTCAATACAATCTAGGTGATTGT<br>GAAAAGACTTCCAAACATGGCAGAATTATCA<br>ACGCGTTACAA | 76 |

*"X" and "B" denote 6-aminohexanoic acid and beta-alanine, respectively.
**SEQ ID NOs: 40 and 41 incorporated the cationic linkage (1-piperazino phosphoramidate) as shown in FIG. 2H, at the positions indicated, for example, with a "+".

It is claimed:

1. An antisense oligonucleotide compound comprising morpholino subunits linked by phosphorous-containing intersubunit linkages, the intersubunit linkages joining a 3' morpholino nitrogen of one subunit to a 5' exocyclic carbon of an adjacent subunit in accordance with the following structure:

wherein:
- $P_j$ and $P_i$ are, at each occurrence, independently a purine or pyrimidine base-pairing moiety effective to bind, by base-specific hydrogen bonding, to a base in a polynucleotide; and
- X is, at each occurrence, independently alkyl, alkoxy, thioalkoxy, a cyclic amine, or —N(R)$_2$, wherein each R is independently H or lower alkyl, and
- wherein the antisense oligonucleotide compound is targeted against Marburg virus NP gene and comprises a sequence having at least 90% sequence homology to the sequence set forth in SEQ ID NO:79.

2. The antisense oligonucleotide compound of claim 1, wherein each X is independently —N(CH$_3$)$_2$ or 1-piperazino.

3. The antisense oligonucleotide compound of claim 1, wherein the antisense oligonucleotide compound comprises a sequence having at least 95% sequence homology to the sequence set forth in SEQ ID NO:79.

4. The antisense oligonucleotide compound of claim 1, wherein the antisense oligonucleotide compound consists of the sequence set forth in SEQ ID NO:79.

5. A Pharmaceutical composition comprising an antisense oligonucleotide compound and a physiologically acceptable carrier, wherein the oligonucleotide compound comprises morpholino subunits linked by phosphorous-containing intersubunit linkages, the intersubunit linkages joining a 3' morpholino nitrogen of one subunit to a 5' exocyclic carbon of an adjacent subunit in accordance with the following structure:

wherein:
  P$_j$ and P$_i$ are, at each occurrence, independently a purine or pyrimidine base-pairing moiety effective to bind, by base-specific hydrogen bonding, to a base in a polynucleotide; and
  X is, at each occurrence, independently alkyl, alkoxy, thioalkoxy, a cyclic amine, or —N(R)$_2$, wherein each R is independently H or lower alkyl, and
  wherein the antisense oligonucleotide compound is targeted against Marburg virus NP gene and comprises a sequence having at least 90% sequence homology to the sequence set forth in SEQ ID NO:79.

6. The pharmaceutical composition of claim 5, wherein each X is independently —N(CH$_3$)$_2$ or 1-piperazino.

7. The pharmaceutical composition of claim 5, wherein the antisense oligonucleotide compound comprises a sequence having at least 95% sequence homology to the sequence set forth in SEQ ID NO:79.

8. The pharmaceutical composition of claim 5, wherein the antisense oligonucleotide compound consists of the sequence set forth in SEQ ID NO:79.

9. A method for treating a Marburg infection in a mammalian host, the method comprising administering a therapeutically effective amount of the composition of claim 5 to the host.

10. The method of claim 9, wherein each X is independently —N(CH$_3$)$_2$ or 1-piperazino.

11. The method of claim 9, wherein the antisense oligonucleotide compound comprises a sequence having at least 95% sequence homology to the sequence set forth in SEQ ID NO:79.

12. The method of claim 9, wherein the antisense oligonucleotide compound consists of the sequence set forth in SEQ ID NO:79.

13. A method of vaccinating a mammalian subject against Marburg virus, the method comprising administering a therapeutically effective amount of the composition of claim 5 to the subject.

14. The method of claim 13, wherein each X is independently —N(CH$_3$)$_2$ or 1-piperazino.

15. The method of claim 13, wherein the antisense oligonucleotide compound comprises a sequence having at least 95% sequence homology to the sequence set forth in SEQ ID NO:79.

16. The method of claim 13, wherein the antisense oligonucleotide compound consists of the sequence set forth in SEQ ID NO:79.

* * * * *